US012734213B2

(12) United States Patent
Mor et al.

(10) Patent No.: US 12,734,213 B2
(45) Date of Patent: Sep. 15, 2026

(54) ANTIVIRAL COMPOSITIONS AND METHODS

(71) Applicant: WAYNE STATE UNIVERSITY, Detroit, MI (US)

(72) Inventors: Gil Mor, Southfield, MI (US); Jiahui Ding, Detroit, MI (US)

(73) Assignee: Wayne State University, Detroit, MI (US)

( * ) Notice: Subject to any disclaimer, the term of this patent is extended or adjusted under 35 U.S.C. 154(b) by 895 days.

(21) Appl. No.: 17/923,763

(22) PCT Filed: May 10, 2021

(86) PCT No.: PCT/US2021/031571

§ 371 (c)(1),
(2) Date: Nov. 7, 2022

(87) PCT Pub. No.: WO2021/226583

PCT Pub. Date: Nov. 11, 2021

(65) Prior Publication Data

US 2023/0181685 A1 Jun. 15, 2023

Related U.S. Application Data

(60) Provisional application No. 63/021,747, filed on May 8, 2020.

(51) Int. Cl.

| | |
|---|---|
| ***A61K 38/17*** | (2006.01) |
| ***A61K 9/107*** | (2006.01) |
| ***A61K 9/127*** | (2025.01) |
| ***A61K 38/46*** | (2006.01) |
| ***A61K 47/54*** | (2017.01) |
| ***A61K 47/59*** | (2017.01) |
| ***A61K 47/68*** | (2017.01) |
| ***A61P 31/14*** | (2006.01) |
| ***A61P 31/20*** | (2006.01) |

(52) U.S. Cl.

CPC .......... *A61K 38/1709* (2013.01); *A61K 47/59* (2017.08); *A61P 31/14* (2018.01); *A61P 31/20* (2018.01)

(58) Field of Classification Search

None

See application file for complete search history.

(56) References Cited

FOREIGN PATENT DOCUMENTS

CN 104013954 A 9/2014

OTHER PUBLICATIONS

Fischer, Cellular Uptake Mechanisms and Potential Therapeutic Utility of Peptidic Cell Delivery Vectors: Progress 2001-2006, Medicinal Research Reviews, 2007, 27, pp. 755-795.*

Extended European Search Report for European Application No. 21800070.1, dated May 7, 2024.

Ding, J. et al., P31: Identification, expression and isolation of ISG20 protein as an efficient inhibitor of ZIKA infection in trophoblast cells, American Journal of Reproductive Immunology, 81, P31: 52-53, May 31, 2019.

Ding, J. et al., P6: Identification and characterization of placental ISG20 as a critical meditator of IFN-beta response to ZIKA viral infection, American Journal of Reproductive Immunology, 80, P6: 62, Jun. 26, 2018.

Leong. C. et al., Interferon-stimulated gene of 20 kDa protein (ISG20) degrades RNA of hepatitis B virus to impede the replication of HBV in vitro and in vivo, Oncotarget, 7(42): 68179-68193, Oct. 18, 2016.

Zhou, Z. et al., Antiviral activities of ISG20 in positive-strand RNA virus infections, Virology, 409(2): 175-188, Jan. 20, 2011.

Espert, L. et al., ISG20, a New Interferon-induced RNase Specific for Single-stranded RNA, Defines an Alternative Antiviral Pathway against RNA Genomic Viruses, Journal of Biological Chemistry, 278(18): 16151-16158, , May 1, 2003.

Ding, J. et al., Placenta-derived interferon-stimulated gene 20 controls ZIKA virus infection, EMBO Reports, 22(10), Aug. 18, 2021, pp. 1-19.

Blanco-Melo et al., Imbalanced Host Response to SARS-CoV-2 Drives Development of COVID-19. Cell. May 28, 2020, vol. 181, No. 5, pp. 1036-1045.e9, abstract, p. 1040, col. 2, para 3, 20 pages.

PCT Search Report and Written Opinion for Application No. PCT/US2021/031571 mailed Nov. 12, 2021, 11 pages.

Zheng et al., Interferon-stimulated gene 20-kDa protein (ISG20) in infection and disease: Review and outlook, Zhiwei Intractable & Rare Diseases Research, vol. 6, No. 1, pp. 35-40, 2017.

(Continued)

*Primary Examiner* — Manjunath N Rao

*Assistant Examiner* — Jae W Lee

(74) *Attorney, Agent, or Firm* — Julie K. Staple; Fishman Stewart PLLC

(57) ABSTRACT

Compositions and methods are provided according to aspects of the present disclosure for inhibition of a pathogenic virus. According to particular aspects, compositions and methods of the present disclosure include degradation of pathogenic viral nucleic acids by interferon-stimulated gene 20-kDa protein (ISG20) and/or a variant thereof, administered to a cell and/or subject to inhibit a pathogenic viral infection of the cell and/or a subject. Compositions and methods are provided according to aspects of the present disclosure wherein providing the ISG20 protein, or a variant thereof, comprises administering a therapeutically effective amount of the ISG20 protein and/or variant, to a subject having, or at risk of having, a viral infection.

9 Claims, 37 Drawing Sheets

Specification includes a Sequence Listing.

(56) References Cited

OTHER PUBLICATIONS

Chinese First Office Action for corresponding Application No. 202180047423.7 issued Mar. 24, 2026, 5 pages.
English Translation of Chinese First Office Action for corresponding Application No. 202180047423.7 issued Mar. 24, 2026, 6 pages.

* cited by examiner

ANTIVIRAL COMPOSITIONS AND METHODS

REFERENCE TO RELATED APPLICATIONS

This application claims priority to PCT Application Serial No. PCT/US202V031571, filed May 10, 2021, which claims priority to U.S. Provisional Patent Application Ser. No. 63/021,747, filed May 8, 2020, the entire content of both of which is incorporated herein by reference.

GRANT REFERENCE

This invention was made with government support under Grant No. R01 A1145829, awarded by the National Institutes of Health. The Government has certain rights in the invention.

FIELD OF THE INVENTION

The present disclosure relates generally to compositions and methods for inhibition of a pathogenic virus. According to particular aspects, compositions and methods of the present disclosure include degradation of pathogenic viral nucleic acids by interferon-stimulated gene 20-kDa protein (ISG20) administered to a cell and/or subject to inhibit a pathogenic viral infection of the cell and/or a subject. In specific aspects, the present disclosure relates to compositions and methods including ISG20 for treatment of a pathogenic viral infection in a subject in need thereof.

BACKGROUND OF THE INVENTION

Pathogenic viral infection is a source of significant morbidity and mortality in both human and non-human populations.

For example, ZIKA virus (ZIKV), is a mosquito-borne flavivirus that was initially isolated from a rhesus monkey in the Zika forest in Uganda in 1947. In 2015, there was a dramatic increase in reports of Zika infections and a strong association of microcephaly in newborns from ZIKV infected mothers, suggesting a correlation between ZIKV infection in pregnancy and fetal malformations.

Further, in recent years, novel coronaviruses have emerged periodically in different areas around the world. Severe acute respiratory syndrome coronavirus (SARS-CoV) outbreak occurred in 2002, which led to 8422 people infected and 916 deaths worldwide during the epidemic. Middle East respiratory syndrome coronavirus (MERS-CoV) was first identified in 2012, causing a total of 1401 MERS-CoV infections, and 543 (~39%) of which died. In January 2020, a novel coronavirus, severe acute respiratory syndrome coronavirus 2 (SARS-CoV-2), was identified as the causative agent of an outbreak of Severe Acute Respiratory Syndrome (SARS) and "COVID-19" (coronavirus disease-2019) centered around Wuhan and rapidly spreading worldwide.

Therefore, there is a continuing need for treatment and prevention of virus-mediated disease.

SUMMARY OF THE INVENTION

Methods of inhibiting a pathogenic virus are provided according to the present disclosure which include providing an ISG20 protein to a cell infected by the pathogenic virus or at risk of being infected by the pathogenic virus, thereby inhibiting the pathogenic virus.

Methods of inhibiting a pathogenic virus are provided according to the present disclosure which include providing an ISG20 protein to a cell infected by the pathogenic virus or at risk of being infected by the pathogenic virus, thereby inhibiting the pathogenic virus, wherein providing the ISG20 protein comprises administering a therapeutically effective amount of the ISG20 protein to a subject having, or at risk of having, a viral infection.

Methods of inhibiting a pathogenic virus are provided according to the present disclosure which include providing an ISG20 protein to a cell infected by the pathogenic virus or at risk of being infected by the pathogenic virus, thereby inhibiting the pathogenic virus, wherein providing the ISG20 protein comprises administering a therapeutically effective amount of the ISG20 protein to a subject having, or at risk of having, a pathogenic viral infection by a positive-sense single-stranded RNA virus.

Methods of inhibiting a pathogenic virus are provided according to the present disclosure which include providing an ISG20 protein to a cell infected by the pathogenic virus or at risk of being infected by the pathogenic virus, thereby inhibiting the pathogenic virus, wherein providing the ISG20 protein comprises administering a therapeutically effective amount of the ISG20 protein to a subject having, or at risk of having, a pathogenic viral infection by a DNA virus.

Methods of inhibiting a pathogenic virus are provided according to the present disclosure which include providing an ISG20 protein to a cell infected by the pathogenic virus or at risk of being infected by the pathogenic virus, thereby inhibiting the pathogenic virus, wherein providing the ISG20 protein comprises administering a therapeutically effective amount of the ISG20 protein to a subject having, or at risk of having, viral infection by a virus selected from the group consisting of: Coronavirus, Zika virus, Hepatitis A virus (HAV), Hepatitis virus (HBV), Hepatitis C virus (HCV), Yellow fever virus (YFV), Bovine viral diarrhea virus (BVDV), Vesicular stomatitis virus (VSV), Encephalomyocarditis virus (EMCV), Influenza virus, Human immunodeficiency virus (HIV), Sindbis virus (SB), West Nile virus, Dengue virus, Kaposi's sarcoma-associated herpesvirus (KSHV), Porcine reproductive and respiratory syndrome virus (PRRSV), Rabies virus (RABV), Epstein-Barr virus (EBV), HSV-2, and Cytomegalovirus Methods of inhibiting a pathogenic coronavirus virus are provided according to the present disclosure which include providing an ISG20 protein to a cell infected by the pathogenic coronavirus virus or at risk of being infected by the pathogenic virus, thereby inhibiting the pathogenic coronavirus, wherein providing the ISG20 protein comprises administering a therapeutically effective amount of the ISG20 protein to a subject having, or at risk of having, a coronavirus infection. According to aspects of the present disclosure, administering the ISG20 protein to a subject having, or at risk of having, the pathogenic coronavirus infection comprises administering a nucleic acid molecule encoding the ISG20 protein. According to aspects of the present disclosure, providing the ISG20 protein to the cell infected by the coronavirus results in at least partial degradation of nucleic acid of the coronavirus. According to aspects of the present disclosure, the ISG20 comprises SEQ ID NO:1, or a variant thereof. According to aspects of the present disclosure, the ISG20 is recombinantly produced. According to aspects of the present disclosure, the ISG20 is isolated. According to aspects of the present disclosure, the ISG20 comprises a cell-targeting component.

Methods of inhibiting a pathogenic severe acute respiratory syndrome coronavirus 2 (SARS-CoV-2) virus are provided according to the present disclosure which include providing an ISG20 protein to a cell infected by the pathogenic SARS-CoV-2 virus or at risk of being infected by the pathogenic SARS-CoV-2 virus, thereby inhibiting the pathogenic SARS-CoV-2 virus, wherein providing the ISG20 protein comprises administering a therapeutically effective amount of the ISG20 protein to a subject having, or at risk of having, infection by SARS-CoV-2 virus. According to aspects of the present disclosure, administering the ISG20 protein to a subject having, or at risk of having, the pathogenic SARS-CoV-2 virus infection comprises administering a nucleic acid molecule encoding the ISG20 protein. According to aspects of the present disclosure, providing the ISG20 protein to the cell infected by the SARS-CoV-2 virus results in at least partial degradation of nucleic acid of the SARS-CoV-2 virus. According to aspects of the present disclosure, the ISG20 comprises SEQ ID NO:1, or a variant thereof. According to aspects of the present disclosure, the ISG20 is recombinantly produced. According to aspects of the present disclosure, the ISG20 is isolated. According to aspects of the present disclosure, the ISG20 comprises a cell-targeting component.

Methods of inhibiting a pathogenic Zika virus are provided according to the present disclosure which include providing an ISG20 protein to a cell infected by the pathogenic Zika virus or at risk of being infected by the pathogenic Zika virus, thereby inhibiting the pathogenic Zika virus, wherein providing the ISG20 protein comprises administering a therapeutically effective amount of the ISG20 protein to a subject having, or at risk of having, a Zika virus infection. According to aspects of the present disclosure, administering the ISG20 protein to a subject having, or at risk of having, the pathogenic Zika virus infection comprises administering a nucleic acid molecule encoding the ISG20 protein. According to aspects of the present disclosure, providing the ISG20 protein to the cell infected by the Zika virus results in at least partial degradation of nucleic acid of the Zika virus. According to aspects of the present disclosure, the ISG20 comprises SEQ ID NO:1, or a variant thereof. According to aspects of the present disclosure, the ISG20 is recombinantly produced. According to aspects of the present disclosure, the ISG20 is isolated. According to aspects of the present disclosure, the ISG20 comprises a cell-targeting component.

Methods of inhibiting a pathogenic HIV are provided according to the present disclosure which include providing an ISG20 protein to a cell infected by the pathogenic HIV or at risk of being infected by the pathogenic HIV, thereby inhibiting the pathogenic virus, wherein providing the ISG20 protein comprises administering a therapeutically effective amount of the ISG20 protein to a subject having, or at risk of having, an HIV infection. According to aspects of the present disclosure, administering the ISG20 protein to a subject having, or at risk of having, the pathogenic HIV infection comprises administering a nucleic acid molecule encoding the ISG20 protein. According to aspects of the present disclosure, providing the ISG20 protein to the cell infected by the virus results in at least partial degradation of nucleic acid of the HIV. According to aspects of the present disclosure, the ISG20 comprises SEQ ID NO:1, or a variant thereof. According to aspects of the present disclosure, the ISG20 is recombinantly produced. According to aspects of the present disclosure, the ISG20 is isolated. According to aspects of the present disclosure, the ISG20 comprises a cell-targeting component.

Methods of inhibiting a pathogenic HSV-2 are provided according to the present disclosure which include providing an ISG20 protein to a cell infected by the pathogenic virus or at risk of being infected by the pathogenic HSV-2, thereby inhibiting the pathogenic HSV-2, wherein providing the ISG20 protein comprises administering a therapeutically effective amount of the ISG20 protein to a subject having, or at risk of having, an HSV-2 infection. According to aspects of the present disclosure, administering the ISG20 protein to a subject having, or at risk of having, the pathogenic HSV-2 infection comprises administering a nucleic acid molecule encoding the ISG20 protein. According to aspects of the present disclosure, providing the ISG20 protein to the cell infected by the HSV-2 results in at least partial degradation of nucleic acid of the HSV-2. According to aspects of the present disclosure, the ISG20 comprises SEQ ID NO:1, or a variant thereof. According to aspects of the present disclosure, the ISG20 is recombinantly produced. According to aspects of the present disclosure, the ISG20 is isolated. According to aspects of the present disclosure, the ISG20 comprises a cell-targeting component.

According to aspects of the present disclosure, administering the ISG20 protein to a subject having, or at risk of having, the pathogenic viral infection comprises administering a nucleic acid molecule encoding the ISG20 protein. According to aspects of the present disclosure, providing the ISG20 protein to the cell infected by the virus results in at least partial degradation of nucleic acid of the virus. According to aspects of the present disclosure, the ISG20 comprises SEQ ID NO:1, or a variant thereof. According to aspects of the present disclosure, the ISG20 is recombinantly produced. According to aspects of the present disclosure, the ISG20 is isolated. According to aspects of the present disclosure, the ISG20 comprises a cell-targeting component.

According to aspects of the present disclosure, the ISG20 protein is protein transduction reagent-modified ISG20 protein, wherein the protein transduction reagent is non-covalently bound to the ISG20 protein, and wherein the protein transduction reagent comprises a cation reagent and a lipid. According to aspects of the present disclosure, the cation reagent comprises polyethylenimine. According to aspects of the present disclosure, the lipid is selected from the group consisting of: DOTMA (N-1(-(2,3-dioleyloxy)propyl-N,N, N-trimethyl-ammonium chloride; DOGS (dioctadecylamido-glycylspermine); DOTAP, 1,2-dioleoyl-3-trimethylammonium-propane; DOPE, 1,2-dioleoyl-n-glycero-3-phosphoethanolamine; POPC, 1-palmitoyl-2-oleoyl-n-glycero-3-phosphocholine; and DMPE 1,2-dimyristoyl-n-glycero-3-phosphocholine. According to aspects of the present disclosure, the protein transduction reagent is selected from the group consisting of: QQ1a, QQ2a, QQ3a, QQ4a, QQ5a, QQ6a, QQ7a, QQ8a and QQ9a.

Methods of inhibiting a Zika virus in a pregnant subject are provided according to aspects of the present disclosure which include providing an ISG20 protein to a cell infected by the Zika virus or at risk of being infected by the Zika virus, thereby inhibiting the Zika virus. According to aspects of the present disclosure, the cell is a placental cell. According to aspects of the present disclosure, the isolated ISG20 protein is recombinantly produced. According to aspects of the present disclosure, the ISG20 protein comprises a cell-targeting component. According to aspects of the present disclosure, the ISG20 protein comprises a placental cell-targeting component. According to aspects of the present disclosure, the ISG20 protein comprises an Fc domain of human $IgG_1$. According to aspects of the present disclosure, the ISG20 a protein transduction reagent-modified ISG20 protein, wherein the protein transduction reagent comprises a cation reagent and a lipid. According to aspects of the present disclosure, the cation reagent comprises polyethylenimine.

According to aspects of the present disclosure, the lipid is selected from the group consisting of: DOTMA (N-1(-(2,3-dioleyloxy)propyl-N,N,N-trimethyl-ammonium chloride; DOGS (dioctadecylamido-glycylspermine); DOTAP, 1,2-dioleoyl-3-trimethylammonium-propane; DOPE, 1,2-dioleoyl-n-glycero-3-phosphoethanolamine; POPC, 1-palmitoyl-2-oleoyl-sn-glycero-3-phosphocholine; and DMPE 1,2-dimyristoyl-n-glycero-3-phosphocholine. According to aspects of the present disclosure, the protein transduction reagent is selected from the group consisting of: QQ1a, QQ2a, QQ3a, QQ4a, QQ5a, QQ6a, QQ7a, QQ8a and QQ9a.

Compositions are provided according to aspects of the present disclosure which include a protein transduction reagent-modified ISG20 protein, or a variant thereof, and a cell targeting component. According to aspects of the present disclosure, the cell targeting component comprises a protein transduction reagent comprising a cation reagent and a lipid, wherein the cation reagent and lipid are non-covalently associated with the ISG20 protein, or the variant thereof. According to aspects of the present disclosure, the cation reagent comprises polyethylenimine. According to aspects of the present disclosure, the lipid is selected from the group consisting of: DOTMA (N-1(-(2,3-dioleyloxy) propyl-N,N,N-trimethyl-ammonium chloride; DOGS (dioctadecylamido-glycylspermine); DOTAP, 1,2-dioleoyl-3-trimethylammonium-propane; DOPE, 1,2-dioleoyl-sn-glycero-3-phosphoethanolamine; POPC, 1-palmitoyl-2-oleoyl-sn-glycero-3-phosphocholine; and DMPE 1,2-dimyristoyl-sn-glycero-3-phosphocholine. According to aspects of the present disclosure, the protein transduction reagent is selected from the group consisting of: QQ1a, QQ2a, QQ3a, QQ4a, QQ5a, QQ6a, QQ7a, QQ8a and QQ9a.

Compositions are provided according to aspects of the present disclosure which include a protein transduction reagent-modified ISG20 protein, or a variant thereof, and a cell targeting component, wherein the cell targeting component comprises an Fc domain of human $IgG_1$, or a variant thereof, wherein the Fc domain of human $IgG_1$, or a variant thereof, is included in a fusion protein with the ISG20 protein, or variant thereof.

BRIEF DESCRIPTION OF THE DRAWINGS

FIG. 1A shows two graphs illustrating ZIKV titers in Sw.71 and HPC trophoblasts; *$p<0.05$, $p<0.01$, *$p<0.001$, ****$p<0.0001$ by One-way ANOVA;

FIG. 1B shows two graphs illustrating that IFNα is not highly induced in response to ZIKV infection in trophoblast cells; IFNα mRNA expression was inhibited in the first 24 h.p.i. and maintained at low level during ZIKV infection;

FIG. 1C shows two graphs illustrating that ZIKV infection induced a time-dependent increase in IFNβ mRNA expression in Sw.71 and HPC.); *$p<0.05$, **$p<0.01$ by One-way ANOVA;

FIG. 1D shows two graphs illustrating that expression levels of secreted IFNβ detected in trophoblast supernatants by ELLA assay; Supernatants were collected from ZIKV-infected and control trophoblast cultures at different times, and IFNβ protein secretion was quantified by ELLA assay. Note the increase of secreted IFNβ in the ZIKV-infected supernatant in a time-dependent manner. ****$p<0.0001$ by Student's t-test against individual time point NT control.

Sw.71 and HPC cells were treated with IFNβ to detect ISG20 mRNA and protein expression.

Data represent as mean±SEM from three independent experiments (each dot represents one independent experiment). NT, no treatment group; HPC, human primary culture.

Figure 2A:
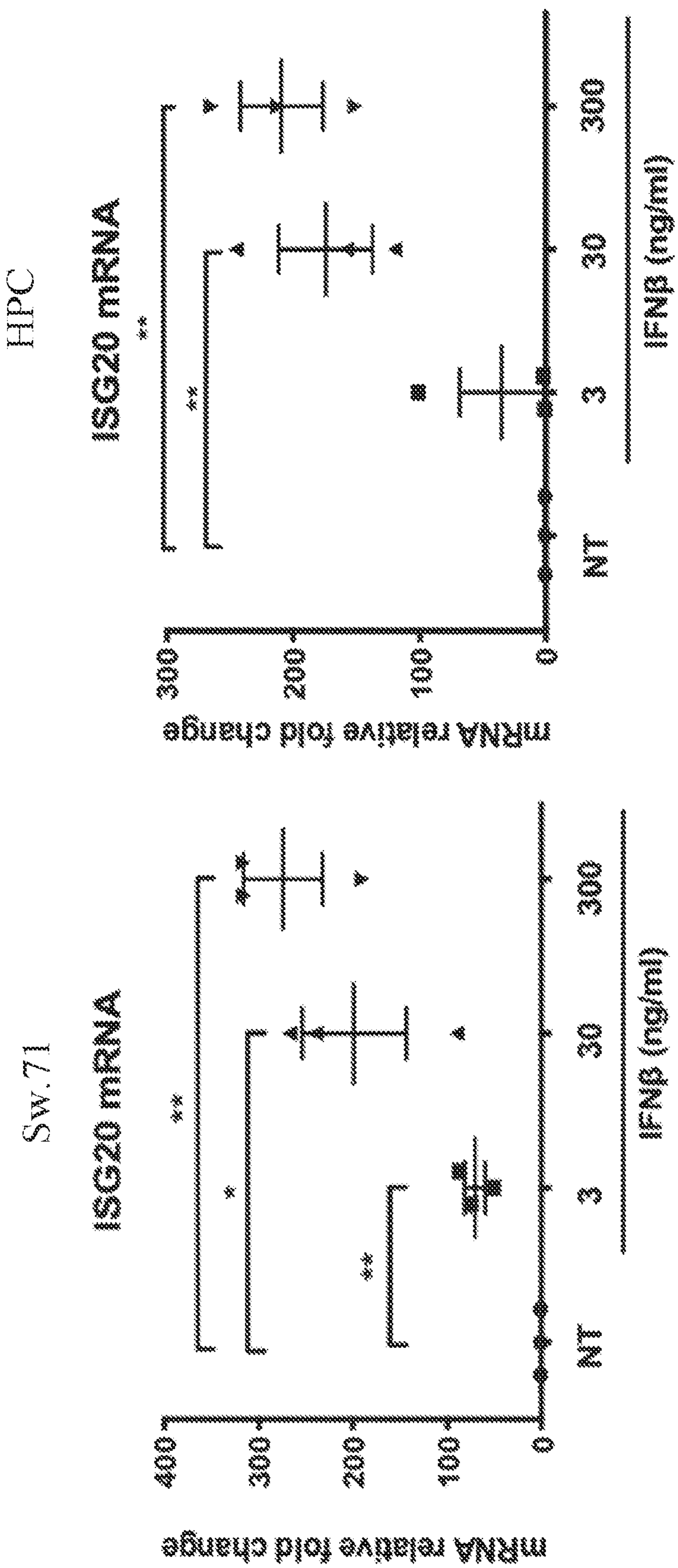
FIGS. 2A, 2B, 2C, and 2D show that IFNβ promotes ISG20 mRNA and protein expression in a dose and time-dependent manner in trophoblast cells.
Figure 2B:
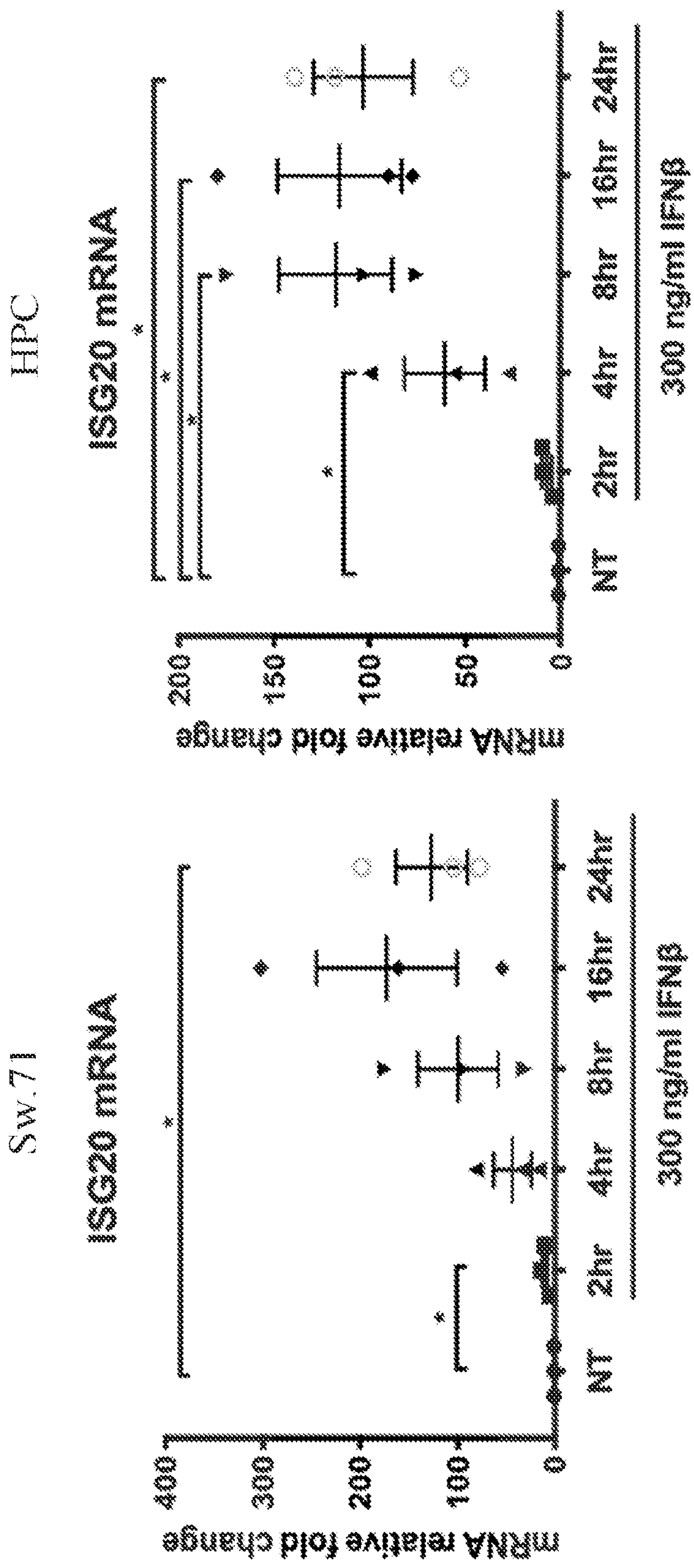
Figure 2C:
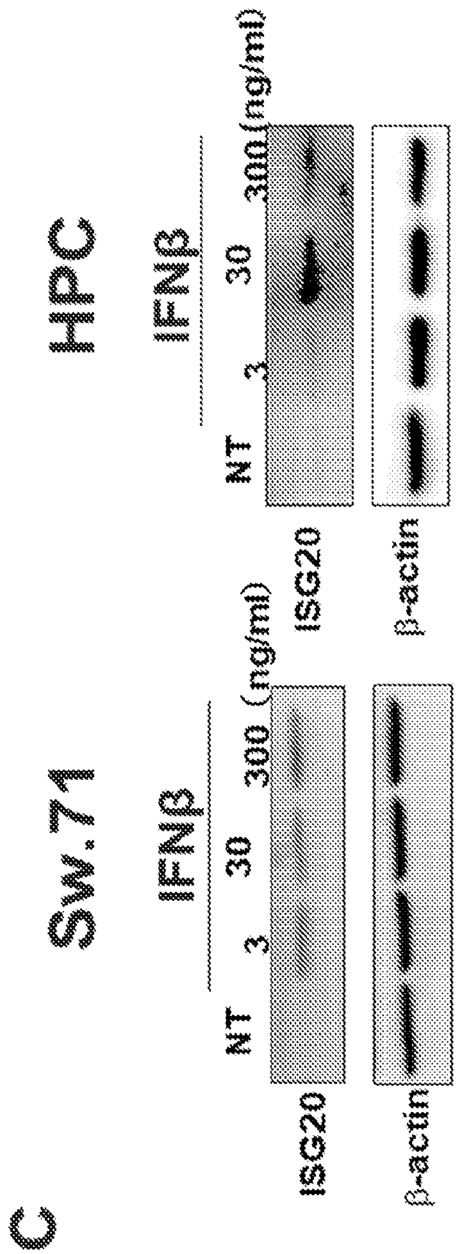
Figure 2D:
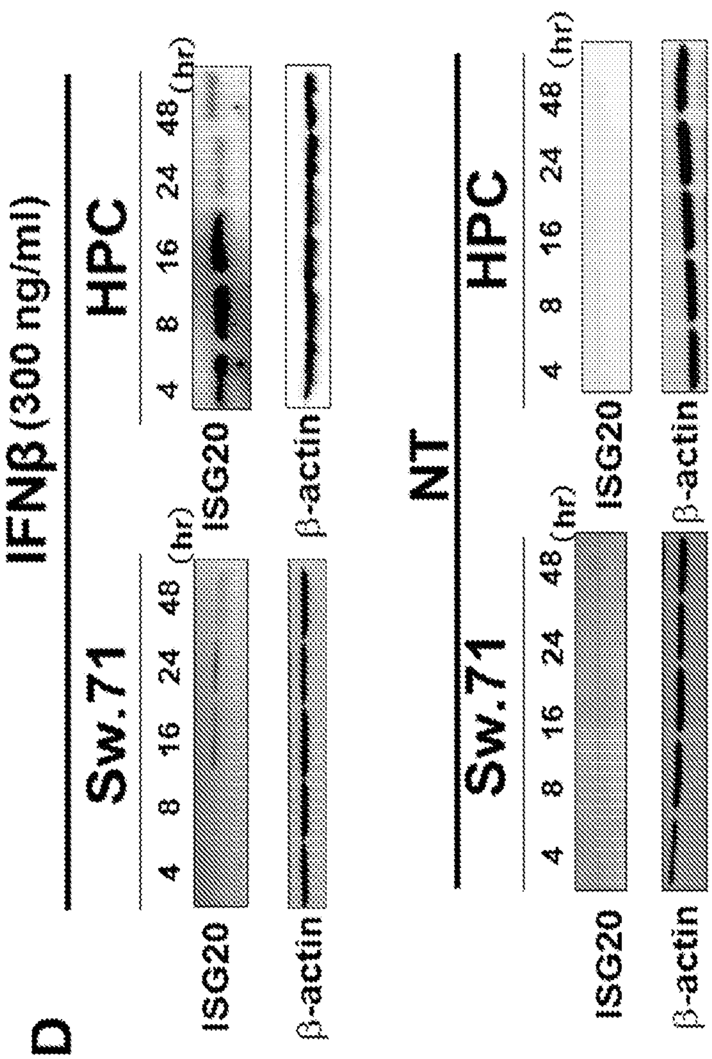
Figure 3B:
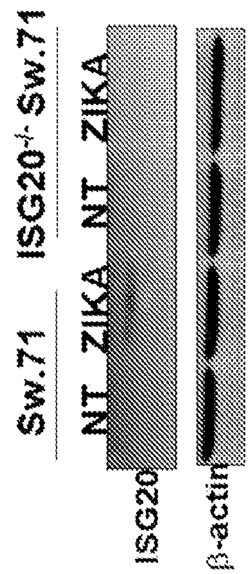
Figure 3A:
Figure 3D:
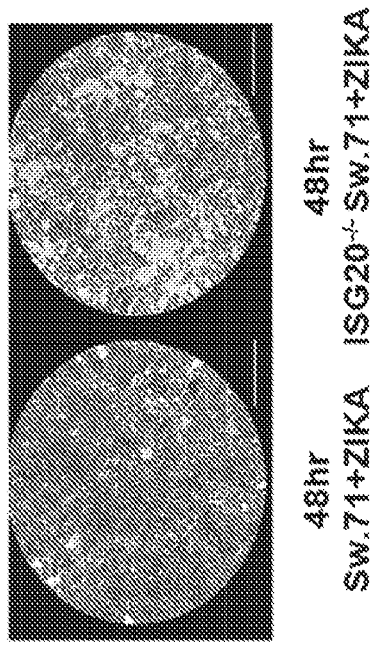
Figure 3C:
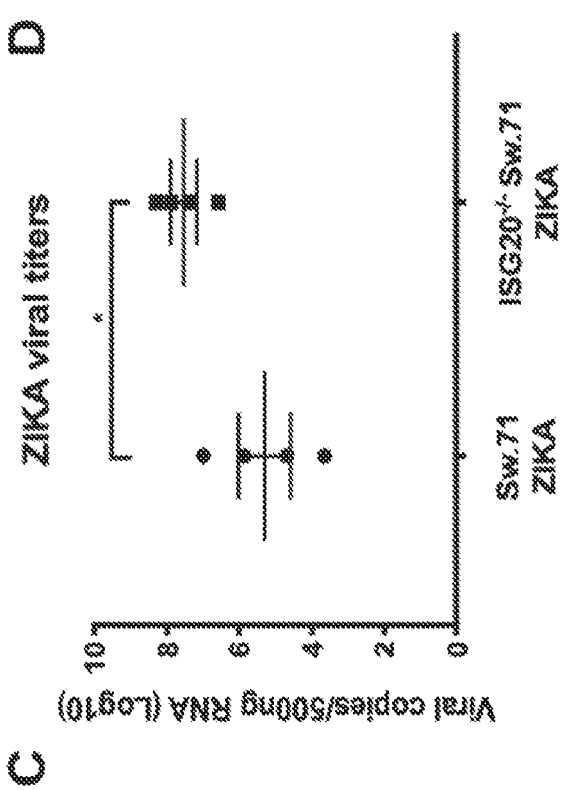
Figure 3E:
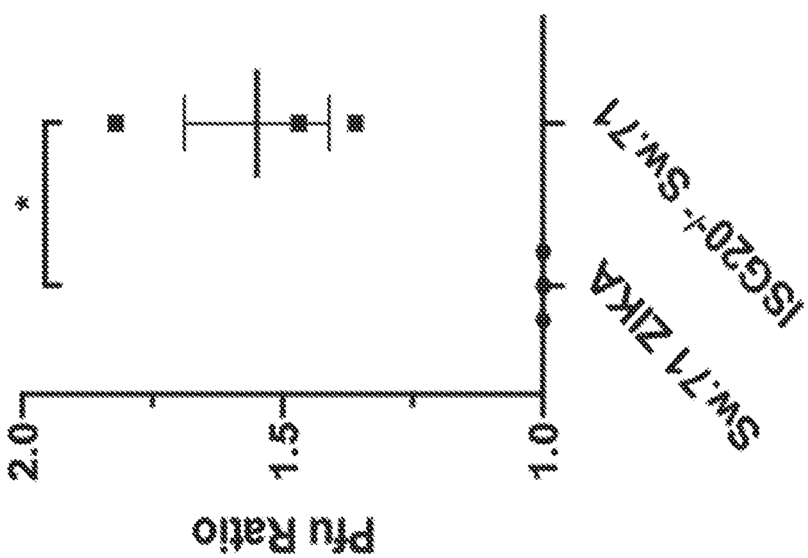
Figure 4A:
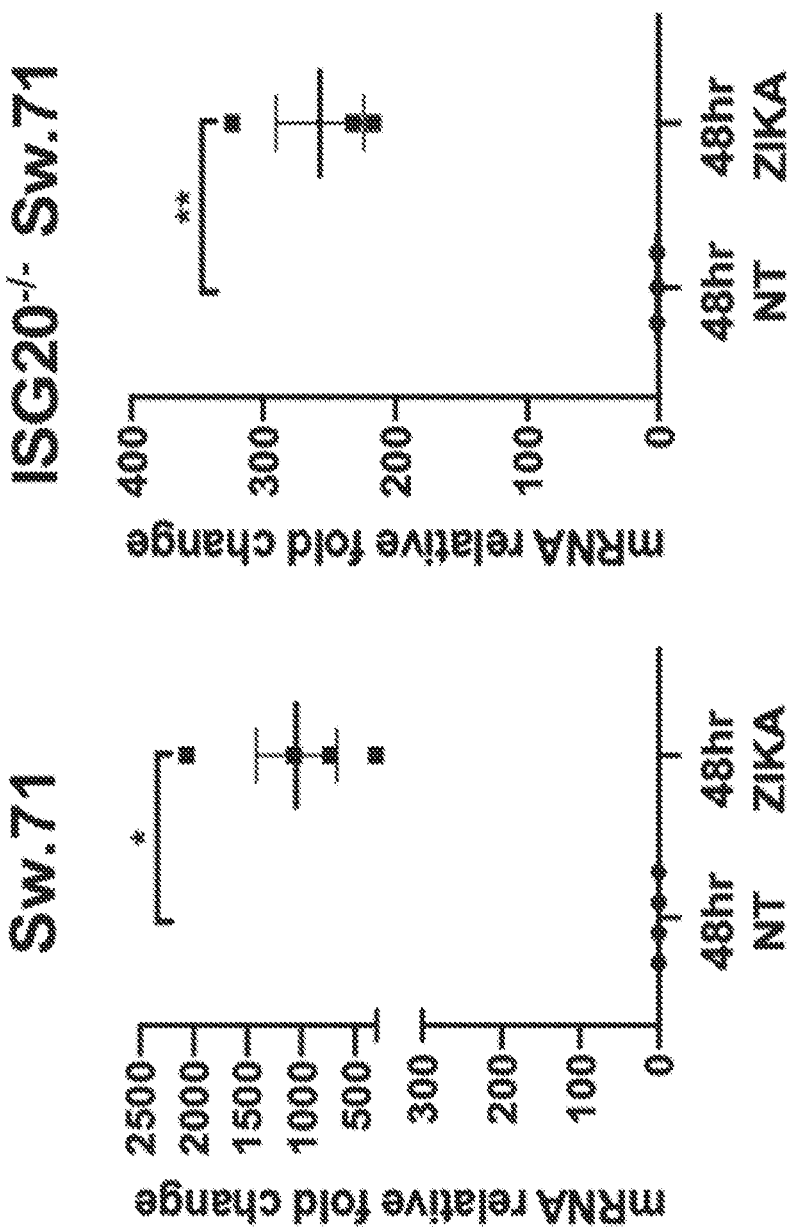
Figure 4B:
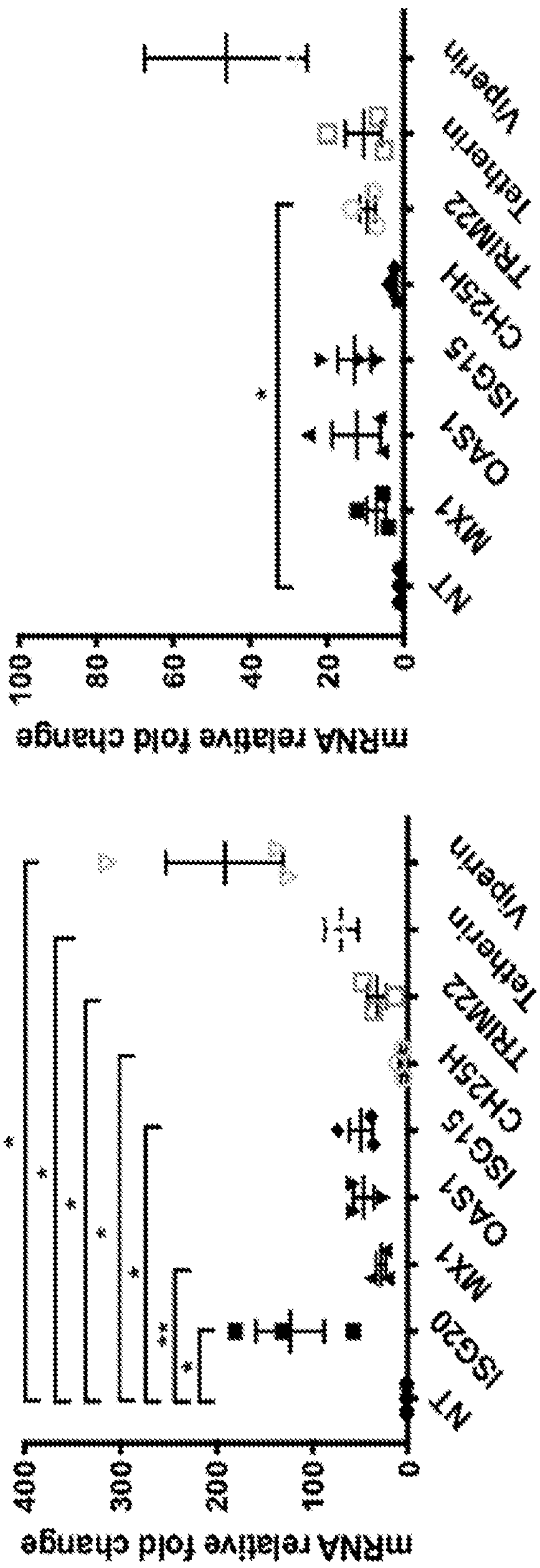
Figure 4C:
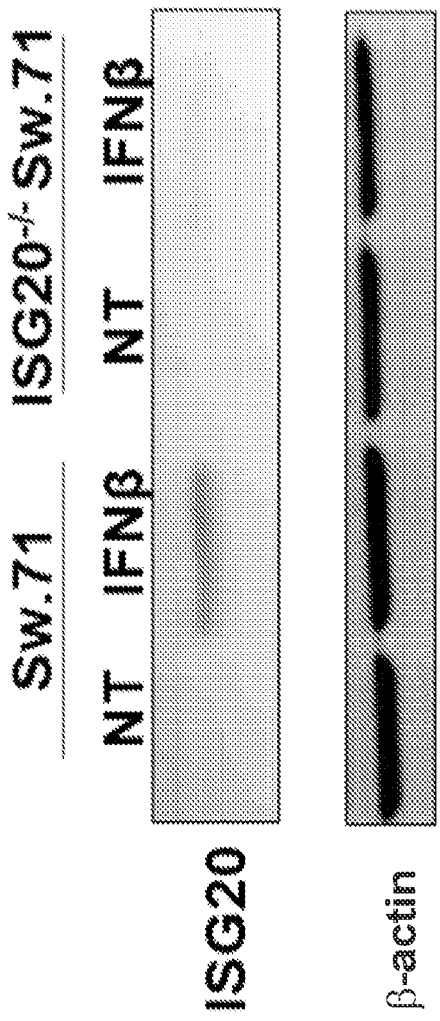
Figure 4D:
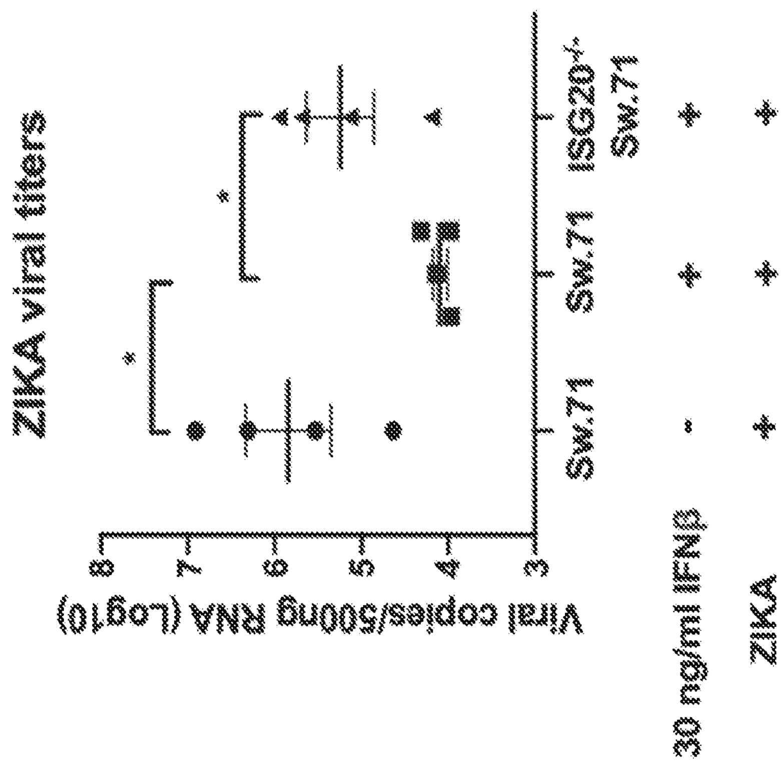
Figure 5A:
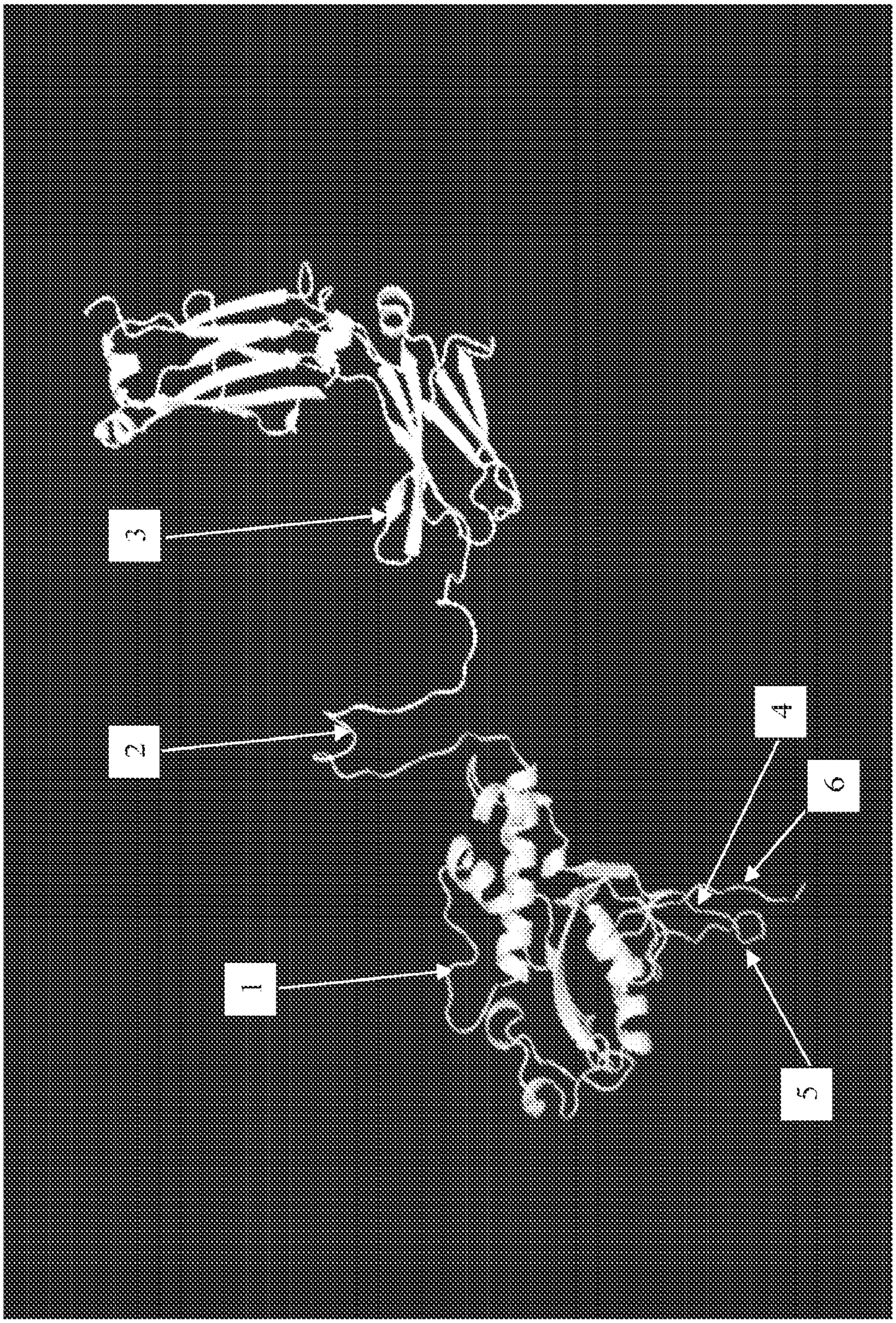
Figure 5B:
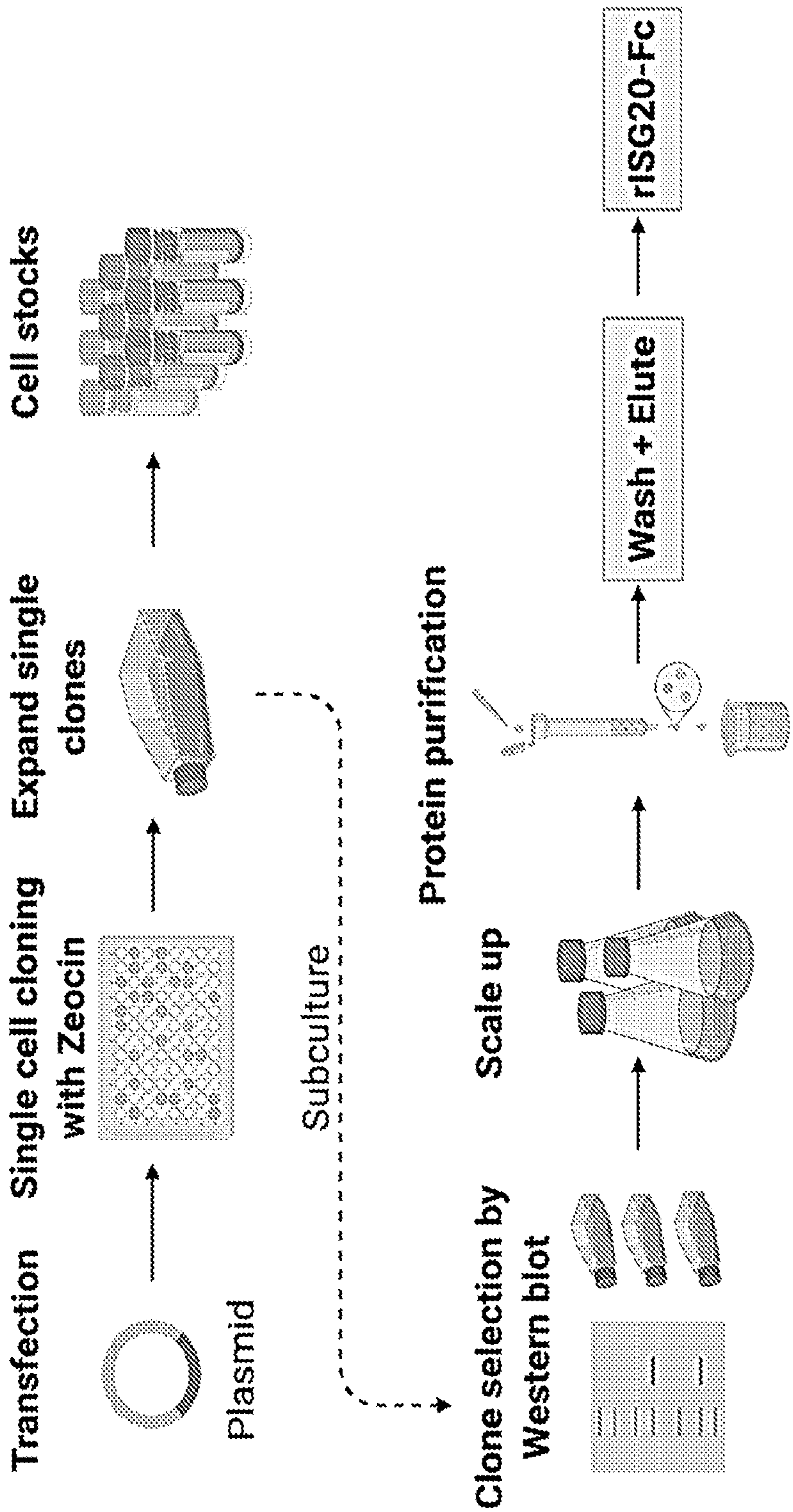
Figure 5D:
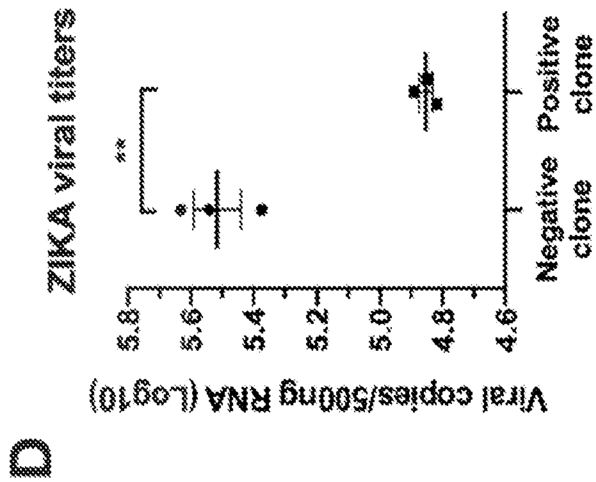
Figure 5C:
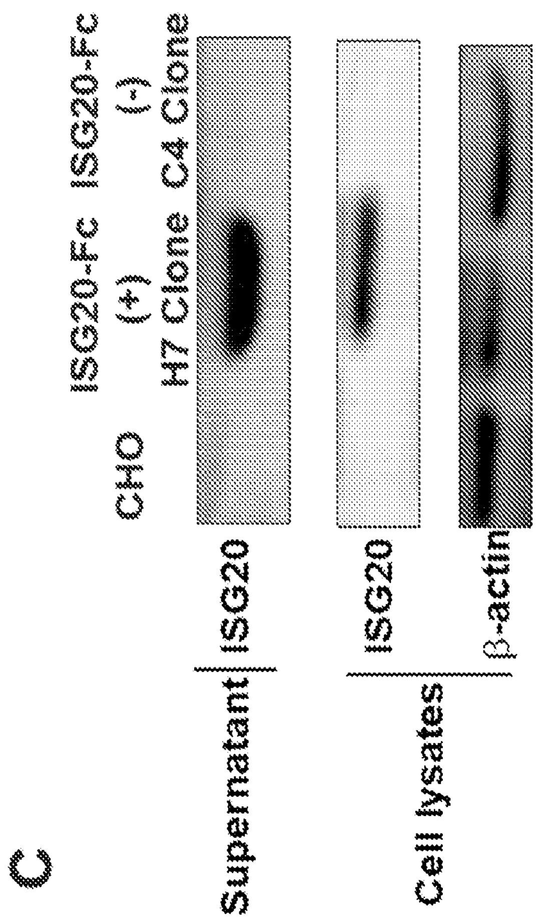
Figure 5E:
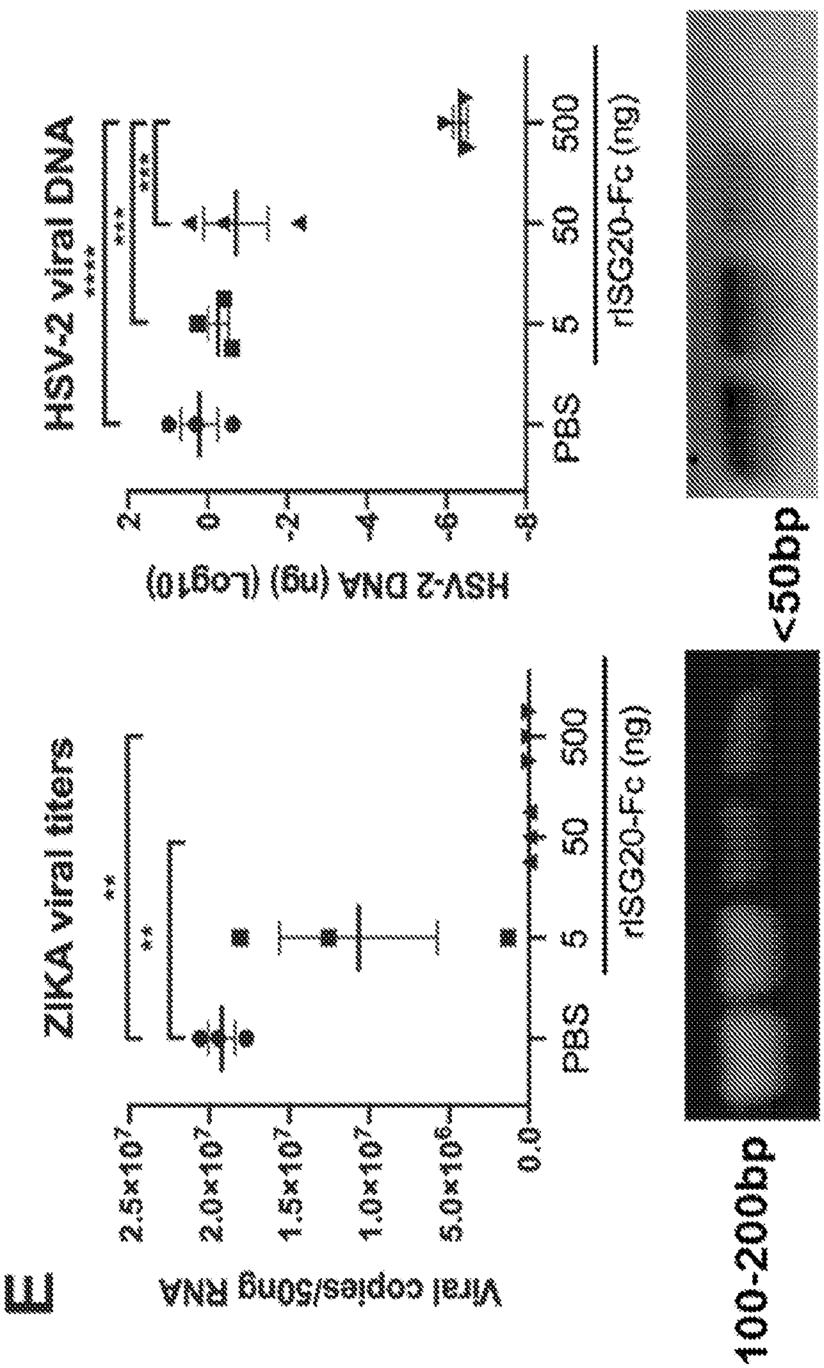
Figure 6A:
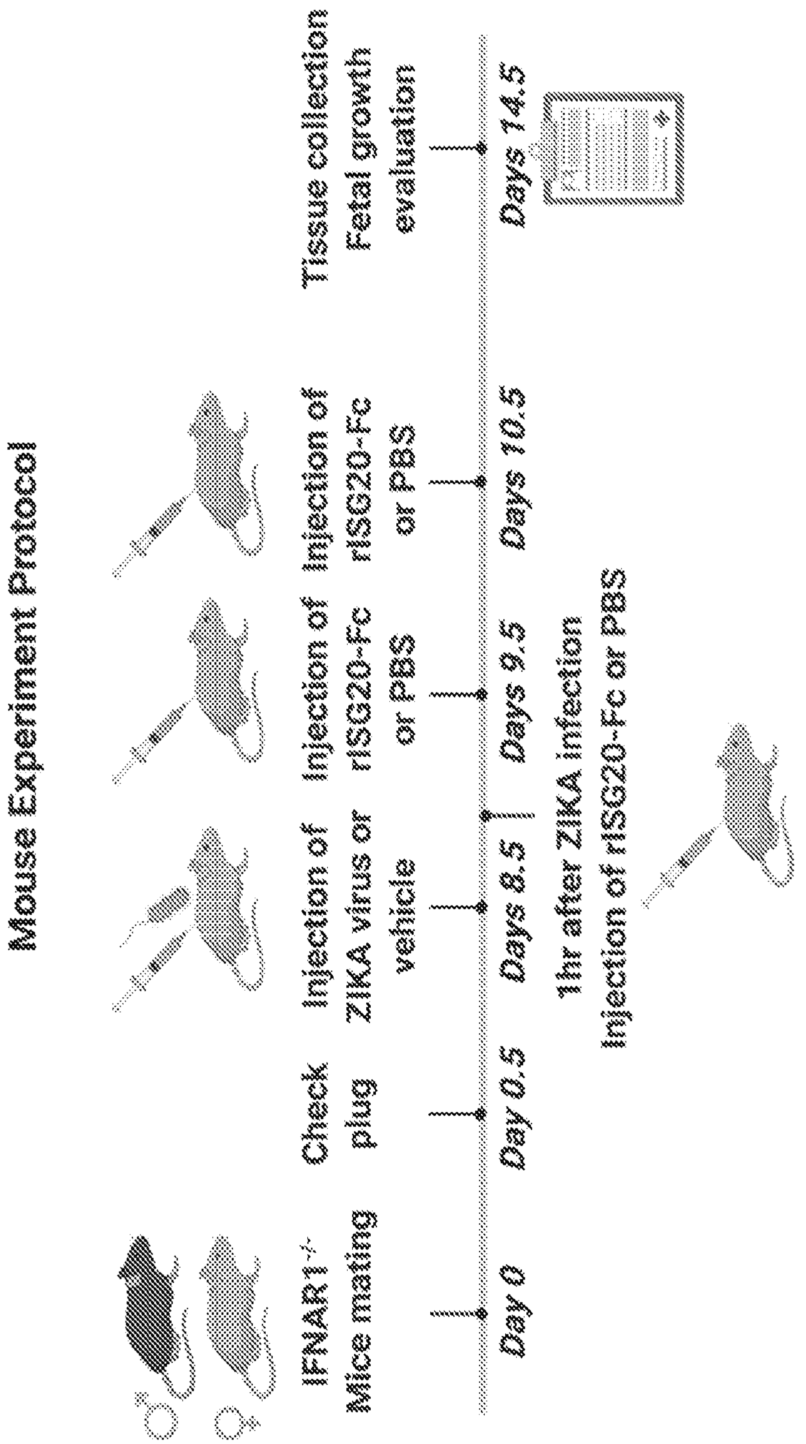
Figure 6B:
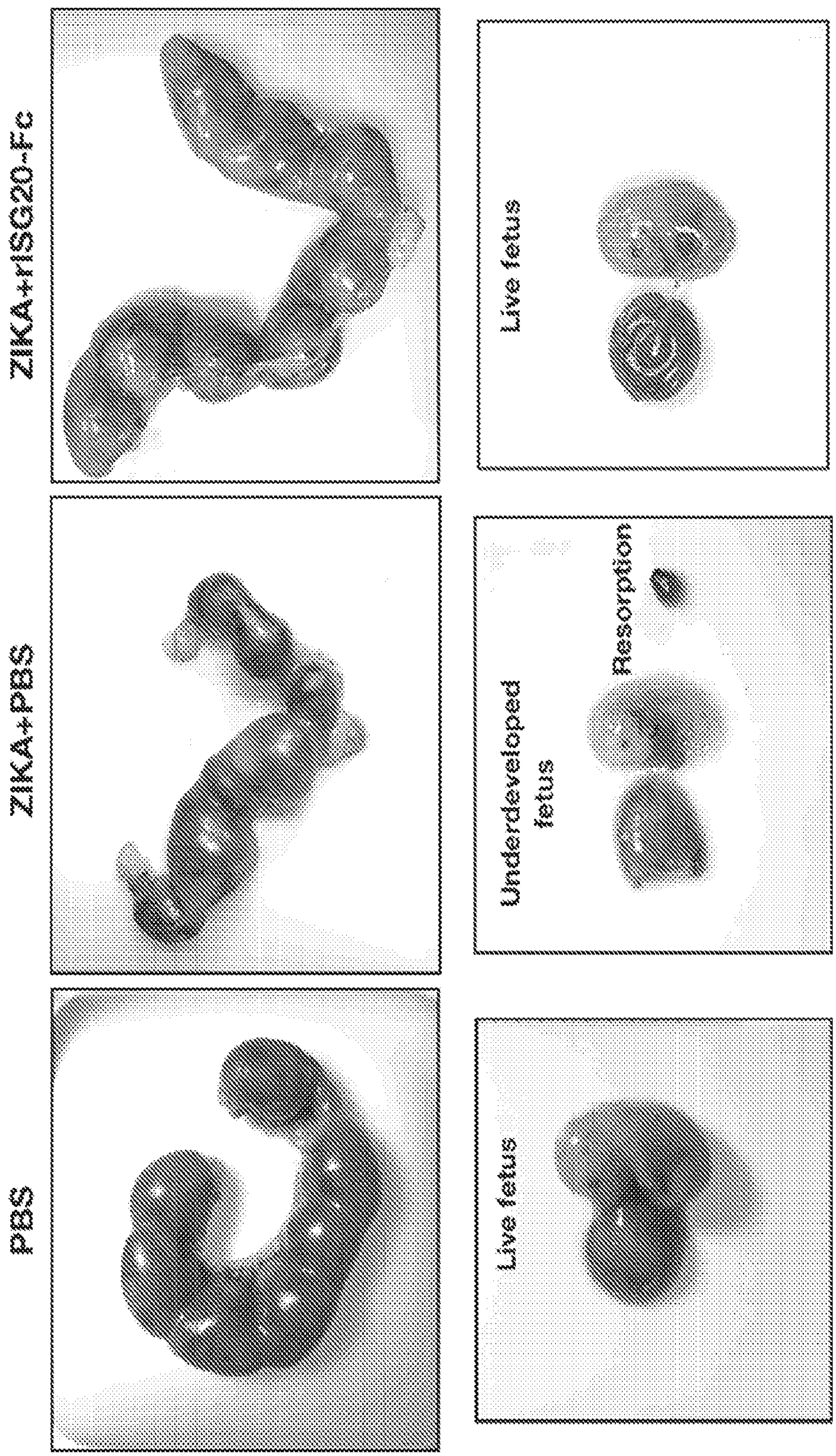
Figure 6C:
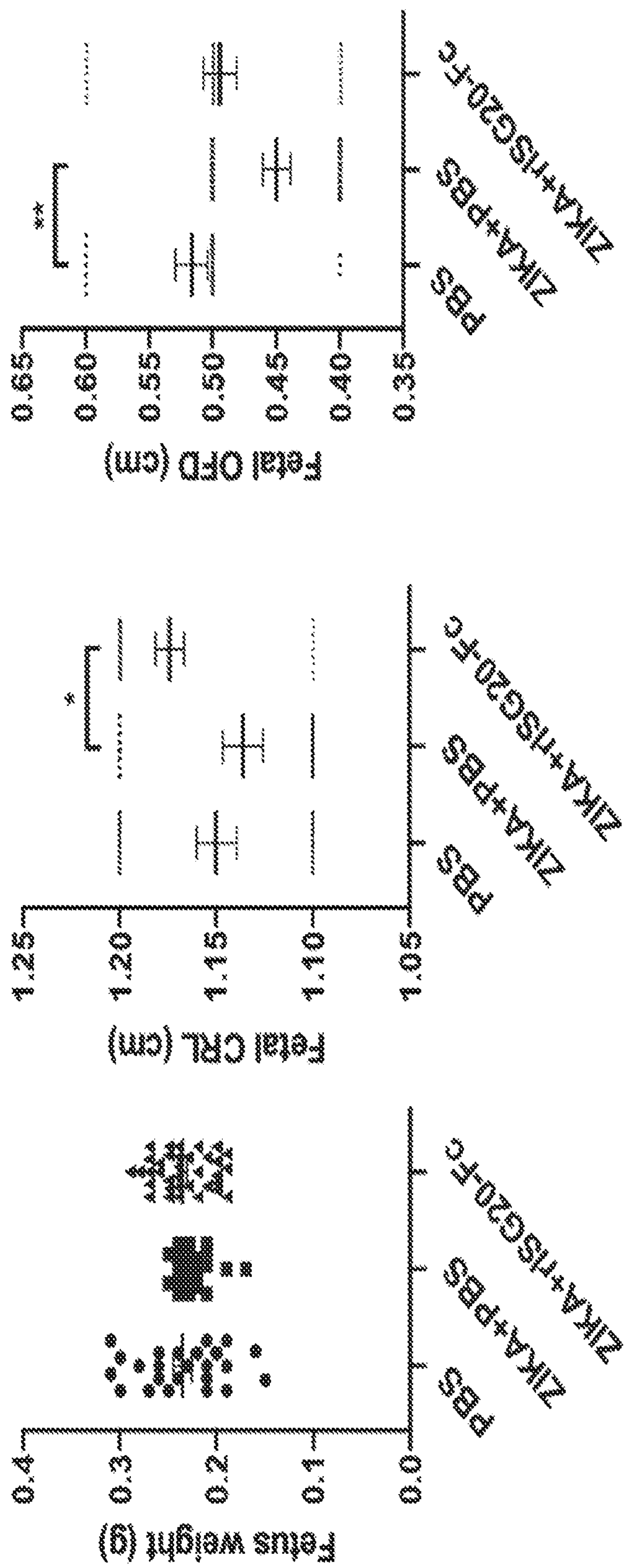
Figure 7A:
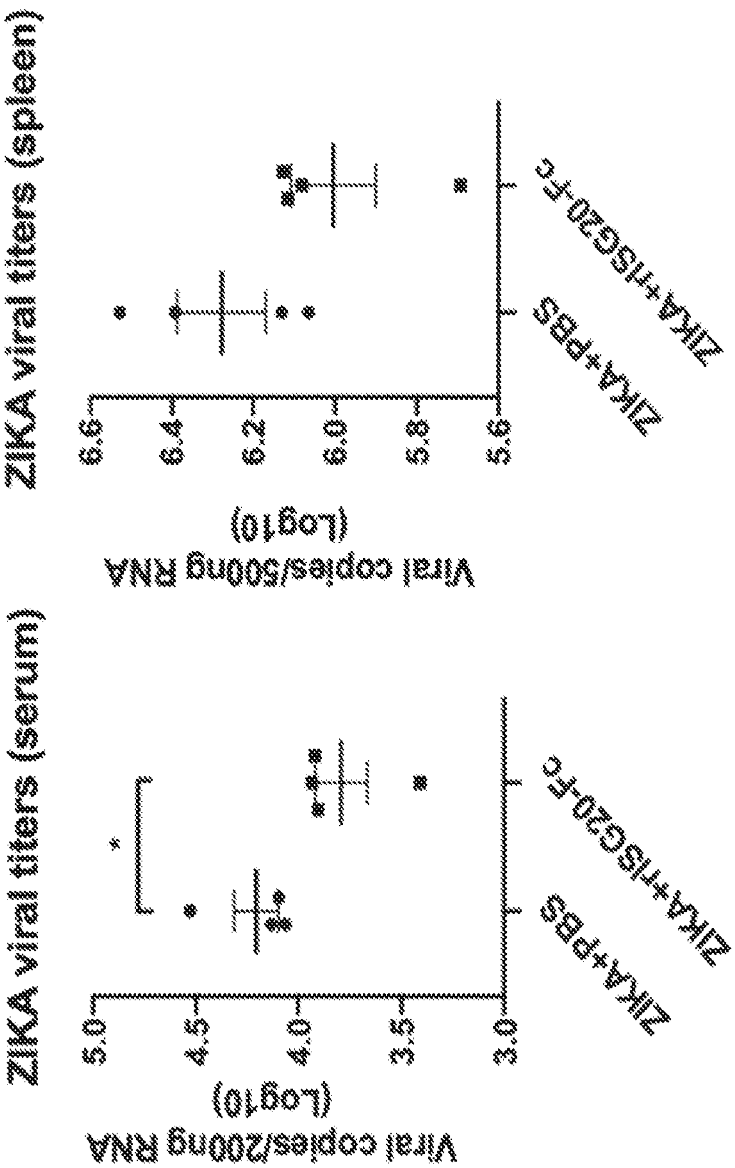
Figure 7B:
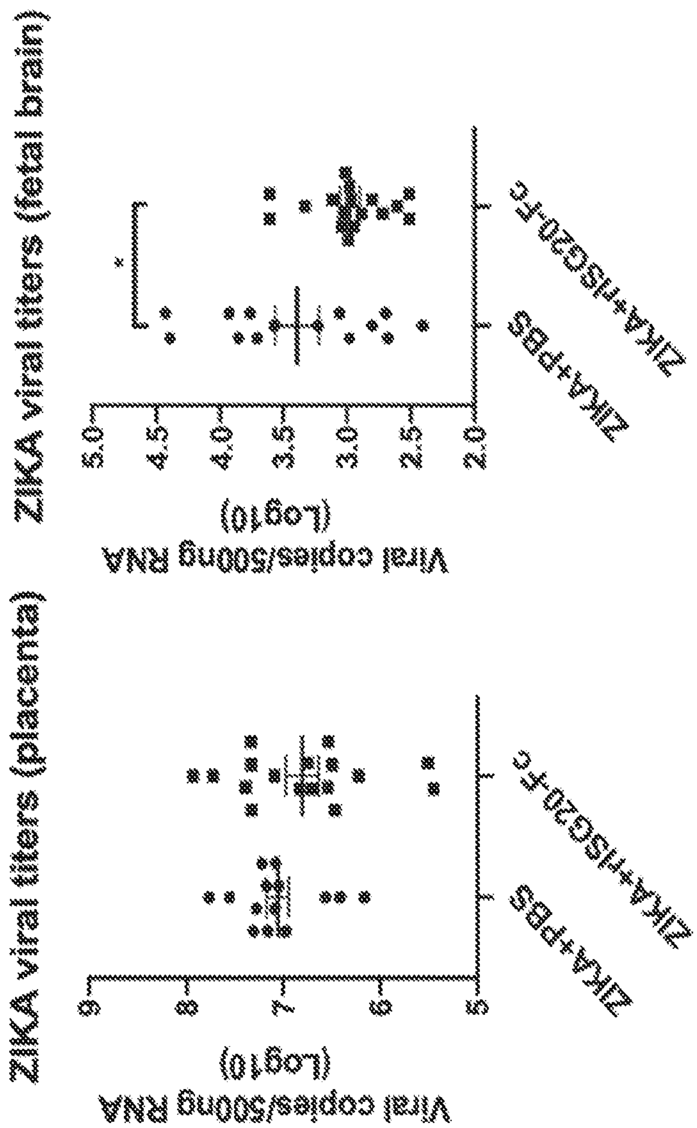
Figure 7C:
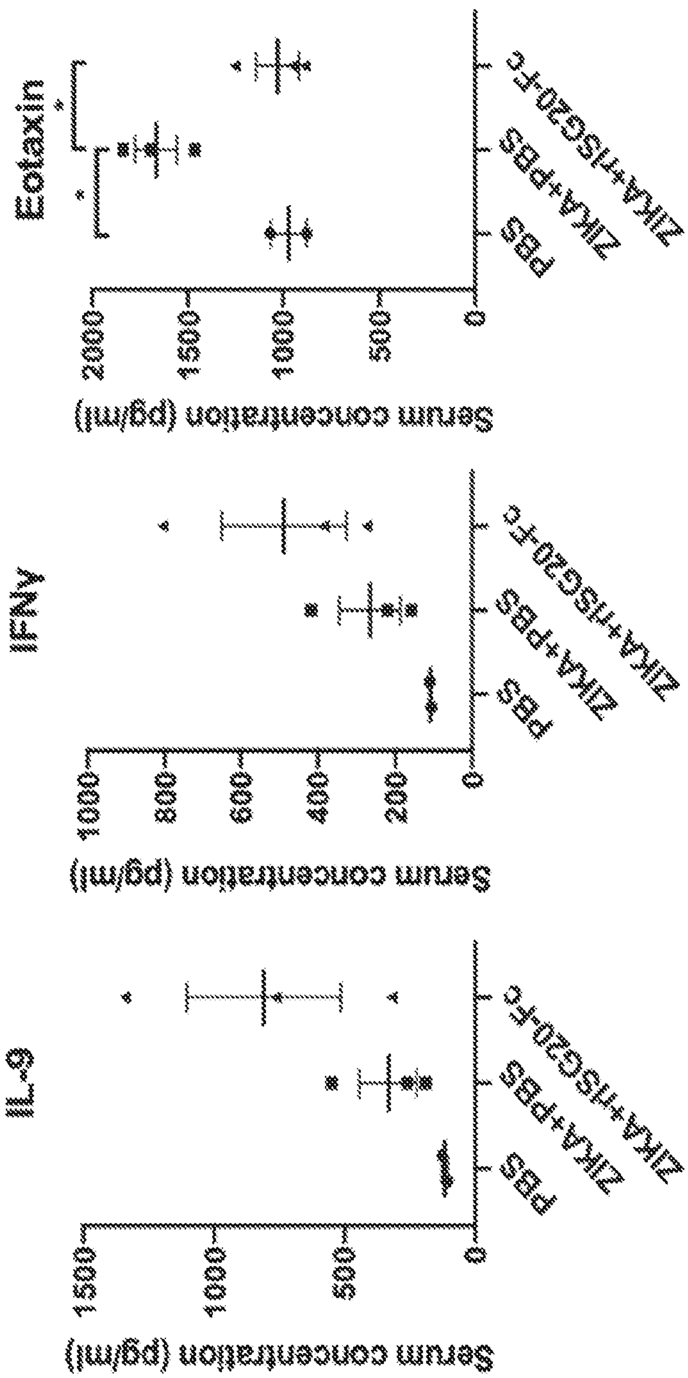
Figure 7D:
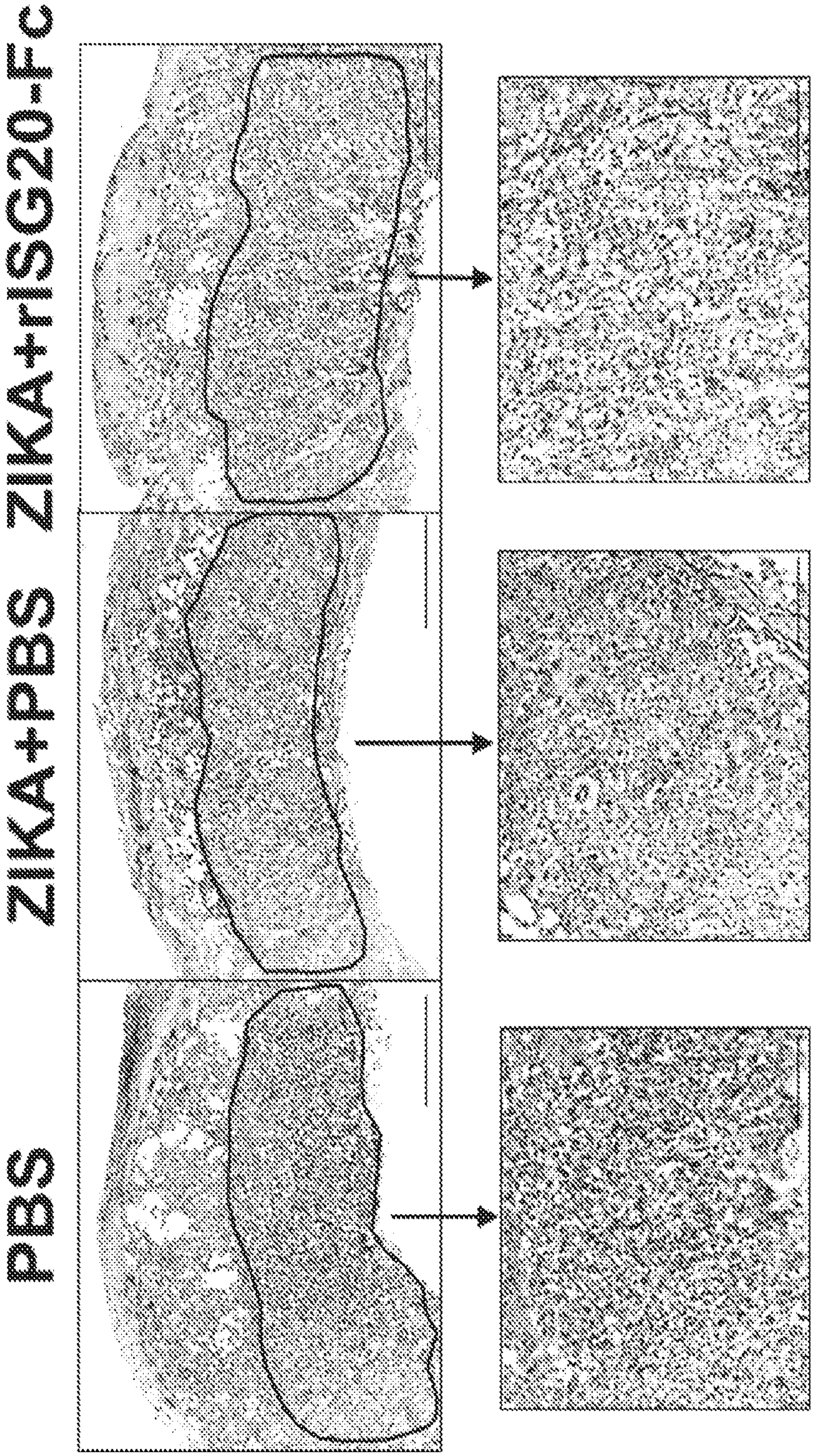
Figure 8A:
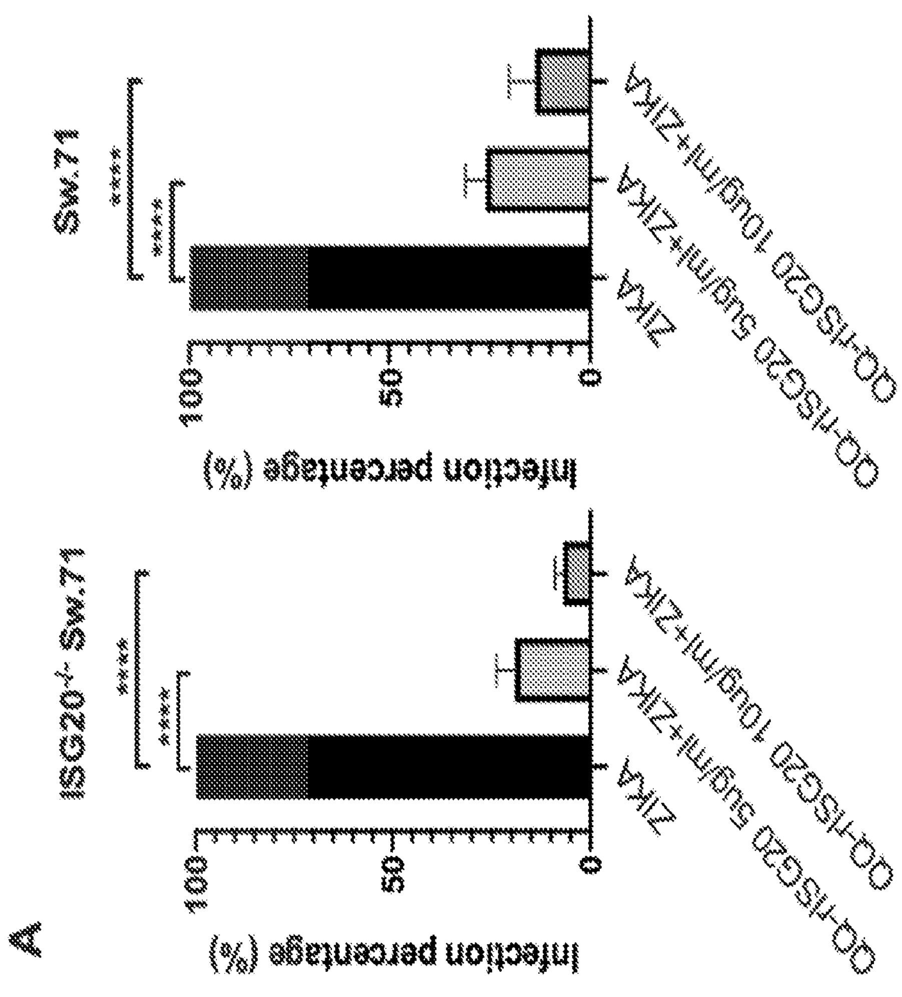
Figure 8B:
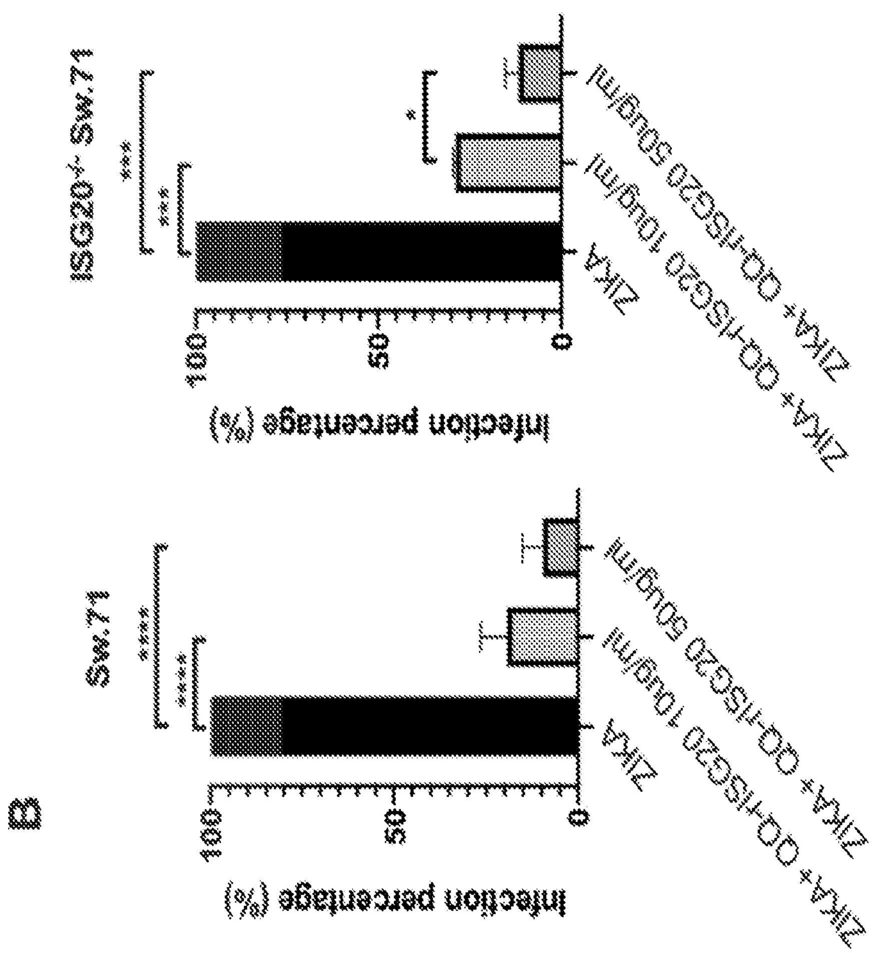
Figure 9:
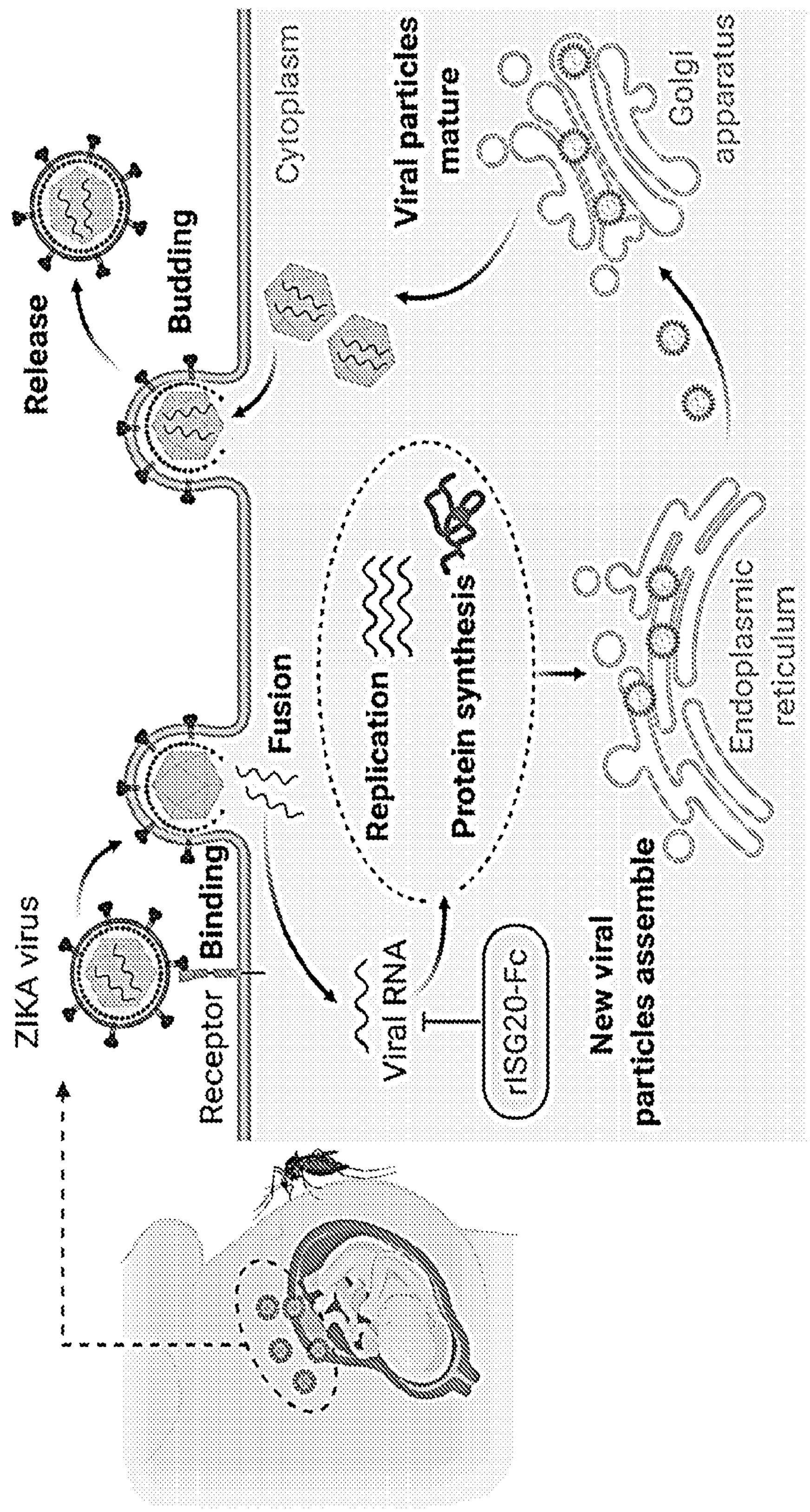
Figure 10:
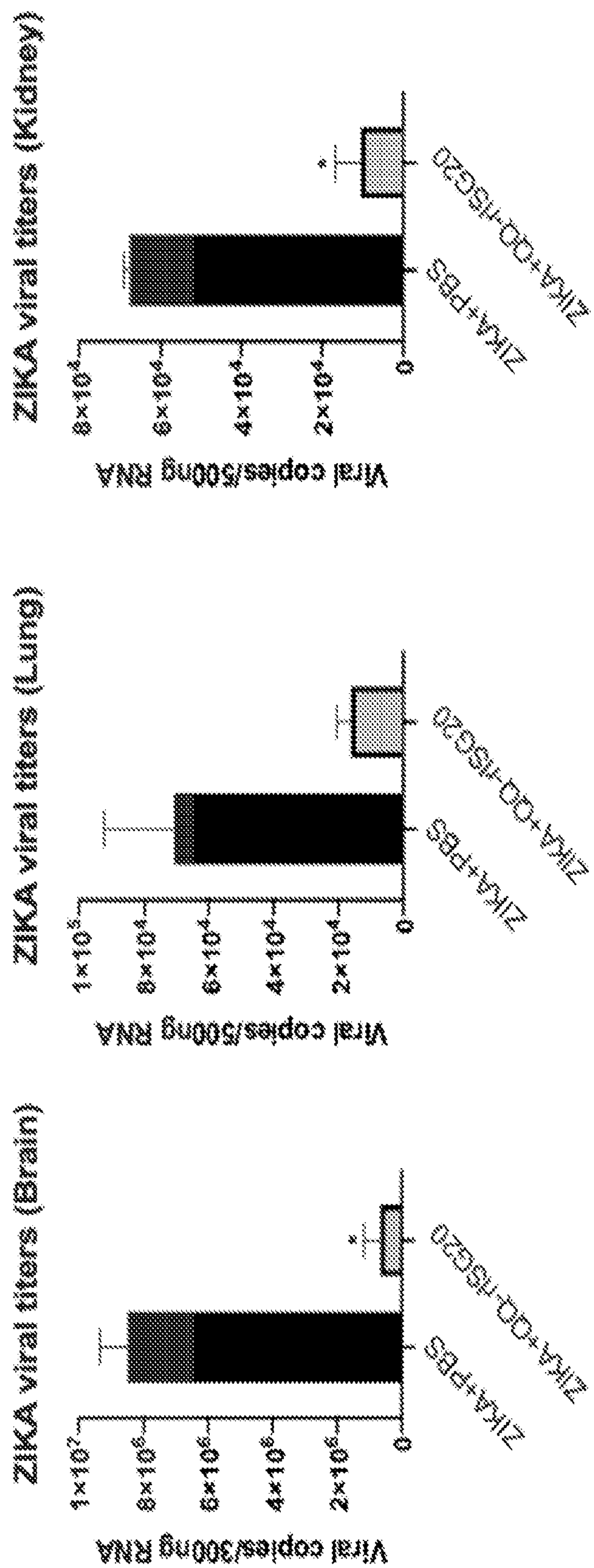
Figure 11:
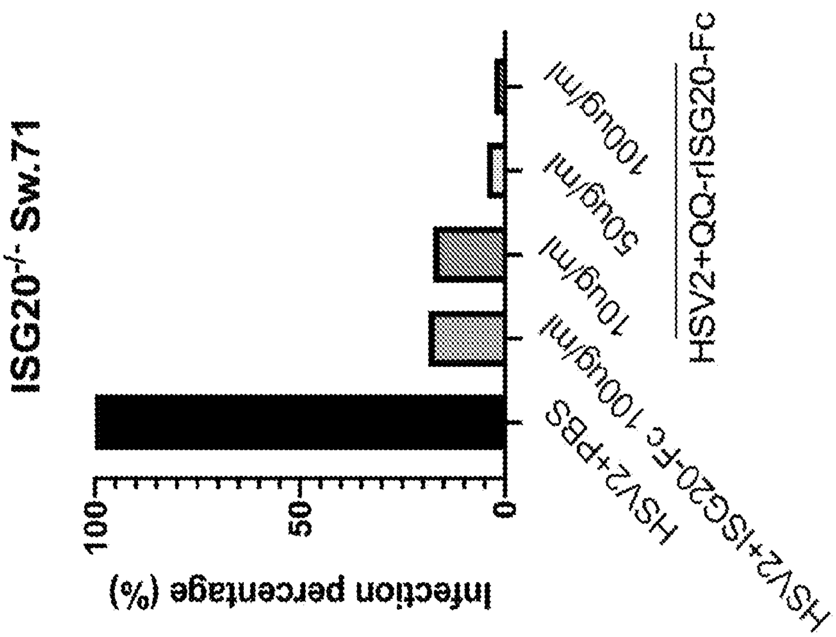
Figure 12:
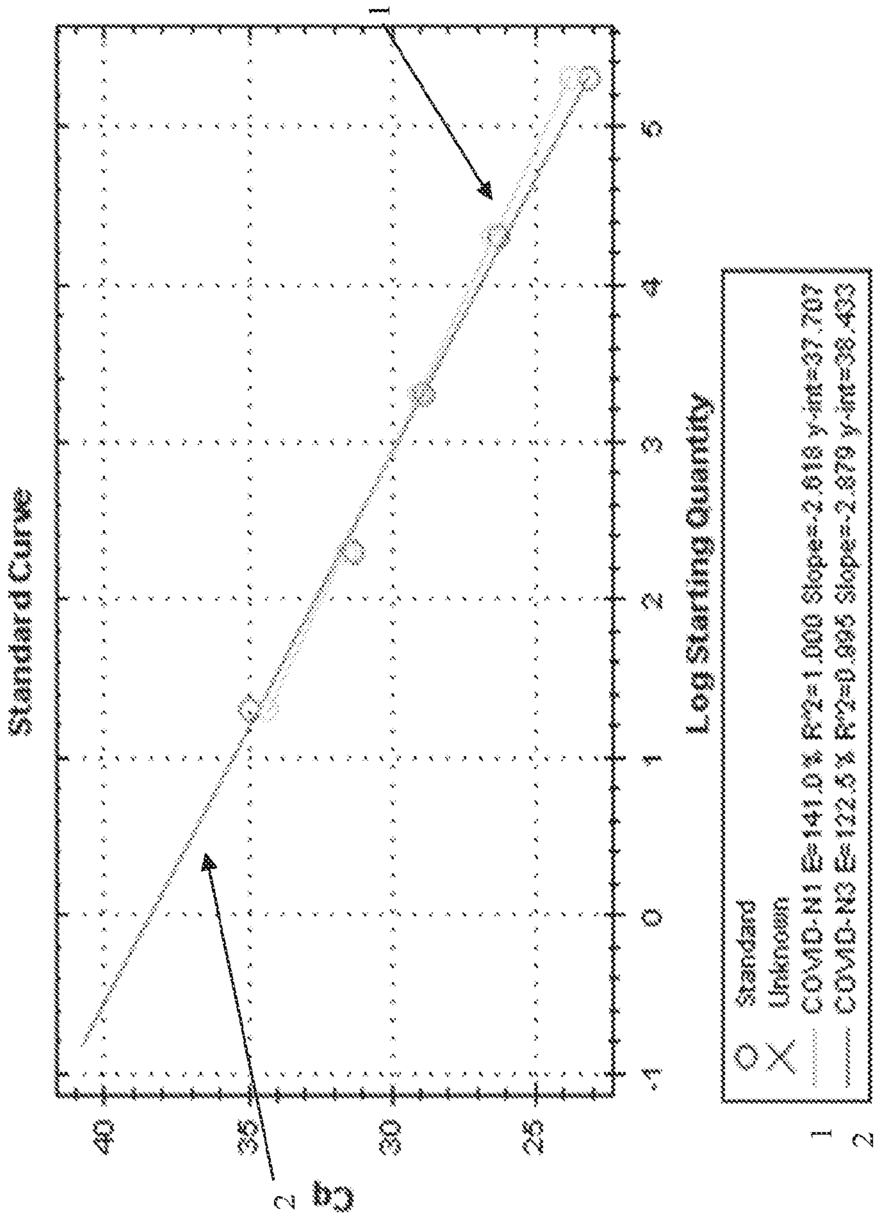
Figure 13:
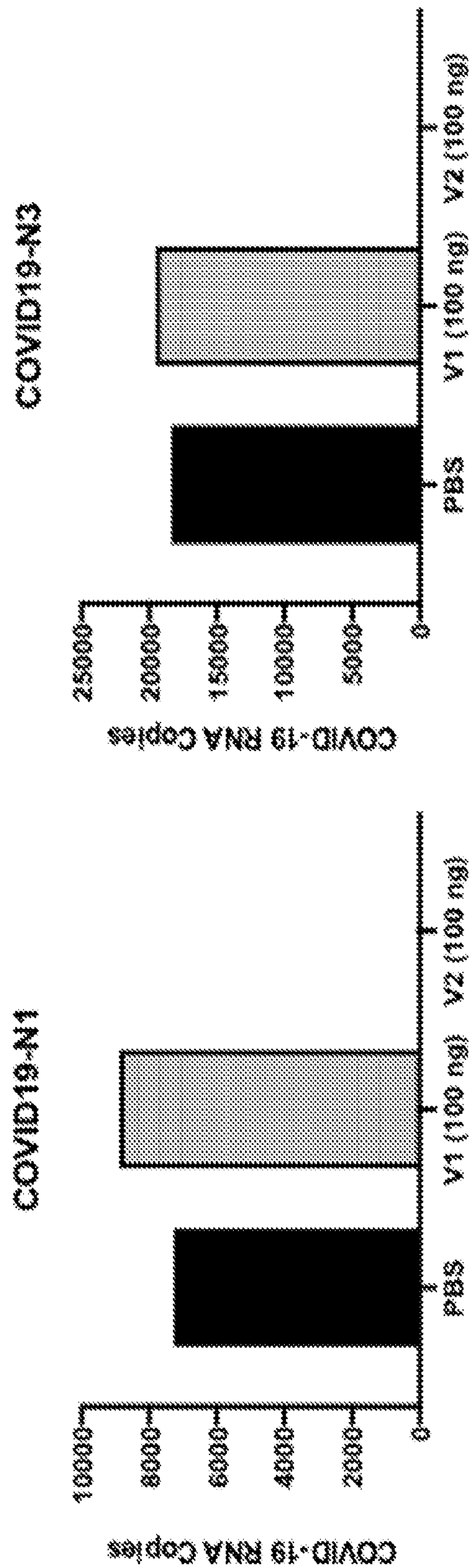
Figure 14:
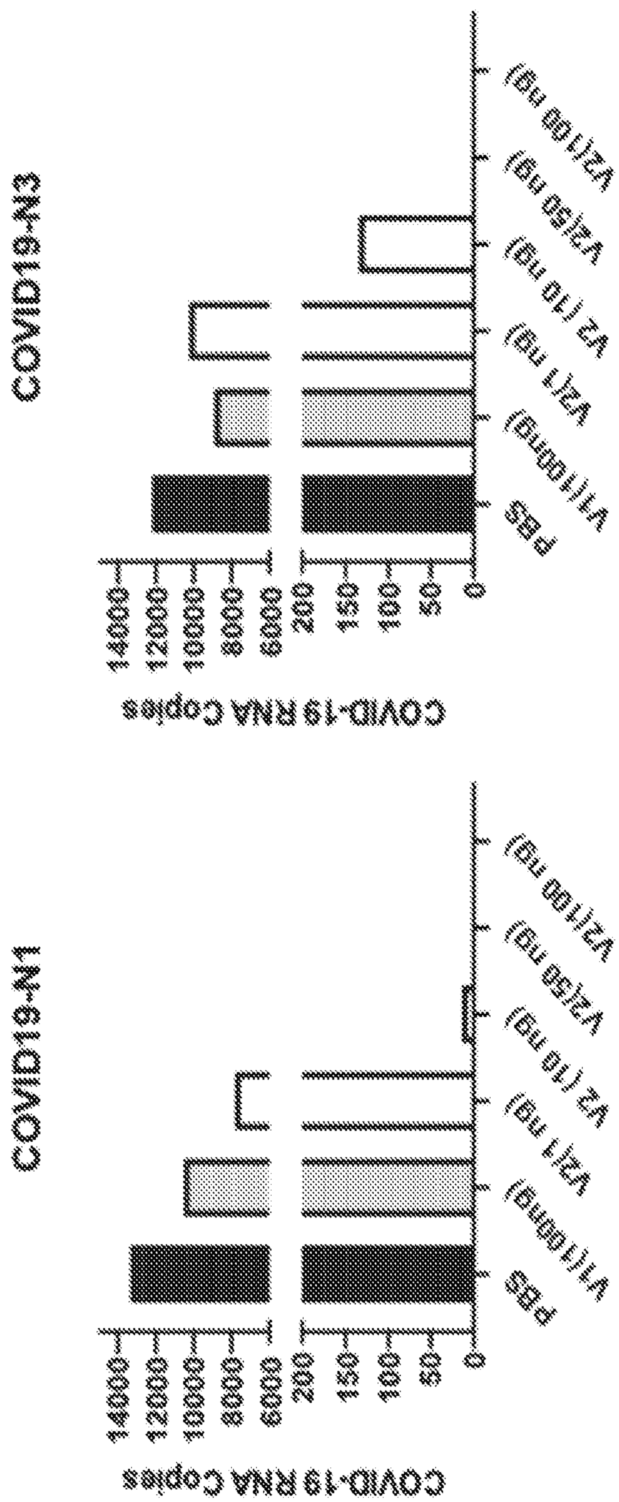
Figure 15A:
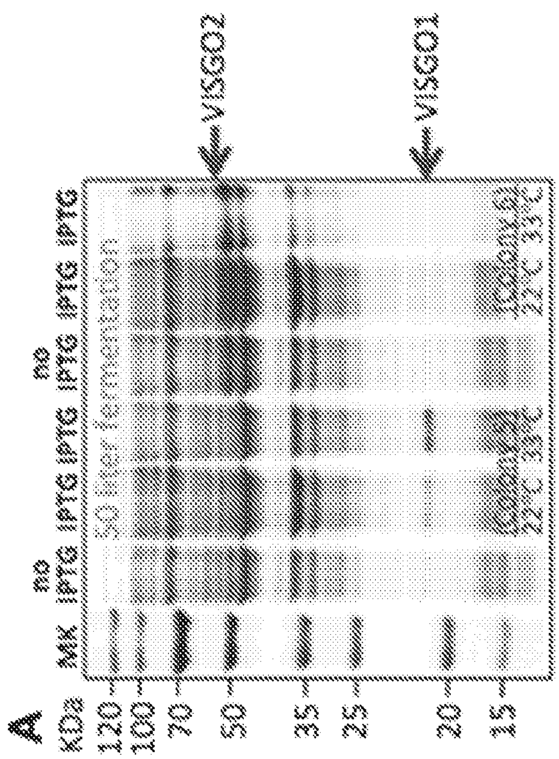
Figure 15B:
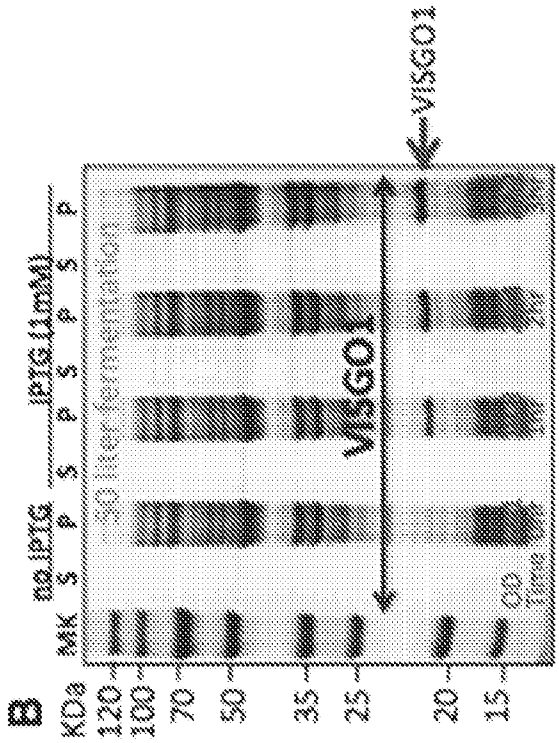
Figure 15F:
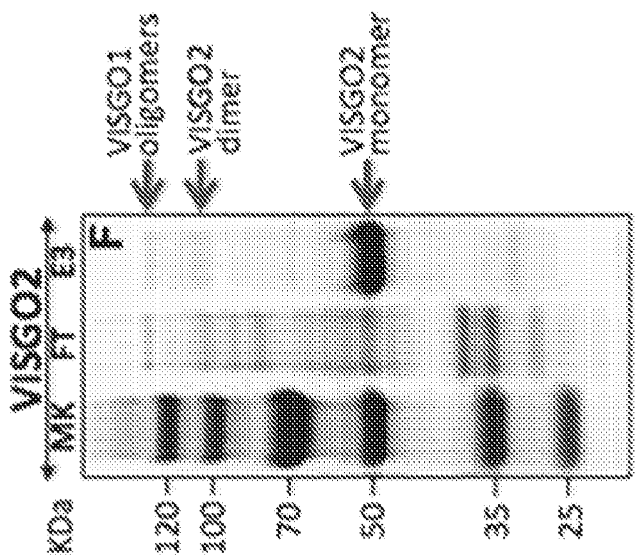
Figure 15C:
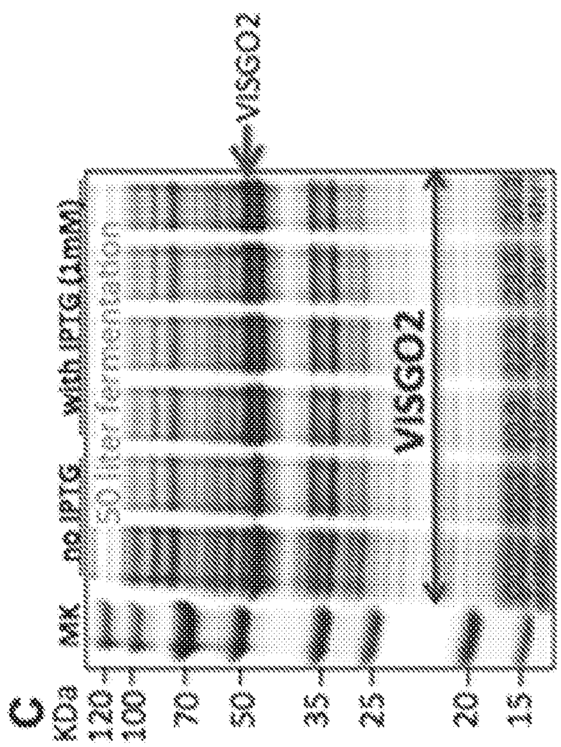
Figures 15D, 15E:
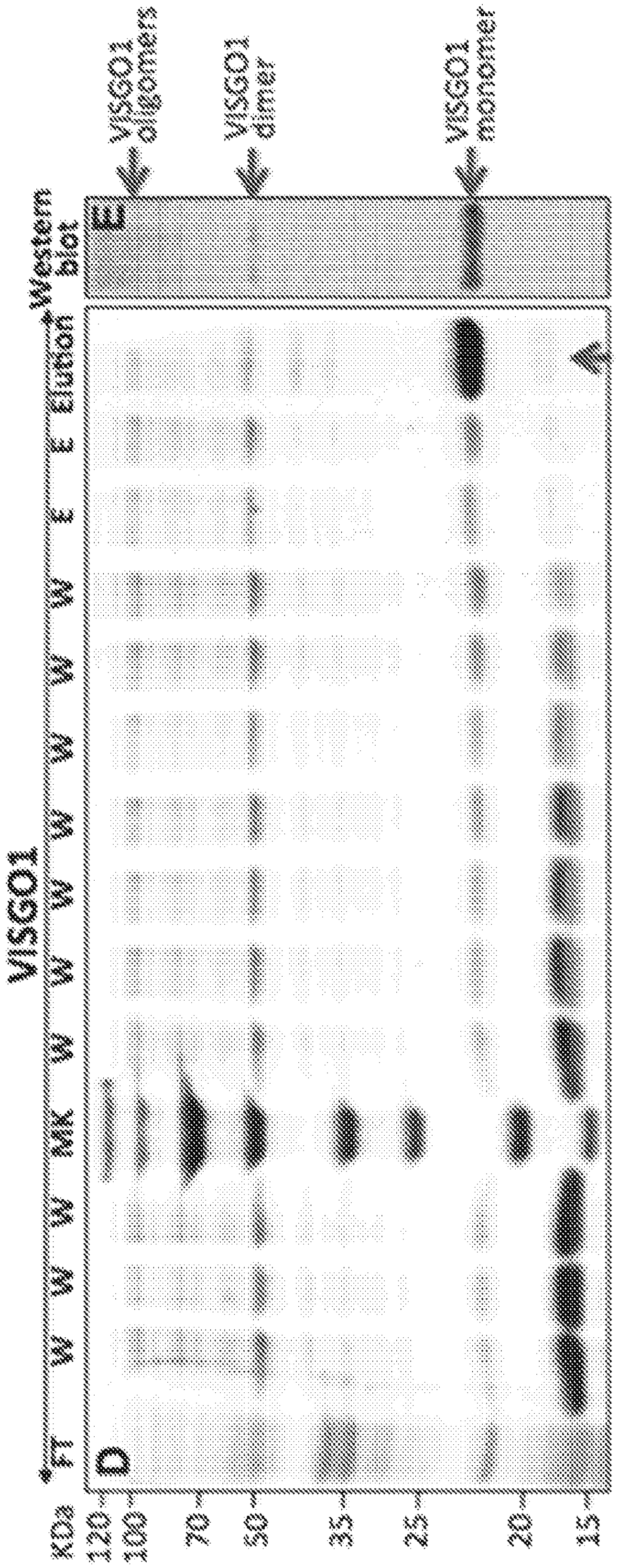

FIG. 2A shows two graphs illustrating results after Sw.71 and HPC cells were treated with different doses of IFNβ (3, 30, 300 ng/ml) for 8 hours and RNA were collected for determining ISG20 mRNA expressions by qRT-PCR; note the increase of ISG20 mRNA expression in a dose-dependent manner; *$p<0.05$, **$p<0.01$ by One-way ANOVA;

FIG. 2B shows two graphs illustrating results after Sw.71 and HPC cells were treated with 300 ng/ml IFNβ over time and RNA was collected for determining ISG20 mRNA expressions by qRT-PCR; note the increase of ISG20 mRNA expression in a time-dependent manner. *$p<0.05$ by One-way ANOVA;

FIG. 2C shows Western blots demonstrating results after Sw.71 and HPC cells were treated with different doses of IFNβ (3, 30, 300 ng/ml) for 24 hours and protein was collected for determining ISG20 protein expressions by western blot; note the increase of ISG20 protein expression in a dose-dependent manner;

FIG. 2D shows Western blots demonstrating results after Sw.71 and HPC cells were treated with 300 ng/ml IFNβ over time and protein was collected for determining ISG20 protein expressions by western blot; note that there was no ISG20 protein expression in the no treatment group in both Sw.71 and HPC, only after IFNβ treatment, ISG20 protein expression exhibited a time-dependent manner; data represent as mean±SEM from three independent experiments; β-actin served as a loading control for western blot;

FIGS. 3A, 3B, 3C, 3D, and 3E show that lack of ISG20 in trophoblast cells leads to more ZIKV replication and viral shedding;

FIG. 3A shows Western blots demonstrating that ISG20 protein expression was increased in ZIKV infection; Sw.71 cells were infected with ZIKV (MOI=2) over time, and proteins were collected for western blot analysis; β-actin served as a loading control;

FIG. 3B shows Western blots demonstrating no ISG20 protein expression in ISG20−/− Sw.71 in ZIKV infection; Sw.71 and ISG20−/− Sw.71 cells were infected with ZIKV (MOI=2) for 1 hour and refreshed with regular media for 48 hours, and proteins were collected for western blot analysis; β-actin served as a loading control;

FIG. 3C is a graph demonstrating that higher ZIKA titer was shown in ISG20−/− Sw.71 cells; Sw.71 and ISG20−/− Sw.71 cells were infected with ZIKV (MOI=2) for 1 hour and refreshed with regular media for 48 hours, and RNA was collected for determining the viral titer and gene expression by qRT-PCR. Data represent as mean±SEM from four independent experiments (each dot represents one independent experiment); *p<0.05 by Student's t-test;

FIG. 3D shows two images illustrating more viral shedding in ZIKV-infected ISG20−/− Sw.71 cell culture supernatant; supernatant from ZIKV-infected Sw.71 and ISG20−/− Sw.71 cells were collected and plaque assay was performed using Vero cells; a representative plaque assay picture is presented; note that more plaques were formed in Vero cells by incubating with ZIKV-infected ISG20−/− Sw.71 cell culture supernatant; scale bar=130 μm;

FIG. 3E is a graph showing results of counting and averaging plaques for the quantification of the viral titers; data represent as mean±SEM from three independent experiments; *p<0.05 by Student's t-test;

FIGS. 4A, 4B, 4C, and 4D show that lack of ISG20 in trophoblast cells weakens the protection provided by IFNβ against ZIKV infection;

FIG. 4A shows two graphs demonstrating induction of IFNβ mRNA in response to ZIKV infection in Sw.71 and ISG20−/− Sw.71 trophoblast cells; Sw.71 and ISG20−/− Sw.71 cells were infected with ZIKV (MOI=2) for 1 hour and refreshed with regular media for 48 hours, and RNA was collected for qRT-PCR; note that ISG20−/− Sw.71 cells shows IFNβ mRNA induction in response to ZIKV infection; data represent as mean±SEM from three or four independent experiments (each dot represents one independent experiment); *p<0.05, **p<0.01 by Student's t-test;

FIG. 4B shows two graphs demonstrating ISGs mRNA expression stimulated by IFNβ in Sw.71 and ISG20−/− Sw.71 trophoblast cells; Sw.71 and ISG20−/− Sw.71 cells were treated with 30 ng/ml IFNβ for 24 hours, and RNA was collected for determining the ISGs gene expression by qRT-PCR; note that less fold changes were shown in ISG20−/− Sw.71 cells after IFNβ treatment; data represent as mean±SEM from three independent experiments (each dot represents one independent experiment); *p<0.05, **p<0.01 by Student's t-test against control;

FIG. 4C shows Western blots illustrating no ISG20 protein expression in ISG20−/− Sw.71 cells after IFNβ treatment; Sw.71 and ISG20−/− Sw.71 cells were treated with 30 ng/ml IFNβ for 24 hours, and proteins were collected for western blot analysis; β-actin served as a loading control for western blot;

FIG. 4D is a graph showing that IFNβ pre-treatment significantly prevented trophoblast cells from ZIKV infection, however, this protection was evidently attenuated due to lack of ISG20. Sw.71 and ISG20−/− Sw.71 cells were pre-treated with or without 30 ng/ml IFNβ for 24 hours, followed by ZIKV infection (MOI=2) for 1 hour and refreshed with regular media for 24 hours, and RNA was collected to determine the viral titers by qRT-PCR; data represent as mean±SEM from four independent experiments (each dot represents one independent experiment); *p<0.05 by Student's t-test;

FIGS. 5A, 5B, 5C, 5D, and 5E illustrate the design and isolation of a recombinant ISG20 protein and characterization of the anti-viral effect of the isolated recombinant ISG20 protein;

FIG. 5A is a diagram showing the design of the recombinant ISG20-Fc protein; the components are: 1) ISG20 sequence; 2) Linker; 3) Fc domain of human $IgG_1$ (Fc); 4) Tev sequence, cleavage between Q and G; 5) Signal sequence (ENPP7); 6) His Tag;

FIG. 5B is a diagram showing the workflow used for clone production and selection;

FIG. 5C is a Western blot showing results of selection and verification of positive clones; in the positive clone, ISG20 protein expressed both in the cytosol (endogenous) and supernatant (secreted) compared to the non-transfected CHO cells and transfected negative clones. CHO, Chinese hamster ovary cell without transfection; β-actin served as a loading control;

FIG. 5D is a graph showing that ISG20 secretion in the positive clone supernatant significantly decreased ZIKV infection in trophoblast cells; Supernatants from negative and positive clones were collected and added to ISG20−/− Sw.71 trophoblast cells together with ZIKA virus (MOI=2) for 1 hour, followed by refreshing with new growth media for 48 hours; RNA was then collected to determine viral titers by qRT-PCR; data represent as mean±SEM from three independent experiments (each dot represents one independent experiment); **p<0.01 by Student's t-test;

FIG. 5E shows two graphs and corresponding agarose gels illustrating that recombinant ISG20-Fc degrades ZIKA viral RNA and HSV2 viral DNA; 50 ng purified viral RNA (ZIKV) or DNA (HSV-2) were incubated with increasing concentrations of rISG20-Fc (5, 50, 500 ng) in the presence of RNase inhibitor for 90 minutes at 37° C. followed by quantification of viral titers by qRT-PCR, and agarose gel was used to evaluate the RNA degradation by electrophoresis; the representative picture of agarose gel is presented; rISG20-Fc was able to degrade both ZIKV RNA and HSV-2 DNA in a dose dependent manner; however, rISG20-Fc was more efficient in degrading viral RNA than DNA; data represent as mean±SEM from three independent experiments (each dot represents one independent experiment); p<0.01. *p<0.001 and ****p<0.0001 by One-way ANOVA;

FIGS. 6A, 6B, and 6C show in vivo efficacy of rISG20-Fc improving pregnancy outcome in IFNAR1−/− pregnant mice during ZIKV infection;

FIG. 6A is a diagram showing a mouse experiment protocol used; adult (8-12 weeks of age) IFNAR1−/− pregnant mice were infected i.p. with 1*105 pfu ZIKV or 1% FBS DMEM/F12 media (vehicle) on embryo day 8.5 (E8.5); One hour after ZIKV/vehicle injection, treatment with rISG20-Fc (1 mg/kg) or PBS (control) was administered i.p. to the pregnant mice; on E9.5 and E10.5, the same protein/PBS injection was performed on the pregnant mice; on E14.5, the mice were sacrificed and organs were collected for viral titer quantification; N=3 for control PBS group, and n=4 for treatment groups;

FIG. 6B shows six images demonstrating results of macroscopic evaluation of the pregnant uterus and fetus; as shown, compared to the fetal death and reabsorptions in ZIKV-infected mice, rISG20-Fc treatment rescued this phenotype by decreasing pregnancy loss (resorption);

FIG. 6C shows three graphs demonstrating that rISG20-Fc treatment improves fetal development; measurement of fetal weight, crown-rump length (CRL) and occipitofrontal diameter (OFD) were evaluated when sacrificing mice on E14.5; ZIKV infection significantly inhibited fetal development, while rISG20-Fc treatment could significantly increase CRL; *p<0.05, **p<0.01 by One-way ANOVA;

FIGS. 7A, 7B, 7C, and 7D show in vivo efficacy of rISG20-Fc inhibiting ZIKA viral replication and promoting placental integrity in IFNAR1−/− pregnant mice;

FIG. 7A shows two graphs demonstrating that rISG20-Fc treatment alleviates maternal viral burden; note that rISG20-Fc treatment significantly decreased the maternal serum viral titers. N=3 mice for control PBS group, and n=4 mice for treatment groups; *p<0.05 by Student's t-test;

FIG. 7B shows two graphs demonstrating that rISG20-Fc treatment reduces ZIKV titers in the fetal brain; although there was no difference of ZIKV titer in the placenta, at the fetal side, there was a significant decrease of viral titer in the fetal brain, suggesting rISG20-Fc can block viral transmission from placenta to fetus; N=4 for each group, and 3-4 placentas/fetal brains from every mouse were analyzed; $*p<0.05$ by Student's t-test;

FIG. 7C shows three graphs demonstrating that rISG20-Fc treatment decreases Eotaxin significantly in maternal circulation; N=2 for PBS control group, and n=3 for every treatment group; $*p<0.05$ by One-way ANOVA;

FIG. 7D shows representative images of hematoxylin and eosin staining of the mouse placenta on E14.5 following the indicated treatments; labyrinth layers were marked with a solid line; note the major alteration on placenta structure characterized by multifocal loss of tissue architecture (necrosis) and the defective blood vessel formation of labyrinth in ZIKV+PBS group, and rISG20-Fc treatment improves vascularity and decreases decidual edema and cellular fragmentation at the labyrinth; Scale bar=580 μm (upper images); Scale bar=230 μm (bottom images);

FIG. 8A is a graph showing the antiviral effect of QQ-rISG20 on wild type Swan 71 and $ISG20^{-/-}$ Swan 71 pretreated with QQ-rISG20, followed by ZIKV (MOI=6) infection, viral titers were determined by qRT-PCR, $*p<0.05$, $***p<0.001$;

FIG. 8B the antiviral effect of QQ-rISG20 on wild type Swan 71 and $ISG20^{-/-}$ Swan 71 infected with ZIKV (MOI=6) first, then treated with QQ-rISG20, viral titers were determined by qRT-PCR, $*p<0.05$, $***p<0.001$;

FIG. 9 is a diagram of rISG20-Fc inhibiting ZIKA viral replication and decreasing viral infection in fetus; when ZIKA virus infects the pregnant woman, the virus will reach the placenta and transmit to the fetus; in the ZIKV replication cycle, it starts with the virus binding to host cell surface receptors, leading to endocytosis of the virus; internalized viral particles release the viral RNA into the cytoplasm of the host cell and start replication; during its replication, rISG20-Fc degrades ZIKV RNA and inhibits the subsequent transcription and translation; therefore, less new virus particles are released from the placenta to fetus;

FIG. 10 shows three graphs demonstrating results when female non-pregnant IFNAR1' mice were infected with ZIKV ($2*10^5$ pfu), and then QQ-ISG20(1 mg/kg) was administrated by i.p. injection once a day, for 4 days. At 7 days post-infection, mice were sacrificed and viral titers were determined by qRT-PCR in samples of from brain, lung and kidney ($*p<0.05$);

FIG. 11 is a graph which shows results of infection of $ISG20^{-/-}$ Swan 71 with HSV-2, followed by treatment with ISG20-Fc (100 μg/ml) or increasing concentrations of QQ-rISG20; viral titers were determined by qRT-PCR 48 hours post-infection; a 10-fold increase on the efficacy of ISG20 was found using QQ delivery system;

FIG. 12 is a graph which shows RT-PCR Standard Curves of N1 assay and N3 assay using the SARS-CoV-2 ("COVID-19") primers from CDC;

FIG. 13 shows two graphs demonstrating the effect of QQ-ISG20 (V2) on SARS-CoV-2 ("COVID-19") RNA copies; synthetic SARS-CoV-2 RNA is not detectable in samples incubated with QQ-ISG20 (V2); inactive ISG20 (V1) has no effect on SARS-CoV-2 RNA;

FIG. 14 shows two graphs demonstrating the effect of QQ-ISG20 (V2) on SARS-CoV-2 ("COVID-19") RNA copies; synthetic SARS-CoV-2 RNA is degraded in samples incubated with QQ-ISG20 (V2) in a dose dependent manner; inactive ISG20 (V1) has no effect on SARS-CoV-2 RNA as a control;

FIG. 15A is an image of SDS-PAGE of the VISGO expressions for both VISGO1 and VISGO2 at different temperature using a regular incubator shaker FIGS. 15B and 15C are images of SDS-PAGEs of 50-liter fermentation of the VISGO1 (FIG. 15B) and VISGO2 (FIG. 15C);

FIG. 15D is an image of SDS-PAGE of purification procedure of VISGO1, showing the purified VISGO1 protein in the elution lane highlighted with an upward-pointing arrow (W: washing buffer. E: Elution);

FIG. 15E is an image of a Western blot of the elution lane as in FIG. 15D; and FIG. 15F is an image of an SDS-PAGE of purified VISGO2 protein in E3 lane.

DETAILED DESCRIPTION OF THE INVENTION

Scientific and technical terms used herein are intended to have the meanings commonly understood by those of ordinary skill in the art. Such terms are found defined and used in context in various standard references illustratively including J. Sambrook and D.W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, PA, 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 9780470151808.

The singular terms "a," "an," and "the" are not intended to be limiting and include plural referents unless explicitly stated otherwise or the context clearly indicates otherwise.

Compositions and methods according to aspects of the present disclosure provide interferon-stimulated gene 20-kDa protein (ISG20) to treat a subject in need thereof.

The term "subject" refers to an individual in need of inhibition of pathogenic viral infection, including prevention and/or treatment of pathogenic viral infection, and generally includes mammals and birds, such as, but not limited to, humans, non-human primates, cats, dogs, sheep, cows, goats, horses, pigs, poultry, rabbits and rodents, such as rats, mice and guinea pigs. According to aspects of the present disclosure, the subject is human.

Compositions and methods according to aspects of the present disclosure provide for inhibition of pathogenic viral infection, including prevention and/or treatment of pathogenic viral infection, by introducing an ISG20 protein, or a variant thereof, into cells infected by a pathogenic virus or at risk of infection by a pathogenic virus, in vitro or in vivo.

According to aspects of the present disclosure, inhibiting a pathogenic virus includes contacting the ISG20 protein, or variant thereof, and viral nucleic acid of the pathogenic virus, in vitro or in vivo, results in at least partial degradation of the viral nucleic acid via the exonuclease activity of the ISG20 protein, or variant thereof.

According to aspects of the present disclosure, inhibiting a pathogenic virus includes introducing the ISG20 protein, or variant thereof, into a cell, in vitro or in vivo, whereby the ISG20 protein, or variant thereof, interrupts the viral life cycle in the cell.

According to aspects of the present disclosure, inhibiting a pathogenic virus includes introducing the ISG20 protein, or variant thereof, into a subject whereby the ISG20 protein, or variant thereof, modulates an immune response of the subject.

The term "ISG20 protein" as used herein refers to an interferon-stimulated gene 20-kDa protein (ISG20). ISG20 is a 181-amino acid protein of 20.4 kDa which is an RNA exonuclease and which also has some DNA exonuclease activity. The structure of ISG20 is well-known as described, for example, in Horio T. et al., Crystal structure of human ISG20, an interferon-induced antiviral ribonuclease. FEBS Letters. 2004; 577:111-116. An amino acid sequence for ISG20 protein is exemplified by the sequence shown herein as SEQ ID NO:1.

GenBank: CAG33223.1 ISG20 [*Homo sapiens*]

```
                                        (SEQ ID NO: 1)
MAGSREVVAMDCEMVGLGPHRESGLARCSLVNVHGAVLYDKFIRPEGEI

TDYRTRVSGVTPQHMVGATPFAVARLEILQLLKGKLVVGHDLKHDFQAL

KEDMSGYTIYDTSTDRLLWREAKLDHCRRVSLRVLSERLLHKSIQNSLL

GHSSVEDARATMELYQISQRIRARRGLPRLAVSD
```

GenBank: CR456942.1 ISG20 [*Homo sapiens*], ISG20 protein of SEQ ID NO:1 is encoded by SEQ ID NO:2.

```
                                        (SEQ ID NO: 2)
atggctgggagccgtgaggtggtggccatggactgcgagatggtggggc

tggggccccaccgggagagtggcctggctcgttgcagcctcgtgaacgt

ccacggtgctgtgctgtacgacaagttcatccggcctgagggagagatc

accgattacagaacccgggtcagcggggtcacccctcagcacatggtgg

gggccacaccatttgccgtggccaggctagagatcctgcagctcctgaa

aggcaagctggtggtgggtcatgacctgaagcacgacttccaggcactg

aaagaggacatgagcggctacacaatctacgacacgtccactgacaggc

tgttgtggcgtgaggccaagctggaccactgcaggcgtgtctccctgcg

ggtgctgagtgagcgcctcctgcacaagagcatccagaacagcctgctt

ggacacagctcggtggaagatgcgagggcaacgatggagctctatcaaa

tctcccagagaatccgagcccgccgagggctgccccgcctggctgtgtc

agattaa
```

An ISG20 protein, or variant thereof, used in methods of inhibiting a pathogenic virus according to aspects of the present disclosure is obtained by methods such as isolation, synthesis, or recombinant expression of a nucleic acid encoding the ISG20 protein. Such proteins may also be obtained commercially.

The term "nucleic acid" refers to RNA or DNA molecules having more than one nucleotide in any form including single-stranded, double-stranded, oligonucleotide or polynucleotide. The term "nucleotide sequence" refers to the ordering of nucleotides in an oligonucleotide or polynucleotide in a single-stranded form of nucleic acid.

The ISG20 protein, or variant thereof, included in compositions and methods according to aspects of the present disclosure is isolated or purified, and can be recombinantly produced.

Recombinant expression of an ISG20 protein, or variant thereof, includes expression of a nucleic acid encoding the protein wherein the nucleic acid is included in an expression construct.

A host cell may be transfected with the expression construct encoding the desired ISG20 protein, or variant thereof, such that the ISG20 protein, or variant thereof, is expressed in the cell.

The terms "expression construct" and "expression cassette" are used herein to refer to a double-stranded recombinant DNA molecule containing a desired nucleic acid coding sequence for ISG20 protein, or variant thereof, to be expressed and containing one or more regulatory elements necessary or desirable for the expression of the operably linked coding sequence.

Expression constructs operable to express a desired protein include, for example, in operable linkage: a promoter, a DNA sequence encoding a desired protein and a transcription termination site.

The term "regulatory element" as used herein refers to a nucleotide sequence which controls some aspect of the expression of nucleic acid sequences. Exemplary regulatory elements illustratively include an enhancer, an internal ribosome entry site (IRES), an intron; an origin of replication, a polyadenylation signal (polyA), a promoter, a transcription termination sequence, and an upstream regulatory domain, which contribute to the replication, transcription, post-transcriptional processing of a nucleic acid sequence. Those of ordinary skill in the art are capable of selecting and using these and other regulatory elements in an expression construct with no more than routine experimentation. Expression constructs can be generated recombinantly or synthetically using well-known methodology.

The terms "operably linked" and "in operable linkage" as used herein refer to a nucleic acid in functional relationship with a second nucleic acid.

A regulatory element included in an expression cassette is a promoter in particular aspects.

The term "promoter" is well-known in the art and refers to one or more DNA sequences operably linked to a nucleic acid sequence to be transcribed and which bind an RNA polymerase and allow for initiation of transcription. A promoter is typically positioned upstream (5') of a nucleic acid encoding a peptide or protein to be expressed.

An included promoter can be a constitutive promoter or can provide inducible expression. One of skill in the art is familiar with various well-known promoters and is able to select a promoter suitable for use in expressing a peptide or protein in a particular environment, such as in a specified cell type.

For expression in a yeast host cell, suitable promoters include, but are not limited to, an ADH1 promoter, a PGK1 promoter, an ENO promoter, a PYK1 promoter and the like; or a regulatable promoter such as a GAL1 promoter, a GAL 10 promoter, an ADH2 promoter, a PH05 promoter, a CUP1 promoter, a GAL7 promoter, a MET25 promoter, a MET3 promoter, a CYC1 promoter, a HIS 3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1.

For expression in a prokaryotic host cell include, suitable promoters include, but are not limited to, a bacteriophage T7 RNA polymerase promoter; a trp promoter; a lac operon promoter; a trc promoter; a tac promoter; an araBAD promoter; an ssaG promoter; a pagC promoter, a sigma70 promoter, a dps promoter, an spy promoter, an SPI-2 promoter; an actA promoter, an rps M promoter; a tetracycline promoter, an SP6 promoter, a bacteriophage T3 promoter, a gpt promoter and a bacteriophage lambda P promoter.

Additional suitable bacterial and eukaryotic promoters are well-known, for example as described in Sambrook et al., Molecular Cloning, A Laboratory Manual, 2nd ed. 1989; and 3rd ed., 2001; Kriegler, Gene Transfer and Expression: A Laboratory Manual (1990); and Ausubel et al., Current Protocols in Molecular Biology, 2014.

For expression in an eukaryotic cell, promoters that can be included in an expression construct include, but are not limited to, cytomegalovirus immediate early promoter; herpes simplex virus thymidine kinase promoter; early and late SV40 promoters; a phosphoglycerate kinase (PGK) promoter; a promoter present in long terminal repeats from a retrovirus; and a mouse metallothionein-I promoter, a beta-actin promoter, a ROSA26 promoter, a heat shock protein 70 (Hsp70) promoter, an EF-1 alpha gene encoding elongation factor 1 alpha (EF1) promoter, an eukaryotic initiation factor 4A (eIF-4A1) promoter, a chloramphenicol acetyltransferase (CAT) promoter and the long terminal repeat region of Rous Sarcoma virus (RSV promoter).

In addition to a promoter, one or more enhancer sequences may be included such as, but not limited to, cytomegalovirus (CMV) early enhancer element and an SV40 enhancer element.

Additional included sequences can be one or more of: an intron sequence such as the beta globin intron or a generic intron, a transcription termination sequence, and an mRNA polyadenylation (pA) sequence such as, but not limited to SV40-pA, beta-globin-pA and SCF-pA.

An expression construct may include sequences necessary for amplification in bacterial cells, such as a selection marker (e.g. kanamycin or ampicillin resistance gene) and a replicon. An Sh ble gene can be used to provide resistance to zeocin such that zeocin resistance can be used as a selection marker.

An internal ribosome entry site (IRES) is an optionally included nucleic acid sequence that permits translation initiation at an internal site in an mRNA. IRES are well-known in the art, for example as described in Pelletier, J. et al., Nature, 334:320-325, 1988; Vagner, S. et al., EMBO Rep., 2:893-898, 2001; and Hellen, C. U. et al, Genes Dev. 15:1593-1612, 2001.

The term "transcription termination site" refers to a DNA sequence operable to terminate transcription by an RNA polymerase. A transcription termination site is generally positioned downstream (3') of a nucleic acid encoding a peptide or protein to be expressed.

A leader sequence is optionally included in an expression construct.

Codon optimization of a nucleic acid encoding a desired protein may be used to improve expression in a particular expression system, for example by improving the efficiency of translation. A selected nucleic acid encoding a desired protein may be codon optimized for expression in any designated host cell, prokaryotic or eukaryotic, such as, but not limited to, bacteria, insect cells, yeast, fungus, bird eggs and mammalian cells.

An expressed protein optionally includes an N-terminal element such as a leader sequence and/or N-terminal methionine.

In addition to one or more nucleic acids encoding a desired ISG20 protein, or variant thereof, one or more nucleic acid sequences encoding additional proteins can be included in an expression vector such that expression produces two or more different proteins or a fusion protein.

For example, a nucleic acid sequence encoding a reporter, including, but not limited to, beta-galactosidase, green fluorescent protein and antibiotic resistance reporters is optionally included. In a further example, a his-tag, GST-tag or MBP-tag is optionally included.

Fusion proteins are provided according to aspects of the present disclosure which include ISG20 protein, or a variant thereof, covalently bound to a cell-targeting component functional to target the ISG20 to a cell, and/or to a specified cell type.

Fusion proteins are provided according to aspects of the present disclosure which include ISG20 protein, or a variant thereof, covalently bound to a cell-targeting component functional to target the ISG20 to a placental cell.

Fusion proteins are provided according to aspects of the present disclosure which include ISG20 protein, or a variant thereof, covalently bound to a cell-targeting component functional to target the ISG20 to a placental cell, wherein the cell-targeting component is an Fc domain of human $IgG_1$ which specifically binds to an Fc receptor of human placental cells.

A nucleic acid encoding an ISG20 protein, or variant thereof, can be cloned into an expression vector for transformation into prokaryotic or eukaryotic cells and expression of the encoded peptides and/or protein(s). As used herein, "expression vectors" are defined as polynucleotides which, when introduced into an appropriate host cell, an expression system, can be transcribed and translated, producing the encoded polypeptide(s).

Expression vectors are known in the art and include plasmids, cosmids, viruses and bacteriophages, for example. Expression vectors can be prokaryotic vectors, insect vectors, or eukaryotic vectors, for example. Particular viral vectors illustratively include those derived from adenovirus, adeno-associated virus and lentivirus.

For example, an expression construct including, in operable linkage: a promoter, a DNA sequence encoding a desired protein and a transcription termination site, is included in a plasmid, cosmid, virus, or bacteriophage expression vector.

Particular vectors are known in the art and one of skill in the art will recognize an appropriate vector for a specific purpose.

Any suitable expression vector/host cell system can be used for expression of ISG20 protein, or variant thereof, for administration to a subject according to aspects of the present disclosure.

Expression of an ISG20 protein, or variant thereof, using a recombinant expression vector is accomplished by introduction of the expression vector into an eukaryotic or prokaryotic host cell expression system such as an insect cell, mammalian cell, yeast cell, fungus, bird egg, bacterial cell or any other single or multicellular organism recognized in the art.

Host cells containing the recombinant expression vector are maintained under conditions wherein the desired protein is produced. Host cells may be cultured and maintained using known cell culture techniques such as described in Celis, Julio, ed., 1994, Cell Biology Laboratory Handbook, Academic Press, N.Y. Various culturing conditions for these cells, including media formulations with regard to specific nutrients, oxygen, tension, carbon dioxide and reduced serum levels, can be selected and optimized by one of skill in the art.

Bacterial cells can be used as the host cells to produce ISG20 protein, or variant thereof. Recombinant protein expression in bacterial cells and purification of the produced protein may be performed using known protocols, such as described in Paulina Balbas, Argelia Lorence ed., 2004, Recombinant Gene Expression: Reviews and Protocols, Humana Press, New Jersey; Peter E. Vaillancourt, 2003, *E. Coli* Gene Expression Protocols, Springer Science & Business Media.

Optionally, recombinantly produced ISG20 proteins and/or variants thereof are purified to remove endotoxin when an endotoxin producing host cell type is used. For example, an additional washing step can be added during protein purification stage using 10 column volume of 0.2% of Triton X114 to remove endotoxin from bacterially expressed recombinant ISG20 proteins.

Alternatively, in order to produce recombinant ISG20 proteins and/or variants thereof which do not trigger endotoxic response in human cells, a genetically modified bacterial strain, ClearColi™ BL21(DE3) can be used as host cells such that no endotoxin removal is required.

For expression in a host cell, any of the well-known procedures for introducing recombinant nucleic acids into host cells may be used, such as calcium phosphate transfection, polybrene, protoplast fusion, electroporation, sonoporation, liposomes and microinjection, examples of which are described in Sambrook et al., Molecular Cloning: A Laboratory Manual, Cold Spring Harbor Laboratory Press, 2001; and Ausubel, F. et al., (Eds.), Current Protocols in Molecular Biology, 2014.

A cell free expression system is optionally used to express an ISG20 protein, or variant thereof, such as described in Ausubel, F. et al., (Eds.), Current Protocols in Molecular Biology, 2014.

An expression construct can be administered to a cell in vivo for expression of the encoded protein or proteins in a subject. Thus, according to aspects of the present disclosure, methods of inhibiting a pathogenic virus as described herein include administered an expression construct encoding ISG20, or a variant thereof, to a subject in need thereof. An expression construct may be included in a vector for administration to a subject. Particular viral vectors that contain an expression construct encoding ISG20, or a variant thereof, illustratively include those derived from adenovirus, adeno-associated virus and lentivirus.

An expression construct encoding a fusion protein including ISG20, or a variant thereof, and a placental targeting component is administered to a cell in vivo for expression of the encoded protein or proteins in a pregnant subject having, or suspected of having a Zika virus infection, according to aspects of the present disclosure.

An expression construct encoding a fusion protein including ISG20, or a variant thereof, and an Fc domain of human $IgG_1$, or a variant thereof, is administered to a cell in vivo for expression of the encoded protein or proteins in a pregnant subject having, or suspected of having a Zika virus infection, according to aspects of the present disclosure ISG20 proteins shown herein as SEQ ID NO:1, and variants thereof, can be used in methods according to aspects described herein.

As used herein, the term "variant" refers to an ISG20 protein in which one or more amino acid residues have been modified by amino acid substitution, addition, or deletion, while retaining the function of a reference ISG20 protein. Variants of an ISG20 protein described herein are characterized by conserved functional properties compared to a corresponding reference ISG20 protein. As used herein, the term "variant" refers to an ISG20 protein in which one or more amino acid residues have been modified by amino acid substitution, addition, or deletion, while retaining the function of the ISG20 of SEQ ID NO:1. Variants of an ISG20 protein described herein are characterized by conserved functional properties compared to the ISG20 of SEQ ID NO:1.

A variant ISG20 is encoded by a nucleic acid in which one or more nucleotides have been modified by nucleotide substitution, addition, or deletion, e.g. compared to SEQ ID NO:2.

Mutations can be introduced using standard molecular biology techniques, such as chemical synthesis, site-directed mutagenesis and PCR-mediated mutagenesis to produce a variant.

One of skill in the art will recognize that one or more amino acid mutations can be introduced without altering the functional properties of a desired ISG20 protein, thereby producing an ISG20 variant. For example, one or more amino acid substitutions, additions, or deletions can be made without altering the functional properties of a desired ISG20 protein, thereby producing an ISG20 variant.

Biological activity of an ISG20 protein variant is readily determined by one of skill in the art, for instance using any of the functional assays described herein or other functional assays known in the art.

Variants of an ISG20 protein described herein are characterized by conserved functional properties compared to the corresponding ISG20 protein and have 75%, 80%, 85%, 90%, 95%, 96%, 97%, 98%, 99% or greater identity to the amino acid sequence of a reference ISG20 protein. According to aspects of the present disclosure, variants of an ISG20 protein described herein are characterized by conserved functional properties compared to the corresponding ISG20 protein and have 75%, 80%, 85%, 90%, 95%, 96%, 97%, 98%, 99% or greater identity to SEQ ID NO: 1.

When comparing a reference ISG20 protein to a variant, amino acid similarity may be considered in addition to identity of amino acids at corresponding positions in an amino acid sequence. "Amino acid similarity" refers to amino acid identity and conservative amino acid substitutions in a putative homologue compared to the corresponding amino acid positions in a reference protein.

Variants of an ISG20 protein described herein are characterized by conserved functional properties compared to the corresponding ISG20 protein and have 75%, 80%, 85%, 90%, 95%, 96%, 97%, 98%, 99% or greater similarity to the amino acid sequence of a reference ISG20 protein. According to aspects of the present disclosure, variants of an ISG20 protein described herein are characterized by conserved functional properties compared to the corresponding ISG20 protein and have 75%, 80%, 85%, 90%, 95%, 96%, 97%, 98%, 99% or greater similarity to SEQ ID NO:1.

Conservative amino acid substitutions can be made in reference proteins to produce variants. Thus, conservative amino acid substitutions can be made in SEQ ID NO:1 to produce ISG20 variants.

Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, proline, threonine, serine, valine, all typically considered to be small.

A variant can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

Percent identity or similarity is determined by comparison of amino acid or nucleic acid sequences, including a reference amino acid or nucleic acid sequence and a putative homologue amino acid or nucleic acid sequence. To determine the percent identity or similarity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). The two sequences compared are generally the same length or nearly the same length.

The determination of percent identity or similarity between two sequences can also be accomplished using a mathematical algorithm. Algorithms used for determination of percent identity or similarity illustratively include the algorithms of S. Karlin and S. Altshul, PNAS, 90:5873-5877, 1993; T. Smith and M. Waterman, Adv. Appl. Math. 2:482-489, 1981, S. Needleman and C. Wunsch, J. Mol. Biol., 48:443-453, 1970, W. Pearson and D. Lipman, PNAS, 85:2444-2448, 1988 and others incorporated into computerized implementations such as, but not limited to, GAP, BESTFIT, FASTA, TFASTA; and BLAST, for example incorporated in the Wisconsin Genetics Software Package, Genetics Computer Group, 575 Science Drive, Madison, Wis.) and publicly available from the National Center for Biotechnology Information.

A non-limiting example of a mathematical algorithm utilized for the comparison of two sequences is the algorithm of Karlin and Altschul, 1990, PNAS 87:2264-2268, modified as in Karlin and Altschul, 1993, PNAS. 90:5873-5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, word length=12 to obtain nucleotide sequences homologous to a nucleic acid molecules of the present disclosure. BLAST protein searches are performed with the XBLAST program parameters set, e.g., to score 50, word length=3 to obtain amino acid sequences homologous to a protein molecule of the present disclosure. To obtain gapped alignments for comparison purposes, Gapped BLAST are utilized as described in Altschul et al., 1997, Nucleic Acids Res. 25:3389-3402. Alternatively, PSI BLAST is used to perform an iterated search which detects distant relationships between molecules. When utilizing BLAST, Gapped BLAST, and PSI Blast programs, the default parameters of the respective programs (e.g., of XBLAST and NBLAST) are used. Another preferred, non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity or similarity between two sequences is determined using techniques similar to those described above, with or without allowing gaps. In calculating percent identity, typically only exact matches are counted.

As noted, the ISG20 protein shown herein as SEQ ID NO:1 is encoded by the nucleic acid sequence of SEQ ID NO:2. It is appreciated that due to the degenerate nature of the genetic code, alternate nucleic acid sequences encode a particular ISG20 protein, and that such alternate nucleic acids may be expressed to produce the desired ISG20 protein.

The term "complementary" refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA-5' is 100% complementary to a region of the nucleotide sequence 5'-TTAGCTGG-3'.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

An example of high stringency hybridization conditions is hybridization of nucleic acids over about 100 nucleotides in length in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL0.02% polyvinylpyrrolidone.

An ISG20 protein, or variant thereof, included in methods and/or compositions is an isolated protein according to aspects of the present disclosure.

An ISG20 protein, or variant thereof, modified by QQ is an isolated protein according to aspects of the present disclosure.

The term "isolated protein" indicates that the protein has been separated from biological materials, such as cells, cellular debris and other proteins, which may be present in the system in which the protein is produced. The term "isolated protein" may, but does not necessarily, indicate that the protein is purified.

Purified protein included in methods and compositions of the present disclosure contains least about 1-100% of the mass, by weight, such as about 25%, $50^{0}/a$, 75%, 85%, 95%, 99% or greater than about 99% of the mass, by weight, of the protein included.

Compositions

Compositions are provided according to aspects of the present disclosure including ISG20 protein, a variant of ISG20 protein, or both ISG20 protein, and a variant of ISG20 protein.

Compositions are provided according to aspects of the present disclosure including a nucleic acid molecule encoding ISG20 protein, a nucleic acid molecule encoding a variant of ISG20 protein, a nucleic acid molecule encoding both ISG20 protein, and a variant of ISG20 protein, or two or more thereof.

A pharmaceutically acceptable carrier is included in compositions according to aspects of the present disclosure.

Pharmaceutical compositions which include ISG20 protein, a variant of ISG20 protein, or both ISG20 protein, and a variant of ISG20 protein, along with a pharmaceutically acceptable carrier are provided according to aspects of the present disclosure.

Pharmaceutical compositions which include a nucleic acid molecule encoding ISG20 protein, a nucleic acid molecule encoding a variant of ISG20 protein, a nucleic acid molecule encoding both ISG20 protein, and a variant of ISG20 protein, or two or more thereof, along with a pharmaceutically acceptable carrier are provided according to aspects of the present disclosure.

The term "pharmaceutically acceptable carrier" as used herein refers to a carrier or diluent that is generally non-toxic to an intended recipient and which does not significantly inhibit activity of an active agent included with the pharmaceutically acceptable carrier in a pharmaceutical composition.

A pharmaceutical composition according to the present disclosure generally includes about 0.1-99% of an ISG20 protein or variant thereof, and a pharmaceutically acceptable carrier.

A pharmaceutical composition according to the present disclosure generally includes about 0.1-99% of a nucleic acid expression construct encoding ISG20 protein or a variant thereof.

Pharmaceutical compositions suitable for delivery to a subject may be prepared in various forms illustratively including physiologically acceptable sterile aqueous or non-aqueous solutions, dispersions, suspensions or emulsions, and sterile powders for reconstitution into sterile injectable solutions or dispersions.

Pharmaceutical compositions optionally include a buffer, a solvent, or a diluent.

Examples of suitable aqueous and nonaqueous carriers include water, ethanol, polyols such as propylene glycol, polyethylene glycol and glycerol; vegetable oils such as olive oil; and injectable organic esters such as ethyloleate; and suitable mixtures of any two or more thereof.

Such formulations are administered by a suitable route including parenteral administration. Optionally, administration includes systemic or local administration.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. One or more isotonic agents is optionally included, for example, sugars and or salts such as sodium chloride.

In particular aspects, a pharmaceutical composition including an ISG20 protein or variant thereof, or a nucleic acid expression construct encoding an ISG20 protein or variant thereof, is administered by topical application.

A topical formulation can be an ointment, lotion, cream or gel in particular aspects. Topical dosage forms such as ointment, lotion, cream or gel bases are described in Remington: The Science and Practice of Pharmacy, 21' Ed., Lippincott Williams & Wilkins, 2006, p. 880-882 and p. 886-888; and in Allen, L. V. et al., Ansel's Pharmaceutical Dosage Forms and Drug Delivery Systems, $8^{th}$ Ed., Lippincott Williams & Wilkins, 2005, p. 277-297.

Compositions including ISG20, a variant thereof, or a nucleic acid encoding ISG20, or a variant thereof, and a pharmaceutically acceptable carrier optionally include a lipid-based pharmaceutically acceptable carrier. The term "lipid-based carrier" refers to macromolecular structures having lipid and/or lipid derivatives as the major constituent.

Lipids included in lipid-based carriers can be naturally-occurring lipids, synthetic lipids or combinations thereof.

A lipid-based carrier is formulated as a liposome for use in compositions and methods according to aspects of the disclosure. Compositions including ISG20, a variant thereof, or a nucleic acid encoding ISG20, or a variant thereof, and a pharmaceutically acceptable carrier are provided according to aspects of the present disclosure wherein the pharmaceutically acceptable carrier includes liposomes.

The term "liposome" refers to a bilayer particle of amphipathic lipid molecules enclosing an aqueous interior space. Liposomes are typically produced as small unilammellar vesicles (SUVs), large unilammellar vesicles (LUVs) or multilammellar vesicles (MLVs). ISG20, a variant thereof, or a nucleic acid encoding ISG20, or a variant thereof, is associated with liposomes by encapsulation in the aqueous interior space of the liposomes, disposed in the lipid bilayer of the liposomes and/or associated with the liposomes by binding, such as ionic binding or association by van der Waals forces. Thus, ISG20, a variant thereof, or a nucleic acid encoding ISG20, or a variant thereof, is contained in liposomes when it is encapsulated in the aqueous interior space of the liposomes, disposed in the lipid bilayer of the liposomes and/or associated with the liposomes by binding, such as ionic binding or association by van der Waals forces. Liposomes according to aspects of the disclosure are generally in the range of about 1 nanometer-1 micron in diameter although they are not limited with regard to size.

Liposomal formulations of compositions according to aspects of the present disclosure include can include one or more types of neutral, cationic lipid and/or anionic lipid, such that the liposomal formulations have a net neutral surface charge at physiological pH. According to aspects, a PEG-modified lipid is included.

The term cationic lipid refers to any lipid which has a net positive charge at physiological pH. Examples of cationic lipids include, but are not limited to, N-(1-(2,3-dioleyloxy) propyl)-N,N,N-trimethylammonium chloride (DOTMA); 1,2-dioleoyloxy-3-(trimethylammonium)propane (DOTAP); 1,2-dioleoyl-3-dimethylammonium-propane (DODAP); dioctadecylamidoglycylspermine (DOGS); 1,2-dipalmitoylphosphatidylethanolamidospermine (DPPES); 2,3-dioleyloxy-N-(2-(sperminecarboxamido)ethyl)-N,N-dimethyl-1-propanaminium trifluoroacetate (DOSPA); dimyristoyltrimethylammonium propane (DMTAP); (3-dimyristyloxypropylxdimethylxhydroxyethyl)ammonium (DMRIE); dioctadecyldimethylammonium chloride (DODAC), Dimethyldidodecylammonium bromide (DDAB); 3p[N—(N,N'-dimethylaminoethane)-carbamoyl] cholesterol (DC-Chol); 1-[2-(9(Z)-octadecenoyloxy)-ethyl]-2-(8(Z)-heptadecenyl)-3-(2-hydroxyethyl)-imidazolinium (DOTIM); bis-guanidinium-spermidine-cholesterol (BGTC); bis-guanidinium-tren-cholesterol (BGTC); 1,3-Dioleoyloxy-2-(6-carboxy-spermyl)-propylamid (DOSPER) N-[3-[2-(1,3-dioleoyloxy)propoxy-carbonyl]propyl]-N,N, N-trimethylammonium iodide (YKS-220); as well as pharmaceutically acceptable salts and mixtures thereof. Additional examples of cationic lipids are described in Lasic and Papahadjopoulos, Medical Applications of Liposomes, Elsevier, 1998; U.S. Pat. Nos. 4,897,355; 5,208,036; 5,264,618; 5,279,833; 5,283,185; 5,334,761; 5,459,127; 5,736,392; 5,753,613; 5,785,992; 6,376,248; 6,586,410; 6,733,777; and 7,145,039.

The term neutral lipid refers to any lipid which has no net charge, either uncharged or in neutral charge zwitterionic form, at physiological pH. Examples of neutral lipids include, but are not limited to, L-alpha-phosphatidylcholine (ePC), distearoylphosphatidylcholine (DSPC), dioleoylphosphatidylethanolamine (DOPE), distearoylphosphatidylethanolamine (DSPE); 1,2-dioleoyl-sn-glycero-3-Phosphocholine (DOPC), 1,2-dipalmitoyl-sn-glycero-3-phosphoethanolamine (DPPE), cephalin, ceramide, cerebrosides, cholesterol, diacylglycerols, and sphingomyelin.

The term anionic lipid refers to any lipid which has a net negative charge at physiological pH. Examples of anionic lipids include, but are not limited to, dihexadecylphosphate (DhP), phosphatidyl inositols, phosphatidyl serines, such as dimyristoyl phosphatidyl serine, and dipalmitoyl phosphatidyl serine, phosphatidyl glycerols, such as dimyristoylphosphatidyl glycerol, dioleoylphosphatidyl glycerol, dilauryloylphosphatidyl glycerol, dipalmitoylphosphatidyl glycerol, distearyloylphosphatidyl glycerol, phosphatidic acids, such as dimyristoyl phosphatic acid and dipalmitoyl phosphatic acid and diphosphatidyl glycerol.

The term "modified lipid" refers to lipids modified to aid in, for example, inhibiting aggregation and/or precipitation, inhibiting immune response and/or improving half-life in circulation in vivo. Modified lipids include, but are not limited to, pegylated lipids, such as polyethyleneglycol 2000 distearoylphosphatidylethanolamine (PEG(2000) DSPE); 1,2-dipalmitoyl-sn-glycero-3-phosphoethanolamine-N-[methoxy(polyethylene glycol)-2000](DPPE-PEG-2000), and polyethyleneglycol 750 octadecylsphingosine (PEG (750) C8).

In addition to containing ISG20, a variant thereof, or a nucleic acid encoding ISG20, or a variant thereof, liposomes of the disclosure optionally contain any of a variety of useful biologically active molecules and substances including, but not limited to, adjunct therapeutics, proteins, peptides, carbohydrates, oligosaccharides, drugs, and nucleic acids capable of being complexed with the liposomes. The term "biologically active molecules and substances" refers molecules or substances that exert a biological effect in vitro and/or in vivo, such as, but not limited to, nucleic acids, inhibitory RNA, siRNA, shRNA, ribozymes, antisense nucleic acids, antibodies, hormones, small molecules, aptamers, decoy molecules and toxins.

According to aspects of the present disclosure, liposomes of the disclosure include a cell-targeting component effective to direct the liposomes to cells. According to aspects of the present disclosure, liposomes of the disclosure include a cell-targeting component effective to direct the liposomes to a specified cell type.

Liposomes are generated using well-known standard methods, including, but not limited to, solvent/hydration methods, ethanol or ether injection methods, freeze/thaw methods, sonication methods, reverse-phase evaporation methods, and surfactant methods. Liposomes and methods relating to their preparation and use are found in Liposomes: A Practical Approach (The Practical Approach Series, 264), V. P. Torchilin and V. Weissig (Eds.), Oxford University Press; 2nd ed., 2003; N. Duzgunes, Liposomes, Part A, Volume 367 (Methods in Enzymology) Academic Press; 1st ed., 2003; L. V. Allen, Jr. et al., Ansel's Pharmaceutical Dosage Forms and Drug Delivery Systems, 8th Ed., Philadelphia, PA: Lippincott, Williams & Wilkins, 2005, pp. 663-666; and A. R. Gennaro, Remington: The Science and Practice of Pharmacy, Lippincott Williams & Wilkins, 21st ed., 2005, pp. 766-767.

Pharmaceutically acceptable carriers and formulation of pharmaceutical compositions are known in the art, illustratively including, but not limited to, as described in Remington: The Science and Practice of Pharmacy, $21^{st}$ Ed., Lippincott, Williams & Wilkins, Philadelphia, PA, 2006; and Allen, L. V. et al., Ansel's Pharmaceutical Dosage Forms and Drug Delivery Systems, $8^{th}$ Ed., Lippincott, Williams & Wilkins, Philadelphia, PA, 2005.

A pharmaceutical composition including an ISG20 protein or variant thereof, or a nucleic acid expression construct encoding an ISG20 protein or variant thereof, is suitable for administration to a subject by a variety of systemic and/or local routes including, but not limited to, parenteral, oral, rectal, nasal, pulmonary, epidural, ocular, otic, intraarterial, intracardiac, intracerebroventricular, intracranial, intradermal, intravenous, intramuscular, intraperitoneal, intraosseous, intrathecal, intravesical, subcutaneous, topical, transdermal, and transmucosal, such as by sublingual, buccal, vaginal, and inhalational routes of administration.

Cell-Targeting Component

According to aspects of the present disclosure, a cell-targeting component is included in a pharmaceutical composition.

A cell-targeting component included in a pharmaceutical composition according to aspects of the present disclosure may be covalently bonded or non-covalently bonded to ISG20, a variant thereof, or a nucleic acid encoding ISG20, or a variant thereof.

A cell-targeting component can be covalently bonded to the amino acid terminus or carboxy terminus of a protein or peptide cargo, or a 5' or 3' terminus of a nucleic acid cargo, directly or indirectly.

A cell-targeting component can be indirectly covalently bonded to a cargo molecule via a linker.

According to aspects of the present disclosure, a cell-targeting component is directly or indirectly covalently bonded to a cargo molecule by co-expression from an expression construct as a fusion protein.

According to aspects of the present disclosure, an included cell-targeting component includes a "protein transduction domain" and the ISG20, a variant thereof, or a nucleic acid encoding ISG20, or a variant thereof is covalently bonded or non-covalently bonded to the "protein transduction domain."

The term "protein transduction domain" can be a protein, peptide, nucleic acid, carbohydrate, organic compound or inorganic compound which promotes delivery of an attached cargo molecule, ISG20, a variant thereof, or a nucleic acid encoding ISG20, or a variant thereof, across a cell membrane or organelle membrane into a cell or organelle.

A protein transduction domain can be covalently bonded to the amino acid terminus or carboxy terminus of a protein or peptide cargo, or a 5' or 3' terminus of a nucleic acid cargo, directly or indirectly.

A protein transduction domain can be indirectly covalently bonded to a cargo molecule via a linker.

A protein transduction domain can be a "cell penetrating peptide," typically 3 to 50 amino acids in length, which promotes delivery of ISG20, a variant thereof, or a nucleic acid encoding ISG20, or a variant thereof, into a cell. Cell penetrating peptides are polycationic, amphipathic, or hydrophobic, and mediate uptake of a cargo which is covalently or non-covalently bonded, into cells. In one configuration a cell penetrating peptide contains a number of basic amino acid residues, such as 3, 4, 5, 6, 7, 8, 9, 10, or more basic amino acids, sufficient to promote delivery of a covalently or non-covalently bonded attached ISG20, a variant thereof, or a nucleic acid encoding ISG20, or a variant thereof, into a cell. In one configuration a cell penetrating peptide is a polyarginine homopolymer or polylysine homopolymer, containing 3, 4, 5, 6, 7, 8, 9, 10, or more arginines or lysines, sufficient to promote delivery of a covalently or non-covalently bonded attached ISG20, a variant thereof, or a nucleic acid encoding ISG20, or a variant thereof, into a cell. Cell penetrating peptides include penetratin peptide, HIV-Tat, transportan, truncated human calcitonin peptide, a VP22 protein transduction domain, and *Drosophila* antennapedia protein transduction domain, see for example Matsushita et al., J. Mol. Med., 83(5):324-328, 2005. MPG and Pep are cell penetrating peptides which promote delivery of a non-covalently attached cargo into cells, see for example, Simeoin et al., Nucl. Acids Res, 31(11):2717-2724, 2003; and Deshayes et al., Adv. Drug Deliv. Rev., 60(4-5):537-547, 2008.

A protein transduction domain can be covalently bonded to a cargo by a cleavable linker, such as a disulfide linkage, according to aspects of the present disclosure.

Compositions are provided according to aspects of the present disclosure which include a protein transduction reagent-modified ISG20 protein. The protein transduction reagent includes a cation reagent and a lipid.

A "protein transduction reagent-modified ISG20 protein" is a ISG20 protein that has been treated with the protein transduction reagent, also termed a "QQ reagent" herein. The term "protein transduction reagent" refers to a composition effective to enable an ISG20 protein non-covalently bound to the protein transduction reagent to be delivered into mammalian cells and once present in mammalian cells, to dissociate from the protein to allow proper delivery of the protein to its proper subcellular location. The protein transduction reagent, also termed a "QQ reagent" herein, includes at least one cation reagent, at least one lipid, and optionally an enhancer. The term "QQ modified ISG20 protein" and grammatical variants thereof as used herein is equivalent to "protein transduction reagent-modified ISG20 protein" and grammatical variants thereof as used herein. Similarly, one or more proteins termed "QQ" protein signifies that the proteins is modified by treatment with a protein transduction reagent and is a "protein transduction reagent-modified ISG20 protein. For example, the term "QQ-ISG20" refers to ISG20 protein modified by treatment with a protein transduction reagent as described herein to produce protein transduction reagent-modified ISG20 protein.

One example of an appropriate cation reagent included in a protein transduction reagent of the present disclosure is polyethylenimine (PEI), such as, but not limited to, PEI Mw 1,200 (PEI 1.2K), PEI Mw 2000 (PEI 2K), PEI Mw 4000 (PEI 4K) and PEI Mw 8000 (PEI 8K).

A lipid included in a protein transduction reagent of the present disclosure can be any lipid known to those of skill in the art to have the same general properties as those listed herein. Examples of such lipids include, but are not limited to, DOTMA (N-1(-(2,3-dioleyloxy)propyl-N,N,N-trimethylammonium chloride; DOGS (dioctadecylamido-glycylspermine); DOTAP, 1,2-dioleoyl-3-trimethylammonium-propane; DOPE, 1,2-dioleoyl-sn-glycero-3-phosphoethanolamine; POPC, 1-palmitoyl-2-oleoyl-sn-glycero-3-phosphocholine; and DMPE 1,2-dimyristoyl-sn-glycero-3-phosphocholine.

Optionally, the protein transduction reagent includes polyethylenimine as a cation reagent and the lipid is DOTAP or DOTMA and DOPE or DOGS; POPC and DMPE; or DOTAP or DOTMA, DOPE or DOGS, POPC and DMPE. Optionally, the protein transduction reagent is QQ1a, QQ2a, QQ3a, QQ4a, QQ5a, QQ6a, QQ7a, QQ8a, QQ9a as described in Table 1 hereinbelow.

The optional enhancer included in a protein transduction reagent of the present disclosure can be any enhancer that significantly enhances cell loading of cationized proteins. Examples of such enhancers in cell cultures include, but are not limited to MG132, protease inhibitor, $CaCl_2$), DMSO and growth factors. Other enhancers can also be used, including, but not limited to, cell membrane surfactants. The protein transduction reagent can also include stabilizers and other inert carriers that do not affect the function of the protein transduction reagent. As shown in Table 1, the concentrations and specific compounds utilized can vary.

Pharmaceutical compositions which include a protein transduction reagent-modified ISG20 protein and/or protein transduction reagent-modified ISG20 protein variant are provided according to aspects of the present disclosure.

Pharmaceutical compositions are provided according to aspects of the present disclosure which include a QQ-modified ISG20 protein and/or a QQ-modified ISG20 protein variant.

Pharmaceutical compositions are provided according to aspects of the present disclosure which include a QQ-modified ISG20 protein and/or a QQ-modified ISG20 protein variant with the proviso that no nucleic acid encoding the ISG20 protein or variant thereof is included in the pharmaceutical composition.

Compositions and methods according to aspects of the present disclosure provide for inhibition of pathogenic viral infection, including prevention or treatment of pathogenic viral infection, by introducing a QQ-modified ISG20 protein or variant thereof into cells infected or at risk of infection by the pathogenic virus in vitro or in vivo. According to particular aspects of the present disclosure, introducing a QQ-modified ISG20 protein or variant thereof into cells infected or at risk of infection by the pathogenic virus in vitro or in vivo is achieved without introduction of a nucleic acid encoding the ISG20 protein or variant thereof.

Compositions and methods according to aspects of the present disclosure provide for inhibition of pathogenic viral infection, such as preventing or treating pathogenic viral infection, by introducing a QQ-modified ISG20 protein or variant thereof into cells infected or at risk for infection by a pathogenic virus, in vitro or in vivo, and without introduction of a nucleic acid encoding the ISG20 protein or variant thereof. According to particular aspects of the present disclosure, introducing a QQ-modified ISG20 protein or variant thereof into cells infected or at risk of infection by the pathogenic virus in vitro or in vivo is achieved without introduction of a nucleic acid encoding the ISG20 protein or variant thereof.

According to aspects of the present disclosure, an included cell-targeting component includes a target binding molecule, the target binding molecule capable of specific binding to a corresponding target.

The term "target binding molecule" refers to a protein, peptide, nucleic acid, carbohydrate, organic compound, or inorganic compound, or combination of any two or more thereof, capable of specific binding to a corresponding target, thereby promoting delivery of an attached cargo molecule, ISG20, a variant thereof, or a nucleic acid encoding ISG20, or a variant thereof, to a cell which contains a target of the target binding molecule.

The term "specific binding" refers to measureable and reproducible specific interaction between a target binding molecule and its corresponding target. Non-limiting examples of target binding molecule/target specific binding pairs include, antibody/antigen, antibody fragment/antigen, antibody/hapten, antibody fragment/hapten, aptamer/target, ligand/ligand receptor.

An included target binding molecule according to aspects of the present disclosure is or includes an antibody, an antibody fragment, an aptamer, a cytokine, or a receptor ligand.

According to aspects of the present disclosure, the cell-targeting component is a receptor ligand selected from the group consisting of: a bone morphogenetic protein (BMP), brain-derived neurotrophic factor (BDNF), epidermal growth factor (EGF), angiopoietin, fibroblast growth factor (FGF), glial cell line-derived neurotrophic factor (GDNF), granulocyte colony-stimulating factor (G-CSF), granulocyte macrophage colony-stimulating factor (GM-CSF), hepatocyte growth factor (HGF), hepatoma-derived growth factor (HDGF), insulin-like growth factor (IGF), an interferon (IFN), an interleukin, IL-1, IL-2, IL-3, IL-4, IL-5, IL-6, IL-7, keratinocyte growth factor (KGF), nerve growth factor (NGF), platelet-derived growth factor (PDGF), transforming growth factor alpha (TGF-alpha), transforming growth factor beta (TGF-beta), tumor necrosis factor alpha (TNF-alpha), and vascular endothelial growth factor (VEGF).

According to aspects of the present disclosure, the cell-targeting component is an Fc domain of human $IgG_1$ which specifically binds to an Fc receptor of placental cells.

The term "Fc domain of human $IgG_1$" as used herein refers to an Fc domain of human neonatal IgG1 that functions to increase fusion protein stability and facilitate the uptake by cells to which it specifically binds. The presence of the Fc domain of human neonatal IgG1, abbreviated "Fc" herein, in a fusion protein with ISG20 allows the binding of the recombinant protein to trophoblast cells and facilitate its transport from the maternal circulation into the fetal tissues for inhibition of viral infection.

An amino acid sequence for Fc protein is exemplified by the sequence shown herein as SEQ ID NO:15.

330 amino acid Fc portion of human IgG (Immunoglobulin heavy constant gamma 1, UniProtKB—P01857 (IGHG1_HUMAN)—full-length) SEQ ID NO:15

```
ASTKGPSVFPLAPSSKSTSGGTAALGCLVKDYFPEPVTVSWNSGALTSG
VHTFPAVLQSSGLYSLSSVVTVPSSSLGTQTYICNVNHKPSNTKVDKKV
EPKSCDKTHTCPPCPAPELLGGPSVFLFPPKPKDTLMISRTPEVTCVVV
DVSHEDPEVKFNWYVDGVEVHNAKTKPREEQYNSTYRVVSVLTVLHQDW
LNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLT
VDKSRWQQGNVFSCSVMHEALHNHYTQKSLSLSPGK
```

An Fc protein, or variant thereof, is included in compositions and methods according to aspects of the present disclosure.

An Fc protein variant included in compositions and methods according to aspects of the present disclosure is a fragment of full-length Fc, effective to target a fusion protein in which it is included to placental cells for inhibition of a virus.

An Fc protein variant included in compositions and methods according to aspects of the present disclosure is or includes:

```
                                        (SEQ ID NO: 16)
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPGK
```

An Fc protein variant included in compositions and methods according to aspects of the present disclosure is or includes:

```
                                        (SEQ ID NO: 17)
DKTHTCPPCPAPELLGGPSVFLFPPKPKDTLYITREPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPGK
```

An Fc protein, or variant thereof, used in methods of inhibiting a pathogenic virus according to aspects of the present disclosure is obtained by methods such as isolation, synthesis, or recombinant expression of a nucleic acid encoding the Fc protein. Such proteins may also be obtained commercially.

According to aspects of the present disclosure, the cell-targeting component is an antibody or antibody fragment.

As used herein, the terms "antibody" and "antibodies" relate to monoclonal antibodies, polyclonal antibodies, bispecific antibodies, multispecific antibodies, human antibodies, humanized antibodies, chimeric antibodies, camelized antibodies, single domain antibodies, single-chain Fvs (scFv), single chain antibodies, a diabody, a tandem diabody, disulfide-linked Fvs (sdFv), and anti-idiotypic (anti-Id) antibodies (including, e.g., anti-Id antibodies to antibodies of the disclosure), and epitope-binding fragments of any of the above. In particular, antibodies include immunoglobulin molecules and immunologically active fragments of immunoglobulin molecules, i.e., molecules that contain an antigen binding site. Immunoglobulin molecules are of any type (e.g., IgG, IgE, IgM, IgD, IgA and IgY), class (e.g., IgG1, IgG2a, IgG2b, IgG2, IgG3, IgG4, IgA1, and IgA2), or subclass.

Examples of antibody fragments that can be included as a cell-targeting component include Fab fragments, Fab' fragments, F(ab')2 fragments, Fd fragments, Fv fragments, scFv fragments, and domain antibodies (dAb), which specifically bind to a target. Antibody fragments may be generated by any technique known to one of skill in the art. For example, Fab and F(ab')2 fragments may be produced by proteolytic cleavage of immunoglobulin molecules, using enzymes such as papain (to produce Fab fragments) or pepsin (to produce F(ab') 2 fragments). F(ab') 2 fragments contain the complete light chain, and the variable region, the CH 1 region and the hinge region of the heavy chain. Antibody fragments are also produced by recombinant DNA technologies. Antibody fragments may be one or more complementarity determining regions (CDRs) of antibodies.

An antibody or antibody fragment included as a cell-targeting component is a human antibody, humanized antibody, human antibody fragment, or humanized antibody fragment according to aspects of the present disclosure.

Antibodies and methods for preparation of antibodies are well-known in the art. Details of methods of antibody generation and screening of generated antibodies for substantially specific binding to an antigen are described in standard references such as E. Harlow and D. Lane, Antibodies: A Laboratory Manual, Cold Spring Harbor Laboratory Press, 1988; F. Breitling and S. Dubel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; and B. K. C. Lo, Antibody Engineering: Methods and Protocols, Methods in Molecular Biology, Humana Press, 2003.

A cell-targeting component according to aspects of the present disclosure may be an aptamer. The term "aptamer" refers to a nucleic acid that substantially specifically binds to a specified target. In the case of a nucleic acid aptamer, the aptamer is characterized by binding interaction with a target other than Watson/Crick base pairing or triple helix binding with a second and/or third nucleic acid. Such binding interaction may include Van der Waals interaction, hydrophobic interaction, hydrogen bonding and/or electrostatic interactions, for example. Techniques for identification and generation of aptamers is known in the art as described, for example, in F. M, Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; and J. Sambrook and D. W. Russell, Molecular Cloning: A Laboratory Manual, Cold Spring Harbor Laboratory Press, 3rd Ed., 2001.

Methods

Methods according to aspects of the present disclosure provide interferon-stimulated gene 20-kDa protein (ISG20), or a variant thereof, to treat a subject in need thereof. The ISG20 is provided by administering a pharmaceutical composition including one or more of: ISG20, a variant thereof, a nucleic acid encoding ISG20, and a variant thereof, to the subject in need thereof.

The terms "treating" and "treatment" are used herein to refer to reducing or ameliorating the frequency or severity of at least one sign or symptom of pathogenic viral infection.

The terms "preventing" and "prevention" are used herein to refer to inhibiting a pathogenic virus, such as inhibiting infection, such as slowing progression of pathogenic viral infection and/or reducing or ameliorating a sign or symptom of pathogenic viral infection, such as viral replication.

The term "therapeutically effective amount" as used herein refers to an amount of a composition including ISG20, a variant thereof, a nucleic acid encoding ISG20, and a variant thereof, which has a beneficial effect in treating a subject to inhibit a pathogenic virual infection. In subjects having or at risk of having a pathogenic viral infection, a therapeutically effective amount of an ISG20 protein is effective to ameliorate one or more signs and/or symptoms of pathogenic viral infection. For example, a therapeutically effective amount of a composition is effective to detectably decrease viral replication or other sign or symptom of pathogenic viral infection.

Methods according to aspects of the present disclosure provide interferon-stimulated gene 20-kDa protein (ISG20), or a variant thereof, to treat a subject in need thereof, wherein the subject has, or is suspected of having, an infection by a pathogenic positive-sense single-stranded RNA virus and/or a pathogenic DNA virus.

Such pathogenic viral infections to be treated or prevented include infections by a virus including, but are not limited to, Coronavirus, Zika virus, Herpes Simplex virus-1 (HSV-1), Herpes Simplex virus-2 (HSV-2), Hepatitis A virus (HAV), Hepatitis virus (HBV), Hepatitis C virus (HCV), Yellow fever virus (YFV), Bovine viral diarrhea virus (BVDV), Vesicular stomatitis virus (VSV), Encephalomyocarditis virus (EMCV), Influenza virus, Human immunodeficiency virus (HIV), Sindbis virus (SB), West Nile virus, Dengue virus, Kaposi's sarcoma-associated herpesvirus (KSHV), Porcine reproductive and respiratory syndrome virus (PRRSV), Rabies virus (RABV), Epstein-Barr virus (EBV), and Cytomegalovirus.

According to particular aspects of the present disclosure, the pathogenic viral infection is a coronavirus infection. According to particular aspects of the present disclosure, the coronavirus infection is an infection by severe acute respiratory syndrome coronavirus 2 (SARS-CoV-2). According to particular aspects of the present disclosure, the coronavirus infection is an infection by Zika virus. According to particular aspects of the present disclosure, the coronavirus infection is an infection by HSV-2.

Methods according to aspects of the present disclosure are provided for inhibition of pathogenic viral infection, including prevention and/or treatment of pathogenic viral infection, by administering a therapeutically effective amount of a pharmaceutical composition including one or more of: ISG20, a variant thereof, a nucleic acid encoding ISG20, and a variant thereof, to cells infected by a pathogenic virus or at risk of infection by a pathogenic virus, in vitro or in vivo.

According to aspects of the present disclosure, inhibiting a pathogenic virus includes contacting the ISG20 protein, or variant thereof, and viral nucleic acid of the pathogenic virus, in vitro or in vivo, results in at least partial degradation of the viral nucleic acid via the exonuclease activity of the ISG20 protein, or variant thereof.

According to aspects of the present disclosure, inhibiting a pathogenic virus includes administering a therapeutically effective amount of a pharmaceutical composition including one or more of: ISG20, a variant thereof, a nucleic acid encoding ISG20, and a variant thereof, in vitro or in vivo, whereby the ISG20 protein, or variant thereof, interrupts the viral life cycle in the cell.

According to aspects of the present disclosure, inhibiting a pathogenic virus includes administering a therapeutically effective amount of a pharmaceutical composition including one or more of: ISG20, a variant thereof, a nucleic acid encoding ISG20, and a variant thereof, to a subject whereby the ISG20 protein, or variant thereof, modulates an immune response of the subject, thereby inhibiting the pathogenic coronavirus.

Methods according to aspects of the present disclosure are provided for inhibition of pathogenic coronavirus infection, including prevention and/or treatment of pathogenic coronavirus infection, by administering a therapeutically effective amount of a pharmaceutical composition including one or more of: ISG20, a variant thereof, a nucleic acid encoding ISG20, and a variant thereof, to cells infected by a pathogenic coronavirus virus or at risk of infection by a pathogenic coronavirus, in vitro or in a subject, i.e. in vivo.

According to aspects of the present disclosure, inhibiting a pathogenic coronavirus includes contacting the ISG20 protein, or variant thereof, and viral nucleic acid of the pathogenic coronavirus, in vitro or in a subject, i.e. in vivo, resulting in at least partial degradation of the coronavirus nucleic acid via the exonuclease activity of the ISG20 protein, or variant thereof.

According to aspects of the present disclosure, inhibiting a pathogenic coronavirus includes administering a therapeutically effective amount of a pharmaceutical composition including one or more of: ISG20, a variant thereof, a nucleic acid encoding ISG20, and a variant thereof, to a cell in vitro or in a subject, i.e. in vivo, whereby the ISG20 protein, or variant thereof administered, and/or the ISG20 protein, or variant thereof produced by expression from the nucleic acid encoding ISG20, or a variant thereof, interrupts the coronavirus life cycle in the cell.

According to aspects of the present disclosure, inhibiting a pathogenic coronavirus includes administering a therapeutically effective amount of a pharmaceutical composition including one or more of: ISG20, a variant thereof, a nucleic acid encoding ISG20, and a variant thereof, to a subject having or suspected of having a pathological coronavirus infection, whereby the ISG20 protein, or variant thereof administered and/or the ISG20 protein, or variant thereof produced by expression from the nucleic acid encoding ISG20, or a variant thereof, modulates an immune response of the subject, thereby inhibiting the pathogenic coronavirus.

Methods according to aspects of the present disclosure are provided for inhibition of pathogenic coronavirus infection, including prevention and/or treatment of pathogenic coronavirus infection, wherein the pathogenic coronavirus is severe acute respiratory syndrome coronavirus 2 (SARS-CoV-2), by administering a therapeutically effective amount of a pharmaceutical composition including one or more of: ISG20, a variant thereof, a nucleic acid encoding ISG20, and a variant thereof, to cells infected by SARS-CoV-2 or at risk of infection by SARS-CoV-2, in vitro or in a subject, i.e. in vivo.

According to aspects of the present disclosure, inhibiting SARS-CoV-2 includes contacting the ISG20 protein, or variant thereof, and viral nucleic acid of the SARS-CoV-2, in vitro or in a subject, i.e. in vivo, resulting in at least partial degradation of the SARS-CoV-2 nucleic acid via the exonuclease activity of the ISG20 protein, or variant thereof.

According to aspects of the present disclosure, inhibiting SARS-CoV-2 includes administering a therapeutically effective amount of a pharmaceutical composition including one or more of: ISG20, a variant thereof, a nucleic acid encoding ISG20, and a variant thereof, to a cell in vitro or in a subject, i.e. in vivo, whereby the ISG20 protein, or variant thereof administered, and/or the ISG20 protein, or variant thereof produced by expression from the nucleic acid encoding ISG20, or a variant thereof, interrupts the SARS-CoV-2 life cycle in the cell.

According to aspects of the present disclosure, inhibiting SARS-CoV-2 includes administering a therapeutically effective amount of a pharmaceutical composition including one or more of: ISG20, a variant thereof, a nucleic acid encoding ISG20, and a variant thereof, to a subject having or suspected of having a SARS-CoV-2 infection, whereby the ISG20 protein, or variant thereof administered and/or the ISG20 protein, or variant thereof produced by expression from the nucleic acid encoding ISG20, or a variant thereof, modulates an immune response of the subject, thereby inhibiting the SARS-CoV-2.

Methods according to aspects of the present disclosure are provided for inhibition of a Zika virus infection, including prevention and/or treatment of Zika virus infection, by administering a therapeutically effective amount of a pharmaceutical composition including one or more of: ISG20, a variant thereof, a nucleic acid encoding ISG20, and a variant thereof, to cells infected by Zika virus or at risk of infection by Zika virus, in vitro or in a subject, i.e. in vivo. According to aspects of the present disclosure, the subject is a pregnant human.

According to aspects of the present disclosure, inhibiting Zika virus includes contacting the ISG20 protein, or variant thereof, and viral nucleic acid of the Zika virus, in vitro or in a subject, i.e. in vivo, resulting in at least partial degradation of the Zika virus nucleic acid via the exonuclease activity of the ISG20 protein, or variant thereof. According to aspects of the present disclosure, the subject is a pregnant human.

According to aspects of the present disclosure, inhibiting Zika virus includes administering a therapeutically effective amount of a pharmaceutical composition including one or more of: ISG20, a variant thereof, a nucleic acid encoding ISG20, and a variant thereof, to a cell in vitro or in a subject, i.e. in vivo, whereby the ISG20 protein, or variant thereof administered, and/or the ISG20 protein, or variant thereof produced by expression from the nucleic acid encoding ISG20, or a variant thereof, interrupts the Zika virus life cycle in the cell. According to aspects of the present disclosure, the subject is a pregnant human.

According to aspects of the present disclosure, inhibiting Zika virus includes administering a therapeutically effective amount of a pharmaceutical composition including one or more of: ISG20, a variant thereof, a nucleic acid encoding ISG20, and a variant thereof, to a subject having or suspected of having a SARS-CoV-2 infection, whereby the ISG20 protein, or variant thereof administered and/or the ISG20 protein, or variant thereof produced by expression from the nucleic acid encoding ISG20, or a variant thereof, modulates an immune response of the subject, thereby inhibiting the Zika virus. According to aspects of the present disclosure, the subject is a pregnant human.

Methods according to aspects of the present disclosure are provided for inhibition of pathogenic coronavirus infection, including prevention and/or treatment of pathogenic coronavirus infection, wherein the pathogenic coronavirus is HSV-2, by administering a therapeutically effective amount of a pharmaceutical composition including one or more of: ISG20, a variant thereof, a nucleic acid encoding ISG20, and a variant thereof, to cells infected by HSV-2 or at risk of infection by HSV-2, in vitro or in a subject, i.e. in vivo.

According to aspects of the present disclosure, inhibiting HSV-2 includes contacting the ISG20 protein, or variant thereof, and viral nucleic acid of the HSV-2, in vitro or in a subject, i.e. in vivo, resulting in at least partial degradation of the HSV-2 nucleic acid via the exonuclease activity of the ISG20 protein, or variant thereof.

According to aspects of the present disclosure, inhibiting HSV-2 includes administering a therapeutically effective amount of a pharmaceutical composition including one or more of: ISG20, a variant thereof, a nucleic acid encoding ISG20, and a variant thereof, to a cell in vitro or in a subject, i.e. in vivo, whereby the ISG20 protein, or variant thereof administered, and/or the ISG20 protein, or variant thereof produced by expression from the nucleic acid encoding ISG20, or a variant thereof, interrupts the HSV-2 life cycle in the cell.

According to aspects of the present disclosure, inhibiting HSV-2 includes administering a therapeutically effective amount of a pharmaceutical composition including one or more of: ISG20, a variant thereof, a nucleic acid encoding ISG20, and a variant thereof, to a subject having or suspected of having an HSV-2 infection, whereby the ISG20 protein, or variant thereof administered and/or the ISG20 protein, or variant thereof produced by expression from the nucleic acid encoding ISG20, or a variant thereof, modulates an immune response of the subject, thereby inhibiting the HSV-2.

Methods according to aspects of the present disclosure provide for inhibition of pathogenic viral infection, such as preventing or treating pathogenic viral infection, by introducing QQ-modified ISG20 protein (QQ-ISG20) and/or a QQ-modified ISG20 protein variant into cells infected or at risk for infection by a pathogenic virus, by administering the QQ-ISG20 and/or QQ-modified ISG20 protein variant to a subject infected with the pathogenic virus or at risk of infection by the pathogenic virus.

Methods according to aspects of the present disclosure provide for inhibition of pathogenic viral infection, such as preventing or treating pathogenic viral infection, by introducing QQ-modified ISG20 protein (QQ-ISG20) protein, or a QQ-modified ISG20 variant, into cells infected or at risk for infection by a pathogenic virus, in vitro or in vivo. According to particular aspects of the present disclosure, introducing a QQ-modified ISG20 protein, or a QQ-modified ISG20 variant, into cells infected or at risk of infection by the pathogenic virus in vitro or in vivo is achieved without introduction of a nucleic acid encoding the ISG20 protein or variant thereof. Contacting the ISG20 protein, or a variant thereof, and the viral nucleic acid results in at least partial degradation of the viral nucleic acid via the exonuclease activity of the ISG20 protein, or the variant thereof, such that the pathogenic virus is inhibited.

Methods according to aspects of the present disclosure provide for inhibition of SARS-CoV-2 infection, such as preventing or treating pathogenic viral infection, by introducing QQ-modified ISG20 protein (QQ-ISG20) and/or a QQ-modified ISG20 protein variant into cells infected or at risk for infection by a SARS-CoV-2 virus, in vitro or in vivo. According to particular aspects of the present disclosure, introducing a QQ-modified ISG20 protein, or a variant thereof, into cells infected or at risk of infection by a SARS-CoV-2 virus in vitro or in vivo is achieved without introduction of a nucleic acid encoding the ISG20 protein or the variant thereof. Contacting the ISG20 protein and SARS-CoV-2 nucleic acid results in at least partial degradation of the SARS-CoV-2 nucleic acid via the exonuclease activity of the ISG20 protein or variant thereof such that the SARS-CoV-2 virus is inhibited.

Thus, methods according to aspects of the present disclosure provide for inhibition of SARS-CoV-2 virus infection, such as preventing or treating SARS-CoV-2 pathogenic viral infection, by introducing QQ-modified ISG20 protein (QQ-ISG20) into cells infected or at risk for infection by a SARS-CoV-2 virus, by administering the QQ-ISG20 to a subject infected with the SARS-CoV-2 virus or at risk of infection by the SARS-CoV-2 virus. According to particular aspects of the present disclosure, introducing a QQ-modified ISG20 protein into cells of a subject infected or at risk of infection by a SARS-CoV-2 virus, wherein the cells are in vivo, is achieved without introduction of a nucleic acid encoding the ISG20 protein. Contacting the ISG20 protein and SARS-CoV-2 nucleic acid results in at least partial degradation of the SARS-CoV-2 nucleic acid via the exonuclease activity of the ISG20 protein such that the SARS-CoV-2 virus is inhibited, thereby treating and/or preventing SARS-CoV-2 virus disease, e.g. COVID-19, in the subject.

In vitro methods according to aspects of the present disclosure are useful, for example, in assessing prevention and/or treatment of particular cells or cell types in isolation.

Administration of Pharmaceutical Composition

A pharmaceutical composition according to aspects of the present disclosure may be administered acutely or chronically. For example, a composition as described herein may be administered as a unitary dose or in multiple doses over a relatively limited period of time, such as seconds-hours. In a further embodiment, administration may include multiple doses administered over a period of days-years, such as for chronic treatment of pathogenic viral infection or chronic risk of pathogenic viral infection.

A therapeutically effective amount of an ISG20 protein or variant thereof, or a nucleic acid expression construct encoding an ISG20 protein or variant thereof, a QQ-modified ISG20 protein, or a QQ-modified ISG20 protein variant, will vary depending on the route of administration and form of the composition being administered and the particular composition administered, the severity and type of condition being treated in the subject, the species of the subject, the age and sex of the subject and the general physical characteristics of the subject to be treated. One of skill in the art could determine a therapeutically effective amount in view of these and other considerations typical in medical practice without undue experimentation in view of the present disclosure and what is known in the art. In general it is contemplated that a therapeutically effective amount would be in the range of about 0.001 ng/kg-100 mg/kg body weight, optionally in the range of about 0.01 ng/kg-1 mg/kg, and further optionally in the range of about 0.1 ng/kg-0.1 mg/kg. Further, dosage may be adjusted depending on whether treatment is to be acute or continuing.

Usually between 1 and 100 doses of an ISG20 protein or variant thereof, or a nucleic acid expression construct encoding an ISG20 protein or variant thereof, are administered to treat a subject in need thereof, although more doses can be given. An ISG20 protein or variant thereof, or a nucleic acid expression construct encoding an ISG20 protein or variant thereof, can be administered twice a day, daily, biweekly, weekly, every other week, monthly or at some other interval, for a treatment course extending one day, 1 week, 2 weeks, 4 weeks, 1 month, 2 months, 3-6 months or longer. A course of treatment is optionally repeated and may extend to chronic treatment if necessary.

Administration of an ISG20 protein or variant thereof, or a nucleic acid expression construct encoding an ISG20 protein or variant thereof, according to aspects of a method of the present disclosure includes administration according to a dosage regimen to produce a desired response. A suitable schedule for administration of doses depends on several factors including age, weight, gender, medical history and health status of the subject, type of composition used and route of administration, for example. One of skill in the art is able to readily determine a dose and schedule of administration for a particular subject.

Methods according to embodiments of the present disclosure include administration of an ISG20 protein or variant thereof, or a nucleic acid expression construct encoding an ISG20 protein or variant thereof, as a pharmaceutical formulation, such as by systemic or local administration. Exemplary routes of administration include, but are not limited to, parenteral, oral, rectal, nasal, pulmonary, epidural, ocular, otic, intraarterial, intracardiac, intracerebroventricular, intracranial, intradermal, intravenous, intramuscular, intraperitoneal, intraplacental, intraosseous, intrathecal, intravesical, subcutaneous, topical, transdermal, and transmucosal, such as by sublingual, buccal, vaginal, and inhalational routes of administration.

The ISG20 protein or variant thereof, or a nucleic acid expression construct encoding an ISG20 protein or variant thereof, may be administered parenterally, for example, by injection such as intravenous injection, intramuscular injection, intraperitoneal injection, subcutaneous injection, transdermal injection, intrathecal injection, intracranial injection, intracerebrospinal injection, and/or continuous infusion such as by an intravenous or intracerebrospinal continuous infusion device.

Combination Treatments

Combinations of therapeutic agents are administered according to aspects of the present disclosure.

In some aspects, an ISG20 protein or variant thereof, or a nucleic acid expression construct encoding an ISG20 protein or variant thereof, and at least one additional therapeutic agent are administered to a subject to inhibit pathogenic viral infection in a subject in need thereof.

In some aspects, an ISG20 protein or variant thereof, or a nucleic acid expression construct encoding an ISG20 protein or variant thereof, and at least one additional therapeutic agent are administered to a subject to prevent or treat pathogenic viral infection in a subject in need thereof.

In still further aspects, an ISG20 protein or variant thereof, or a nucleic acid expression construct encoding an ISG20 protein or variant thereof, and at least two additional therapeutic agents are administered to a subject to treat a disorder in a subject in need thereof.

The term "additional therapeutic agent" is used herein to denote a chemical compound, a mixture of chemical compounds, a biological macromolecule (such as a nucleic acid, an antibody, a protein or portion thereof, e.g., a peptide), or an extract made from biological materials such as bacteria, plants, fungi, or animal (particularly mammalian) cells or tissues which is a biologically, physiologically, or pharmacologically active substance (or substances) that acts locally or systemically in a subject.

Additional therapeutic agents included in aspects of methods and compositions of the present disclosure include, but are not limited to, antibiotics, antivirals, antineoplastic agents, analgesics, antipyretics, antidepressants, antipsychotics, anti-cancer agents, antihistamines, anti-osteoporosis agents, anti-osteonecrosis agents, antiinflammatory agents, anxiolytics, chemotherapeutic agents, diuretics, growth factors, hormones, non-steroidal anti-inflammatory agents, steroids and vasoactive agents.

Combination therapies utilizing an ISG20 protein or variant thereof, or a nucleic acid expression construct encoding an ISG20 protein or variant thereof, and one or more additional therapeutic agents may show synergistic effects, e.g., a greater therapeutic effect than would be observed using either the ISG20 protein or variant thereof, or a nucleic acid expression construct encoding an ISG20 protein or variant thereof, or one or more additional therapeutic agents alone as a monotherapy.

According to aspects, combination therapies include: (1) pharmaceutical compositions that include an ISG20 protein or variant thereof, or a nucleic acid expression construct encoding an ISG20 protein or variant thereof, in combination with one or more additional therapeutic agents; and (2) co-administration of an ISG20 protein or variant thereof, or a nucleic acid expression construct encoding an ISG20 protein or variant thereof, with one or more additional therapeutic agents wherein the ISG20 protein or variant thereof, or nucleic acid expression construct encoding the ISG20 protein or variant thereof, and the one or more additional therapeutic agents have not been formulated in the same composition. When using separate formulations, the ISG20 protein or variant thereof, or the nucleic acid expression construct encoding an ISG20 protein or variant thereof, may be administered at the same time, intermittent times, staggered times, prior to, subsequent to, or combinations thereof, with reference to the administration of the one or more additional therapeutic agents.

Combination treatments can allow for reduced effective dosage and increased therapeutic index of the ISG20 protein or variant thereof, or the nucleic acid expression construct encoding an ISG20 protein or variant thereof, and the one or more additional therapeutic agents used in methods of the present disclosure.

Optionally, a method of inhibiting a pathogenic viral infection in a subject includes an adjunct anti-virus treatment. An adjunct anti-virus treatment can be administration of an anti-virus agent.

Anti-virus agents are described, for example, in Goodman et al., Goodman and Gilman's The Pharmacological Basis of Therapeutics, Chapters 58 and 59, 12th Ed., Macmillan Publishing Co., 2011.

Anti-virus agents illustratively include abacavir, acyclovir, adefovir, amantadine, ampligen, amprenavir, arbidol, atazanavir, atripla, balavir, baloxavir marboxil, bictegravir, boceprevir, cidofovir, cobicistat, combivir, daclatasvir, darunavir, delavirdine, descovy, didanosine, docosanol, dolutegravir, doravirine, ecoliever, edoxudine, efavirenz, elvitegravir, emtricitabine, enfuvirtide, entecavir, etravirine, famciclovir, fomivirsen, fosamprenavir, foscarnet, fosfonet, ganciclovir, ibacitabine, ibalizumab, idoxuridine, imiquimod, imunovir, indinavir, inosine, integrase inhibitor, interferon type i, interferon type ii, interferon type iii, interferon, lamivudine, letermovir, lopinavir, loviride, maraviroc, methisazone, moroxydine, nelfinavir, nevirapine, nexavir, nitazoxanide, norvir, nucleoside analogues, oseltamivir, peginterferon alfa-2a, peginterferon alfa-2b, penciclovir, peramivir, pleconaril, podophyllotoxin, pyramidine, raltegravir, remdesivir, reverse transcriptase inhibitors, ribavirin, rilpivirine, rimantadine, ritonavir, saquinavir, simeprevir, sofosbuvir, stavudine, telaprevir, telbivudine, tenofovir alafenamide, tenofovir disoproxil, tenofovir, tipranavir, trifluridine, trizivir, tromantadine, valaciclovir, valganciclovir, vicriviroc, vidarabine, viramidine, zalcitabine, zanamivir, and zidovudine.

Embodiments of inventive compositions and methods are illustrated in the following examples. These examples are provided for illustrative purposes and are not considered limitations on the scope of inventive compositions and methods.

EXAMPLES

Material and Methods

Cell Culture and Infection

Immortalized human trophoblast Sw.71 cells and human endometrial stroma cells (HESC) were cultured in DMEM/F12 or DMEM supplemented with 10% FBS, 10 mm HEPES, 0.1 mm MEM non-essential amino acids, 1 mm sodium pyruvate, and 100 U/ml penicillin/streptomycin (Life Technologies; Waltham, MA, USA) under 5% $CO_2$ at 37° C. For viral infections, cells were seeded in 6-well plates at $1.75\times10^5$ cells per well, the next day, ZIKV was added to the cells for 1 hour incubation (at indicated MOI) with gentle agitation every 20 min, after 1 hour, the inoculum was removed and the cells were washed twice with phosphate-buffered saline (PBS), then cells were maintained in 10% FBS DMEM/F12 media for the duration of the experiment. At indicated time points after infection, cell pellets and conditioned media were collected for downstream analysis.

Human Primary Trophoblast Isolation and Culture

Human primary trophoblast cells were isolated from first trimester elective terminations as described in Straszewski-Chavez et al., 2009, Placenta, 30, 939-48. The tissue specimen was collected in cold, sterile phosphate-buffered saline (PBS) and immediately transported to the laboratory for cell culture preparation. Briefly, first trimester placental villous tissues were cut and digested in PBS supplemented with 0.25% Trypsin (Gibco, Grand Island, NY, USA) for 10 minutes at 37° C. with gentle agitation. An equal volume of 10% FBS (Gibco, Grand Island, NY, USA) and Dulbecco's Modified Eagle Medium (DMEM) (Gibco, Grand Island, NY, USA) was added to inactivate the trypsin. The supernatant was collected and centrifuged at 1500 rpm at room temperature for 10 min. The pellet was resuspended in 5 milliliters DMEM media supplemented with 10% FBS. This suspension was laid over lymphocyte separation media (ICN Biomedicals, Inc., Aurora, OH, USA) and centrifuged at 2000 rpm for 20 min. The interface containing the trophoblast cells was collected and centrifuged at 1500 rpm for 10 minutes. Cells were resuspended in DMEM with 10% FBS and then plated on a 6-well plate to grow.

Knockout of ISG20 Using CRISPR/Cas9

ISG20 was knocked out in Sw.71 first-trimester trophoblast cell line using CRISPR/Cas9. Two DNA oligonucleotides were synthesized as follows: Sense: 5'-CACCGCAGCACCGTGGACGTTCACG-3' (SEQ ID NO:3), Antisense: 5'-AAACCGTGAACGTCCACGGTGCTGC-3' (SEQ ID NO:4). Oligonucleotides were phosphorylated using T4 polynucleotide kinase and annealed by heating equimolar amounts to 95° C. and cooling slowly to room temperature. This resulting guide was introduced to lentiCRISPRv2GFP plasmid using BsmBI restriction sites, and lentiCRISPRv2GFP was obtained from Addgene plasmid #82416), see Walter et al., 2017, Cancer Res, 77, 1719-1729. Ten micrograms of the resulting plasmid was co-transfected with 8 micrograms of packaging plasmid pCMV-VSV-G and 4 micrograms of envelope plasmid psPAX2 in the presence of 60 micrograms of polyethylenimine (PEI) into HEK293T cells in a 100-mm dish. pCMV-VSV-G was obtained from Addgene (plasmid #8454), see Stewart et al., 2003, RNA, 9, 493-501, and psPAX2 was obtained from Addgene (plasmid #12260). Then packaged viral particles were collected by ultracentrifugation and were transduced into the Sw.71 cells. The cells were sorted based on the GFP signal by fluorescence activated cell sorting (FACS) following transduction. The deletion of ISG20 was confirmed using Sanger sequencing technique performed by GENEWIZ, and the overall efficiency was 91.1% analyzed by TIDE (Tracking of Indels by Decomposition). Moreover, the protein expression was verified by Western blot.

Virus

ZIKV strain FSS 13025, which was originally isolated in Cambodia in 2010, was obtained from the World Reference Center for Emerging Viruses and Arboviruses at University of Texas Medical Branch, Galveston as described in Aldo et al., 2016, Am J Reprod Immunol, 76, 348-357. ZIKA virus was propagated in African green monkey kidney (Vero) cells by infecting the monolayer with viral stock. When the cytopathic effect was observed in the whole monolayer, the infected supernatant was collected and centrifuged. The virus stocks were aliquoted and stored at −80° C. The viral titer of viral stock was determined by plaque assay.

Plaque Assay

The infectivity of the virus was determined by plaque assay in Vero cells. Briefly, Vero cells were plated into 12-well plates at $2.5\times10^5$ cells/well and inoculated with 200 microliters of 10-fold serial dilutions of viral stocks and incubated at 37° C. for 1 hour with gentle agitation. After inoculation, Vero cells were overlaid with media containing DMEM (Gibco, #11965-084), 2% FBS, and 0.6% Avicel (FMC, #CL-611). Cells were maintained at 37° C. in 5% $CO_2$ for 5 days. After 5 days incubation, overlays were aspirated and the cells were fixed in 4% formaldehyde solution in PBS before staining with 1% crystal violet in 20% methanol. Viral plaques were photographed and each plaque was counted as a plaque-forming unit (PFU). Viral titer was calculated as PFU/[volume virus (mL)×(dilution factor)].

Production and Purification of Recombinant ISG20-Fc Protein

For the production of recombinant ISG20 protein from mammalian cell cultures, a plasmid encoding the protein was designed and transfected into Chinese Hamster ovary cells (CHO). Briefly described, an artificial gene sequence was obtained from Life Technologies, which coded for the following: 5' BamHI restriction site, cell export signal sequence from hENPP7, 10×His tag for nickel purification, Tev sequence (to enable cleavage of the protein), full-length human ISG20, a linker (Gly-Ser-Gly-Ser-Gly, SEQ ID NO:5), the Fc domain of human $IgG_1$, and a 3' EcoRI restriction site.

According to aspects of the present disclosure, a fusion protein including ISG20 and Fc portion of human IgG includes:

(SEQ ID NO: 12)
MRGPAVLLTVALATLLAPGAGAHHHHHHHHHHENLYFQGMAGSREVVAM
DCEMVGLGPHRESGLARCSLVNVHGAVLYDKFIRPEGEITDYRTRVSGV
TPQHMVGATPFAVARLEILQLLKGKLVVGHDLKHDFQALKEDMSGYTIY
DTSTDRLLWREAKLDHCRRVSLRVLSERLLHKSIQNSLLGHSSVEDARA
TMELYQISQRIRARRGLPRLAVSDGSGSGDKTHTCPPCPAPELLGGPSV
FLFPPKPKDTLYITREPEVTCVVVDVSHEDPEVKFNWYVDGVEVHNAKT
KPREEQYNSTYRVVSVLTVLHQDWLNGKEYKCKVSNKALPAPIEKTISK
AKGQPREPQVYTLPPSREEMTKNQVSLTCLVKGFYPSDIAVEWESNGQP
ENNYKTTPPVLDSDGSFFLYSKLTVDKSRWQQGNVFSCSVMHEALHNHY
TQKSLSLSPGK where signal sequence ENPP7 is present from amino acids 1-22, a His tag is present from amino acids 22-32, a Tev sequence is present from amino acids 33-39 which allows for cleavage between Q and G, ISG20 is present from amino acids 40-220, a linker is present from amino acids 221-225, and a variant of an Fc portion of human IgG is present from amino acids 226-452, including 3 mutations at amino acids 32, 34, and 36 of the Fc portion of human IgG shown herein as SEQ ID NO:16 where M→Y, S→T, and T→E, referred to as M257Y, S259T, and T261E with reference to the full-length fusion protein of SEQ ID NO:12.

The term "Tev sequence" refers to an amino acid sequence specifically cleaved by Tobacco Etch Virus protease, an endopeptidase, a highly sequence-specific cysteine protease from Tobacco Etch Virus (TEV) which recognizes the specific amino acid sequence ENLYFQG/S and cleaves between Q and G/S. A Tev sequence can be included in a fusion protein for controlled cleavage at a specified site.

In order to increase the binding affinity of the fusion protein with the Fc receptor, three amino acids within the Fc region were changed by using the QuikChange II site directed mutagenesis kits (Agilent, #200523), introducing M257Y, S259T, and T261E mutations simultaneously in the Fc region.

Mutagenesis primers are as follows:

MST Fwd: 5'-

(SEQ ID NO: 6)
CCCCAAAGCCCAAAGACACTCTGTATATCACCAGGGAGCCTGAAGTTAC
ATGCGTCGTTGT-3'

MST Rev: 5'-

(SEQ ID NO: 7)
ACAACGACGCATGTAACTTCAGGCTCCCTGGTGATATACAGAGTGTCTT
TGGGCTTTGGGG-3'

All of this sequence had been codon optimized for efficient expression in CHO cells. Using BamHI/EcoRI, this cassette was subcloned into pcDNA4 (Invitrogen, #V102020) vector, because the carrier vector in which the cassette was supplied lacked a promoter. Once completed, the plasmid was transfected into CHO cells using polyethyleneimine, and cells were then selected for plasmid integration with Zeocin treatment.

After transfection and Zeocin selection, the cells were dissociated and serial diluted into a selection media containing 150 μg/ml Zeocin for 2 weeks to establish stable single cell clones. After the expanding of single clones, positive clones were selected by evaluating the protein expression of ISG20-Fc in the cytosol (endogenous) and supernatant (secreted) by western blot analysis. Additionally, conditioned media from stable cell clones was used to assess anti-ZIKA activity in vitro, and the clones with the highest efficacy were expanded and adapted for suspension growth in Pepro AF-CHO serum free media (Peprotech). Six liters of media at $5\times10^6$ cells/milliliter was centrifuged at 1000×g for 30 minutes and the secreted protein was purified to homogeneity as described in Albright et al., 2015, Nat Commun, 6, 10006, using an AKTA Pure 25M equipped for multi-step automated purification with modifications. First, many non-specific CHO cell secreted proteins were eliminated from the active fraction by ammonium sulfate precipitating, final concentration of 23% $(NH_4)_2SO_4$. The remaining soluble protein was further purified by sequential nickel column and MabSelect prismA affinity column purification followed by an S75 sizing column. Purified proteins were stored as frozen stocks in PBS at −80° C.

RNA Degradation Assay

Purified ZIKV RNA and HSV-2 DNA were extracted using QIAamp MinElute Virus Spin Kit (Qiagen, catalog no. 57704), and 50 nanograms of purified viral RNA/DNA was incubated with the recombinant protein at different concentrations for 90 minutes at 37° C. in the presence of SUPERase In™ RNase inhibitor (Invitrogen, catalog no. AM2694), and the resulting RNA/DNA was tested for viral copies by qRT-PCR. Subsequently, the PCR product was used for agarose gel electrophoresis to evaluate the degradation of RNA/DNA as described in Aranda et al., 2012, Electrophoresis, 33, 366-9.

Mouse Experiments

The IFNAR1−/− (B6.129S2-Ifnar1$^{tm1Agt}$/Mmjax) mice were obtained from the Jackson Laboratory (Bar Harbor, ME) and bred in a specific-pathogen-free facility at Wayne State University. Adult (8-12 weeks of age) IFNAR1' mice were set up for timed-mating and the plug day was considered as embryonic days E0.5. On embryonic days E8.5, the plug-positive mice were inoculated intraperitoneally (i.p.) with either $1\times10^5$ plaque-forming units (pfu) of ZIKA virus (in 100 μL volume) or 1% FBS DMEM/F12 media (vehicle). One hour after ZIKV/vehicle injection, treatment with rISG20-Fc (1 mg/kg) or PBS (control) was administrated i.p. to the pregnant mice. On E9.5 and E10.5, same protein/PBS injection was performed on the pregnant mice. On E14.5, the mice were sacrificed for tissue collection.

Pregnancy outcome parameters including the number of implantations and resorptions were recorded, and fetus development was evaluated by comparing the weight, fetal crown-rump length (CRL) and occipitofrontal diameter (OFD) between groups. Maternal spleen, placentas, fetal brain were collected and stored in RNAlater™ stabilization solution (Invitrogen, catalog no. AM7021) at −80° C. for viral titer quantification. Furthermore, maternal serum was used for cytokine expression analysis by Luminex (BioRad) and some placentas from each group were stored in 4% paraformaldehyde for haematoxylin and eosin staining.

RNA Extraction and Real-Time PCR Analysis

Cells were collected and total RNA was extracted using the RNeasy Mini kit (Qiagen, catalog no. 74106) according to the manufacturer's instructions. Viral RNA from mice serum was extracted using QIAamp MinElute Virus Spin Kit (Qiagen, catalog no. 57704) according to the manufacturer's protocol. RNA from mice tissue was extracted as described. Briefly, tissue was homogenized in Trizol (Ambion; Waltham, MA, USA) in 1.0-mm zirconium beads (Benchmark; Sayreville, NJ, USA) for two cycles at 400 g for 2 min. Supernatant was then transferred to a new tube and incubated for 5 minutes at room temperature (RT). 200 μl chloroform/ml of Trizol was added, shaken for 15 seconds, and then incubated for 3 minutes at RT. Samples were centrifuged at 12,000 g for 15 minutes at 4° C., and aqueous phase was transferred to new tubes. Then, 500 microliters of 100% isopropanol was added, incubated at RT for 10 min, and centrifuged at 12,000 g for 10 minutes at 4° C. Supernatant was then discarded, and cell pellet was washed twice with 500 microliters of 100% ethanol and centrifuged at 12,000 g for 5 min. The pellet was then washed twice with 1 milliliter of 75% ethanol, vortexed briefly, then centrifuged at 7,500 g for 5 minutes at 4° C., and then air-dried for 10 minutes. The pellet was resuspended in 50 microliters of RNase-free water.

RNA concentration and purity were assessed using spectrophotometric analyses of 260/280 ratios, and only samples with values of 1.8 or higher were used for PCR analysis. One microgram of RNA was reverse-transcribed for each sample using Bio-Rad (Hercules, CA, USA) iScript cDNA synthesis kit. iTaq Universal SYBR Green Supermix (BioRad) and gene-specific primers were added to the RT reactions that were diluted 1:5 with nuclease-free water and run on the CFX96, C1000 system qPCR machine (BioRad). Values were normalized to GAPDH and calculated with $2^{-\Delta\Delta Ct}$ method as described in Livak and Schmittgen, 2001, Methods, 25, 402-8.

Virus Titer Quantification by qRT-PCR

ZIKA viral titer was quantified by one-step quantitative reverse transcriptase PCR (qRT-PCR). ZIKA Viral RNA was isolated from Zika virus stock using QIAamp MinElute Virus Spin Kit (Qiagen, catalog no. 57704) to create a standard curve using serial 10-fold dilutions of ZIKV RNA. One microgram of RNA from samples was run on CFX96, C1000 system qPCR machine (BioRad) using a one-step PCR mix (Promega, catalog no. A6120). Zika virus was detected using primer pair: forward 5'-CCGCTGCCCAACACAAG-3' (SEQ ID NO:8) and reverse 5'-CCACTAACGTTCTTTTGCAGACAT-3' (SEQ ID NO:9). The probe sequence is 5'-AGCCTACCTTGACAAGCAGTCAGACACTCAA-3' (SEQ ID NO:10) 6-FAM/ZEN/IBFQ, see Foy et al., 2011, Emerg Infect Dis, 17, 880-2; Lanciotti et al., 2008, Emerg Infect Dis, 14, 1232-9. The cycling conditions involved activation at 45° C. for 15 minutes and 95° C. for 2 minutes, followed by 40 amplification cycles of 95° C. for 15 seconds, and 60° C. for 1 minute.

Viral RNA was quantified by comparing each sample's threshold cycle (CT) value with a ZIKV RNA standard curve.

Western Blotting

For protein extraction, cells were lysed on ice in cell lysis buffer (1% Triton X-100, 0.05% SDS, 100 mM $Na_2PO_4$, and 150 mM NaCl) supplemented with protease inhibitor mixture (Roche) and PMSF for 15 minutes followed by centrifugation at 16,000 g for 15 minutes at 4° C. to remove cell debris. The protein concentration was determined by bicinchoninic acid (BCA) assay (Pierce, catalog no. 23223, Rockford, IL). 30 μg of each protein lysate were electrophoresed on a 12% SDS-polyacrylamide gel. The proteins were then transferred onto polyvinylidene difluoride membranes (EMD Millipore). The membrane was blocked with PBS-0.05% Tween 20 (PBS-Tween) containing 5% nonfat milk (Fisher Scientific, Pittsburgh, PA), and the membranes were washed three times and incubated with primary antibody in 1% milk PBS-Tween at 4° C. overnight. The membranes were then washed with PBS-Tween three times followed by a secondary antibody in 1% milk PBS-Tween for 2 hours at RT. Immunoreactivity was detected using enhanced chemiluminescence (NEN Life Sciences, Waltham, MA) and imaged by Kodak 20000MM Image Station. Antibodies were diluted as following: 1:1000 anti-ISG20 (Proteintech, catalog no. 22097-1-AP); 1:10,000 anti-β-actin (Sigma, catalog no. A2066); 1:10,000 peroxidase-conjugated anti-rabbit IgG (Cell Signaling Technology, catalog no. 7074).

IFNβ Secretion Analysis by ELLA

The IFNβ secretion of supernatants from the trophoblast cells with or without ZIKV infection was determined using the Simple Plex immunoassay system (ELLA, Protein Simple, San Jose, CA) as described in Aldo et al., 2016, Am J Reprod Immunol, 75, 678-93. Briefly, 50 microliters of sample was added to sample inlet ports on a cartridge, then the sample was split into multiple parallel channels from the sample inlet port. Each channel was specific for one particular analyte and subjected to a typical sandwich immunoassay protocol. The entire immunoassay procedure was automated, and the analyzed results were obtained using the manufacture-encoded calibration curves.

Statistical Analysis

Statistical analyses were performed using Prism software, version 8 (GraphPad, San Diego, CA). All data are presented as means±SEM. Differences between two groups were analyzed using unpaired Student's t-test and differences among multiple groups were analyzed by one-way ANOVA. Depending on the distribution of the continuous variables, nonparametric test was used if the data was not normally distributed. A p-value<0.05 was considered statistically significant.

Results

ZIKV Infection Induces IFNβ and ISGs mRNA Expression in First-Trimester Trophoblast Cells.

Cellular components involved during an effective anti-viral response elicited by trophoblast cells exposed to ZIKV was characterized in this example. A well-characterized human first-trimester trophoblast cell line (Sw.71) and primary cultures of human first-trimester trophoblast cells were used.

Figure 1A:
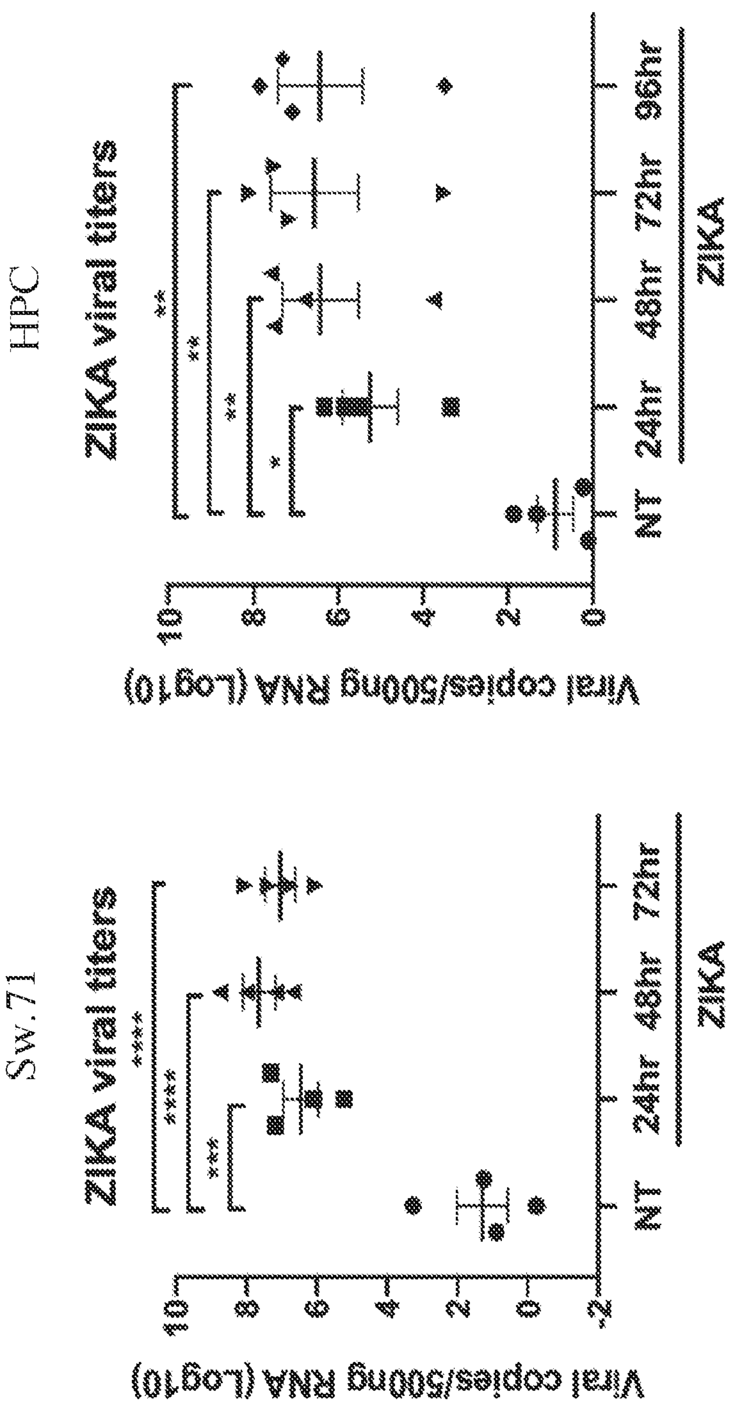
FIGS. 1A, 1B, 1C, and 1D show that ZIKV infection induces type I IFNβ expression in human first-trimester trophoblast cell line Sw.71 and human primary cultures; human first-trimester trophoblast cell line Sw.71 and human primary culture trophoblast cells were infected with ZIKV (MOI=2) for 1 hour and refreshed with regular media over time; RNA was collected for measuring viral titers and gene expression by qRT-PCR; data represent as mean±SEM from three or four independent experiments (each dot represents one independent experiment); NT, no treatment group; HPC, human primary culture.

Both cell types were infected with Cambodia ZIKV (MOI=2) for 1 hour, refreshed with regular media and monitored to determine changes in cell growth and survival. During the infection, Sw.71 cells and primary cultures of first-trimester trophoblast infected with ZIKV did not show any apoptosis-related morphological changes or disturbance on cell growth when compared to the control, and viral titers were evaluated at different time points post infection by qRT-PCR. ZIKV titers in Sw.71 were detected at 24 hours post infection (h.p.i.), with higher levels at 48 h.p.i and decrease on viral titers at 72 h.p.i. (FIG. 1A). In human primary trophoblast cell cultures (HPC), ZIKV titers increased at 24 h.p.i and stayed at high level of ZIKV titer until 96 h.p.i. (FIG. 1A). Due to the technical limitations of maintaining primary cultures for longer time, viral titers at later times (more than 96 h.p.i.) were not monitored, but no signs of cell death in the primary trophoblast cell cultures were observed.

Figure 1B:
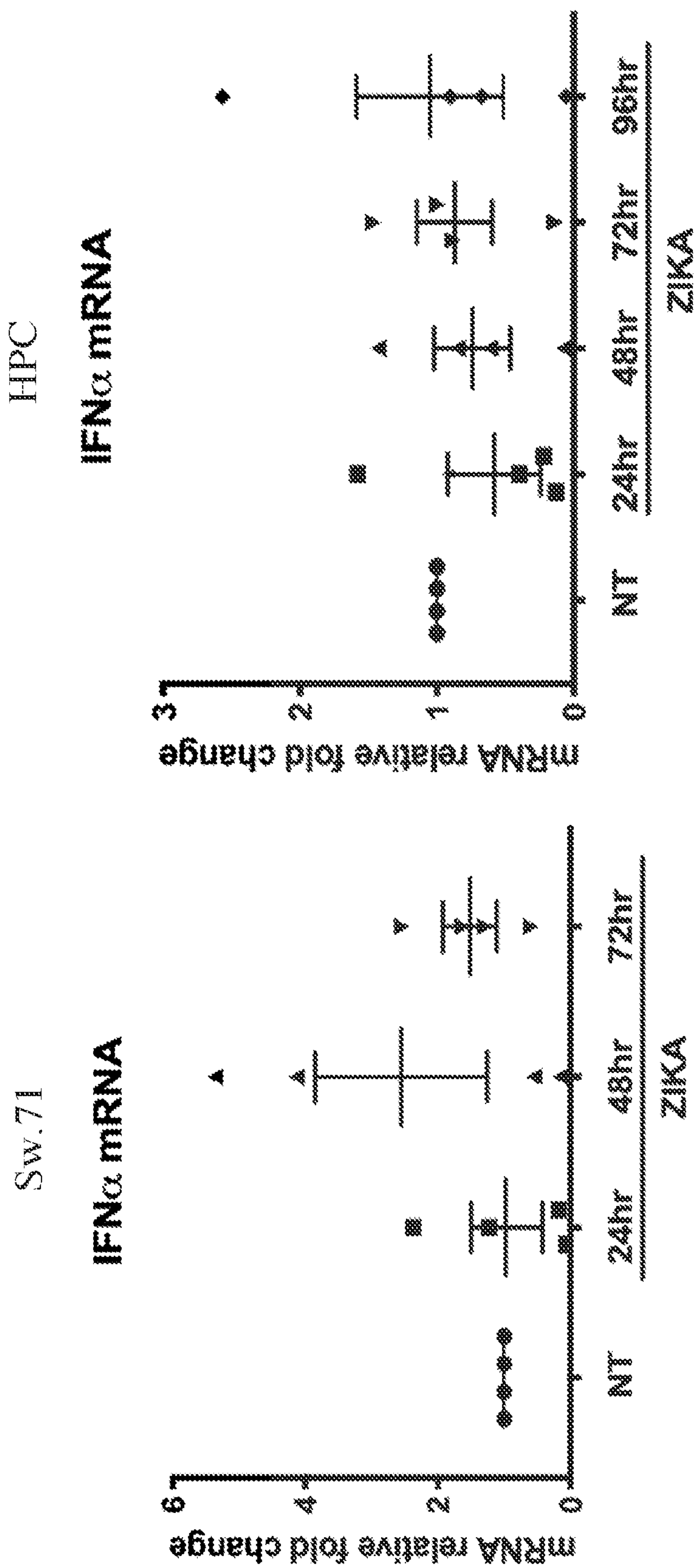
Figure 1C:
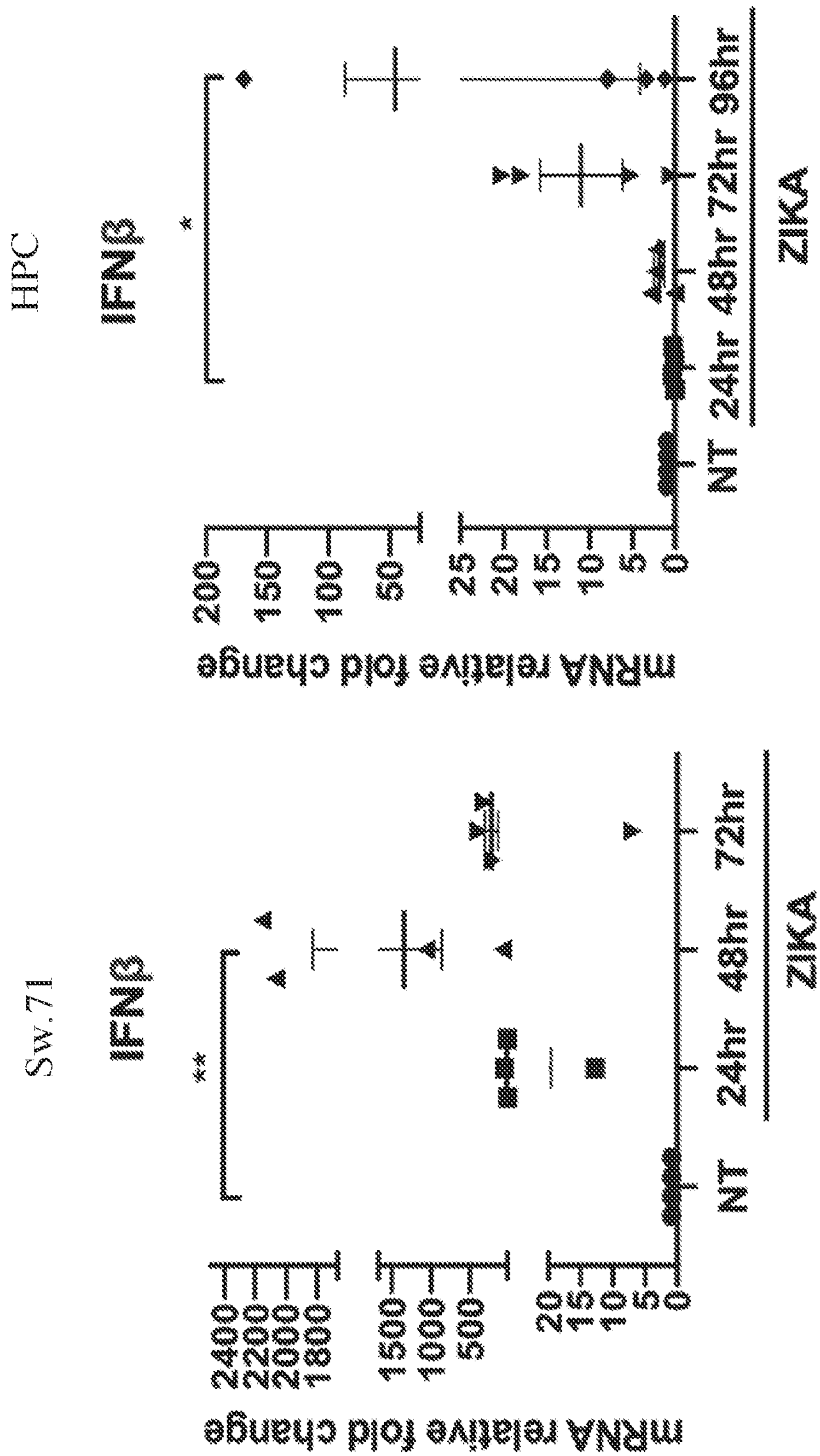

To understand the anti-viral response generated by trophoblast cells to ZIKV infection, the type I interferon response was first characterized in Sw.71 and HPC infected with ZIKV (MOI=2) over different time points post ZIKV infection. Inhibition of IFNα mRNA expression by ZIKV infection (FIG. 1B) was observed, but a time-dependent increase of IFNβ mRNA (FIG. 1C), which was consistent with the time-dependent pattern of ZIKV titers. IFNβ mRNA expression in Sw.71 increased in the first 24 h.p.i., peaked at 48 h.p.i., and further decreased 72 h.p.i. (FIG. 1C). In HPC the IFNβ response followed similar pattern as the viral infection; IFNβ mRNA increased at 48 h.p.i. and remained high at 72 h.p.i. and 96 h.p.i. (FIG. 1C). Although the response times were different between the cell line and the primary cultures, both cell types showed significant increase of IFNβ expression in response to ZIKV infection (FIG. 1C).

Figure 1D:
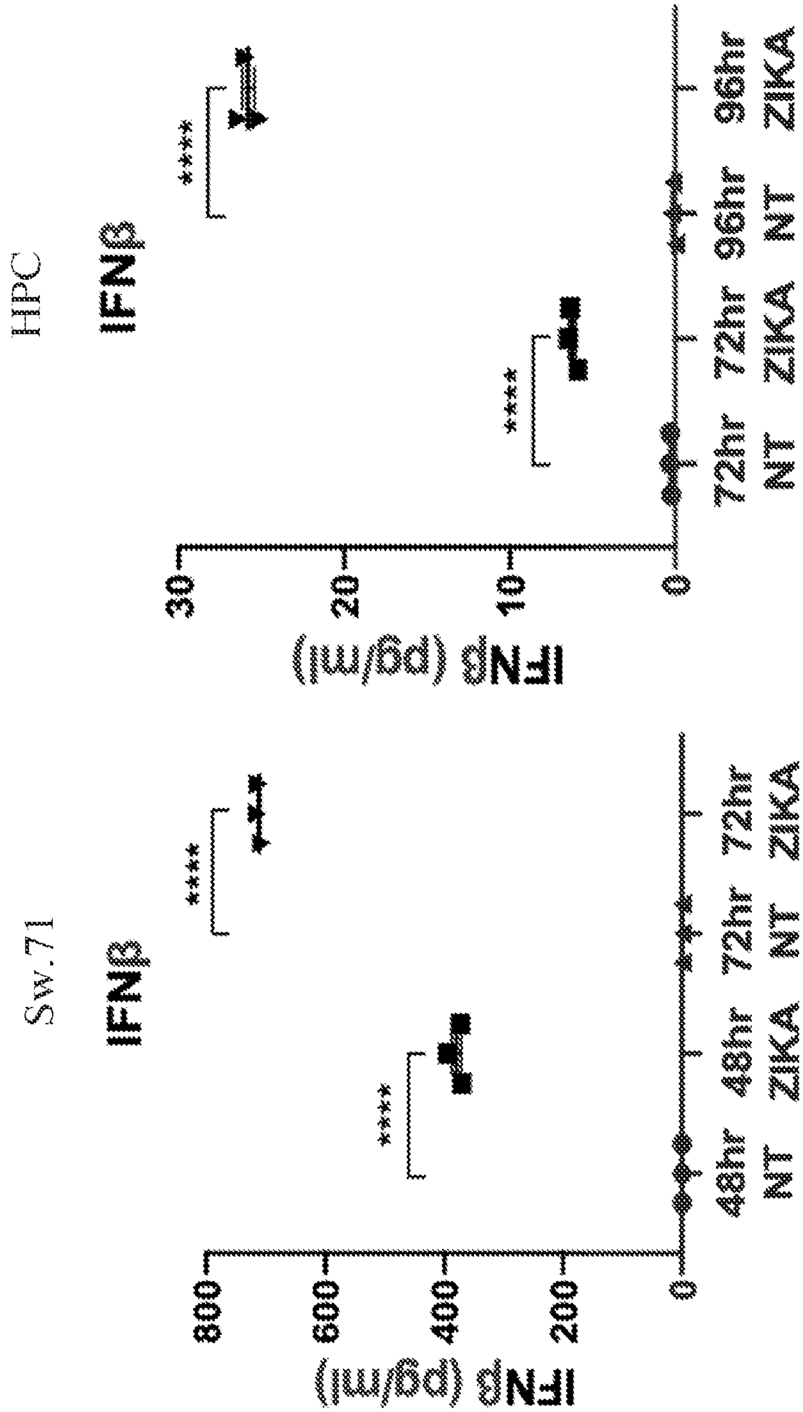

To validate the observed increase of IFNβ mRNA expression and its potential function following ZIKV infection, the presence of secreted IFNβ protein was assayed in the supernatant of Sw.71 and HPC trophoblast cells at different time points post ZIKV infection. Secreted IFNβ was not detected in the supernatant of control non-infected Sw.71 cells, however, a substantial concentration of secreted IFNβ protein was detected in the supernatant of ZIKV-infected Sw.71 cells at 48 and 72 h.p.i. (FIG. 1D). While in HPC, IFNβ protein was undetectable in the supernatant both from non-infected and ZIKV-infected cells at 24 and 48 h.p.i., a significant increase of secreted IFNβ protein was observed at 72 and 96 h.p.i (FIG. 1D). Therefore, these findings confirm that trophoblast cells can recognize ZIKV infection and initiate a type I IFNβ response to ZIKV infection.

IFNβ Promotes ISGs Expression in Trophoblast Cells in Response to ZIKV Infection.

Following its secretion from cells, IFNβ mediates its anti-viral activity by inducing the expression of Interferon stimulated genes (ISGs). Thus, mRNA expression of the anti-viral ISGs: ISG20, MX1, OAS1, ISG15, CH25H, TRIM22, Tetherin, and Viperin was evaluated in Sw. 71 and HPC trophoblast cells following ZIKV infection. Similar to IFNβ expression, a significant increase of the mRNA expression was observed for all these ISGs at 48 h.p.i. followed by decreased expression levels at 72 h.p.i. in Sw.71 cells infected with ZIKV. HPC showed similar response although at different times, with a peak of ISGs mRNA expression at 96 h.p.i.; which correlated with the time of IFNβ peak expression.

To determine whether these ZIKA-induced ISGs are downstream of IFNβ, Sw.71 cells were treated with increasing doses of IFNβ (3, 30, 300 ng/ml) for 8 hours, and ISGs mRNA expression was determined by qRT-PCR. IFNβ was able to induce the expression of these ISGs in a dose-dependent manner. These results suggest that IFNβ-induced ISGs expression in trophoblast cells are the early responders to ZIKV infection. Interestingly, no similar IFNβ/ISGs response was observed in trophoblast cells infected with Herpes Simplex Virus-2 (HSV-2), suggestive of the differential responses of trophoblast cells to different virus infection.

Induction of ISG20 Expression by IFNβ in Response to ZIKV Infection

An early step in the cellular anti-viral response is to target the viral RNA before it is able to replicate and produce new viral particles. This process is accomplished through the expression of exonucleases that specifically degrade viral RNA. Screening of the anti-viral ISGs in this example, demonstrated the induction of ISG20 in human first-trimester trophoblast cells infected with ZIKV. ISG20 functions as an interferon-inducible 3'-5' exonuclease and has been shown to exert a potent antiviral activity against different viruses.

In this example it was confirmed that ISG20 expression is directly regulated by IFNβ. Sw.71 or HPC were treated with increasing concentrations of IFNβ (3, 30, 300 ng/ml) for 8 hours and ISG20 mRNA expression was quantified by qRT-PCR. IFNβ was observed to be a very strong inducer of ISG20 mRNA expression in trophoblast cells (Sw.71 and HPC) and its effect was dose-dependent (FIG. 2A). Furthermore, the induction of ISG20 by IFNβ was early (FIG. 2B), since a significant increase of ISG20 mRNA expression as early as 2 hours following exposure to IFNβ (300 ng/ml) was observed and was further enhanced until 16 hours and slightly decreased at 24 hours (FIG. 2B).

Next, it was determined whether the changes in ISG20 mRNA were translated into protein expression. Trophoblast cells were treated with increasing concentrations of IFNβ for 24 hours and protein expression was determined by western blot analysis. Interestingly, no protein expression was observed in non-stimulated trophoblast cells (FIG. 2C and FIG. 2D); even though they have high basal mRNA levels as shown by the Cq value ranging from 23 to 26. However, IFNβ was able to induce ISG20 protein expression in a dose and time-dependent manner in both Sw.71 and HPC (FIG. 2C and FIG. 2D). Intriguingly, this protein expression is tightly regulated. ISG20 protein expression was observed as early as 4 hours post IFNβ treatment and increased up to 16 hours in HPC. Afterwards, ISG20 protein expression decreased to almost basal levels (FIG. 2D). This data demonstrates that ISG20 transcription and translation are both inducible by IFNβ in first-trimester trophoblast cells.

Poly(I:C) Induces IFNβ and ISG20 Expression in Trophoblast Cells.

ISG20 expression in response to a general viral RNA was investigated in this example. Polyinosinic: polycytidylic acid (Poly I:C), which is a synthetic double-stranded RNA that can mimic viral infection when applied in vitro and in vivo was used. Sw.71 and primary trophoblast cells were treated with different doses of Poly(I:C) (0.25, 2.5, 25 μg/ml). IFNβ and ISG20 mRNA and protein expression were determined by qRT-PCR and western blot, respectively. Poly(I:C) treatment induced IFNβ and ISG20 mRNA expression in a dose-dependent manner in Sw.71 and HPC trophoblast cells. At the protein level, Poly(I:C) also induced ISG20 protein expression in a dose-dependent manner in both cell types. HPC trophoblasts seemed to be more sensitive to Poly(I:C) treatment since increased levels of ISG20 protein expression were detected when cells were treated with Poly(I:C) at its lowest concentration (0.25 μg/ml). Based on these findings, the earlier time when Poly(I:C) can promote IFNβ and ISG20 expression in trophoblast cells was determined. Accordingly, Sw.71 and primary trophoblast cells were treated with Poly(I:C) (25 μg/ml) and cell pellets were collected at 2, 4, 8, 16, 24 hours post-treatment for mRNA evaluation and 4, 8, 16, 24, 48 hours post-treatment for protein evaluation. FIG. 3C shows that Poly (I:C) treatment in Sw.71 cells induced IFNβ mRNA expression as early as 2 hours post treatment reaching higher levels at 16 hours and decreasing at 24 hours. ISG20 mRNA expression followed similar pattern of expression as IFNβ, although the earliest increase was detected at 8 hours post treatment, and a major increase at 16 and 24 hours. In HPC, a similar early response to Poly(I:C) was observed for IFNβ and ISG20. However, contrary to Sw.71 cells, the IFNβ mRNA levels remained higher even at 24 hours post treatment. A comparable response in protein expression was observed when HPC were treated with Poly(I:C). As indicated above, trophoblast cells do not express ISG20 protein in basal conditions. However, following treatment with Poly(I:C) (25 μg/ml), ISG20 protein expression was detected as early as 16 hours post-treatment. Altogether, these data suggest that ZIKA viral RNA and Poly(I:C) can be sensed by trophoblasts cells, which will lead to the induction of a Type I IFNβ response and expression of ISG20.

Role of ISG20 in Controlling ZIKV Infection in Trophoblast Cells.

In this example it was evaluated whether trophoblasts would elicit a similar ISG20 response to ZIKV infection as the one observed with Poly (I:C). Firstly, Sw.71 were infected with ZIKA virus (MOI=2) for 1 hour and cell pellets were collected at 24, 48, 56 and 72 h.p.i., and ISG20 protein expression was determined by western blot. Results confirmed that ZIKV infection induced ISG20 protein expression (FIG. 3A) in a time-dependent manner, which was correlated to the increase in ISG20 mRNA. Moreover, ISG20 protein expression was detected at 24, 48 and 56 h.p.i. and decreased at 72 h.p.i. (FIG. 3A).

To further elucidate the specific role of ISG20 during ZIKV infection, a trophoblast cell line lacking ISG20 ($ISG20^{-/-}$ Sw.71) was established using the CRISPR-Cas9 system. The validation of $ISG20^{-/-}$ Sw.71 was evidenced by the lack of ISG20 protein expression following Poly(I:C) treatment. Wild type (wt) Sw.71 and $ISG20^{-/-}$ Sw.71 were infected with ZIKA virus (MOI=2) for 1 hour and incubated with refreshed growth media for 48 hours. Afterwards, RNA and protein were collected to determine viral titers by qRT-PCR and protein expression by western blot. In contrast to wt Sw.71 cells, which showed ISG20 protein expression following ZIKV infection, no detectable ISG20 protein expression was observed in $ISG20^{-/-}$ Sw.71 (FIG. 3B). More importantly, $ISG20^{-/-}$ Sw.71 exhibited significant higher viral titer levels when compared to wt Sw.71 (FIG. 3C); suggesting that the lack of ISG20 rendered trophoblast cells more susceptible to ZIKV infection.

Subsequently, it was evaluated whether the lack of ISG20 could have an impact in the process of ZIKV shedding. Vero cells were cultured in the presence of supernatants collected from 48 hours ZIKV-infected wt Sw.71 and $ISG20^{-/-}$ Sw.71 cells, and ZIKV shedding was determined by plaque assay. As shown in FIG. 3D and FIG. 3E, more plaques were formed in Vero cells exposed to supernatants from ZIKV-infected $ISG20^{-/-}$ Sw.71 group compared to supernatants from the ZIKV-infected wt Sw.71 group.

To further understand the mechanism responsible for the increased viral titer in $ISG20^{-/-}$ Sw.71, it was assessed whether the lack of ISG20 would affect the expression of other ISGs necessary for the anti-ZIKV response. First, the levels of IFNβ expression after ZIKV infection were assessed and it was observed that, although the levels of induction were different, both wt Sw.71 cells and $ISG20^{-/-}$ Sw.71 cells could significantly induce IFNβ mRNA expression after ZIKV infection (FIG. 4A). Next, the mRNA expression of several other anti-viral ISGs (MX1, OAS1, ISG15, CH25H, TRIM22, Tetherin and Viperin) was evaluated in ZIKV-infected wt Sw.71 and $ISG20^{-/-}$ Sw.71 cells. As shown in FIG. 4B, both cell lines showed an increased expression of anti-viral ISGs, while the only major difference between the two cell lines was the lack of ISG20 in the $ISG20^{-/-}$ Sw.71 trophoblast cells (FIG. 4C). Increased mRNA levels for the tested ISGs were observed in $ISG20^{-/-}$ Sw.71 trophoblast cells, although the fold changes were not as robust as those observed in wt Sw.71 (FIG. 4B), which suggests that ISG20 may play a role in regulating the expression of other ISGs during ZIKV infection.

The response to ZIKV infection in IFNβ pre-treated trophoblast cells was evaluated, and showed that treatment of wt Sw.71 with IFNβ (30 ng/ml) was able to increase ISG20 protein expression and significantly decreased ZIKV titers (FIG. 4C and FIG. 4D). However, similar pre-treatment with IFNβ in $ISG20^{-/-}$ Sw.71 failed to induce ISG20 and had minimal effect on controlling ZIKV titers (FIG. 4C and FIG. 4D). Similarly, IFNβ pre-treatment of $ISG20^{-/-}$ Sw.71 did not decrease viral shedding, which is shown by the higher ZIKV titer of HESC cells that were exposed to supernatants from $ISG20^{-/-}$ Sw.71. In summary, this data demonstrates that ISG20 is an early and critical component of the anti-ZIKV response, which functions by inhibiting ZIKV replication and dissemination in trophoblast cells.

Characterization of the Anti-Viral Effect of Recombinant ISG20.

ISG20 can be used as an anti-viral treatment by blocking early stages of viral replication. To demonstrate this, a recombinant form of ISG20 was generated by cloning the full-length of human ISG20, a linker (Gly-Ser-Gly-Ser-Gly, SEQ ID NO:5), and the human Fc domain into pcDNA4 vector. A cell secretion signal was used along with a His tag for purification. The protein structure is shown in FIG. 5A and includes the following regions: 1) ISG20 sequence; 2) Linker; 3) Fc domain; 4) Tev sequence, cleavage between Q and G; 5) secretory signal sequence (ENPP7); 6) His Tag.

Use of the human Fc domain is optional, as is the linker. The inclusion of the human Fc domain can be used to 1) increase the stability of the protein in the circulation; 2) block the viral transmission from mother to fetus since placenta expresses Fc receptor extensively and therefore the protein will bind to placenta.

Also included in the construct are a cell secretion signal, and a His tag for purification. Either or both of these can be substituted with another sequence providing the same function, or omitted.

Following the procedures shown in FIG. 5B, this plasmid was transfected into Chinese hamster ovary (CHO) cells and selected for plasmid integration by growing the cells in the presence of Zeocin. Positive clones were selected and the expression of ISG20 was evaluated in the cytosol (endogenous) and supernatant (secreted) by western blot analysis (FIG. 5C). Positive clones were selected based on the intracellular expression of ISG20, but more importantly, the detection of ISG20 expression in the supernatant; confirming the secretion of the protein (FIG. 5C). No detectable ISG20 protein was found in the supernatant or cell lysate of the negative clone or non-transfected CHO cells (FIG. 5C).

Next, the conditioned media was collected from the positive and negative clones and added that to the ISG20$^{-/-}$ Sw.71 trophoblast cells together with ZIKA virus (MOI=2) for 1 hour, followed by refreshing with new growth media for 48 hours. RNA was collected to determine viral titers by qRT-PCR. The conditioned media from the positive clone, significantly reduced ZIKV viral titers compared to the negative clone (FIG. 5D). This data suggests that the secreted form of ISG20 preserves its RNase activity and shows anti-ZIKA effect. The recombinant ISG20-Fc protein was purified for further characterization.

Anti-Viral Activity of Recombinant ISG20-Fc Protein

To test if the exonuclease activity of recombinant ISG20-Fc (rISG20-Fc) was preserved, it was first examined its ability to degrade viral RNA or DNA. Two different viruses were used as the substrates for this experiment: RNA virus (ZIKA) and DNA virus (HSV-2). 50 ng purified ZIKV RNA or HSV-2 DNA were incubated with increasing concentrations of rISG20-Fc (5, 50, 500 ng) for 90 min at 37° C. in the presence of RNase inhibitor to exclude the effect of exogenous RNase, followed by quantification of viral titers by qRT-PCR. rISG20-Fc was able to degrade both ZIKV RNA and HSV-2 DNA in a dose dependent manner, however, rISG20-Fc was more efficient in degrading viral RNA than DNA (FIG. 5E).

In Vivo Efficacy of rISG20-Fc Inhibiting ZIKA Viral Replication in IFNAR$^{-/-}$ Pregnant Mice Having shown that rISG20-Fc maintained its exonuclease activity, it was then tested whether rISG20-Fc could have an anti-viral effect by using the IFNAR1$^{-/-}$ mice, which are highly sensitive to ZIKV infection. Adult (8-12 weeks of age) IFNAR1$^{-/-}$ pregnant mice were intraperonteially (i.p.) infected with $1\times10^5$ pfu ZIKV or 1% FBS DMEM/F12 media (vehicle) at day E8.5 (FIG. 6A). Afterwards, animals received three doses of rISG20-Fc (1 mg/kg) i.p. 1 hour post-ZIKV infection and on days E9.5 and E10.5 of their pregnancy. Control animals were injected with PBS at the same time points (FIG. 6A). On E14.5, mice were sacrificed and organs were collected to assess viral titer. In control mice, macroscopic evaluation of the uterus showed the presence of fetal death and resorptions in ZIKV infected mice (FIG. 6B). However, rISG20-Fc treatment rescued this phenotype by significantly decreasing the pregnancy loss (FIG. 6B. No differences in the number of implantation sites were found between the two groups, which confirms the protective effect of rISG20-Fc.

Next, the impact of ZIKV infection and treatment with rISG20-Fc on fetal development was analyzed. ZIKV infection is known to have major negative impacts on fetal development as demonstrated by a significant decrease in fetal weight, crown-rump length (CRL), and occipitofrontal diameter (OFD) (FIG. 6C). Treatment of ZIKV-infected pregnant mice with rISG20-Fc significantly improved fetal CRL when compared to the infected group, indicating that rISG20-Fc can promote fetus development in the uterus (FIG. 6C).

The anti-viral effect of rISG20-Fc treatment was evaluated by quantifying ZIKV titers on the maternal and fetal side. On the maternal side, a significant decrease in ZIKV titers was observed in the maternal serum in mice that were treated with rISG20-Fc (FIG. 7A). On the fetal side, a significant decrease in ZIKV titers in the fetal brain of rISG20-Fc treated mice was observed (FIG. 7B). Interestingly, there was no observed difference in ZIKV titer in the placenta between the two groups. This may suggest that rISG20-Fc can block viral transmission from the placenta to fetus, thus protecting the fetus from the detrimental effects of ZIKV infection.

Impact of rISG20-Fc Treatment on Placental Integrity

In this example it was determined whether treatment with rISG20-Fc could modulate the immunological response elicited by ZIKV infection on the maternal and fetal side. Maternal serum cytokine expression of ZIKV infected dams treated with rISG20-Fc or vehicle control was evaluated. It was observed that rISG20-Fc treatment had a modulatory effect on the anti-viral response by significantly reducing inflammatory cytokines (Endotaxin) (FIG. 7C).

Next, histologic analysis of placenta samples from each group was performed to determine the impact of the ZIKV-induced inflammatory process on the placenta and if this could be countered with rISG20-Fc treatment. Thus, utero-placental units were collected at E14.5 (day 6 post infection), and H&E staining was performed. All histological samples were analyzed in a blinded manner by an independent animal pathologist. As shown in FIG. 7D, placentas obtained from animals infected with ZIKV showed major alteration on placenta structure characterized by multifocal loss of tissue architecture (necrosis) in the labyrinth, apparent damage of the vascularity evidenced by decrease blood vessel density, edema were observed only in the decidua of infected mice, necrosis and inflammation foci were observed in the labyrinth of infected mice. Additional pathologic changes present within the labyrinth of infected mice included an overall tissue hypereosinophilia, nuclear pyknosis, and cellular fragmentation (FIG. 7D). Treatment with rISG20-Fc reversed some of these changes, including increased vascularity, decreased decidual edema, and cellular fragmentation at the labyrinth (FIG. 7D). This data suggests that rISG20-Fc treatment can contribute to placenta integrity during ZIKV infection and facilitate fetal development.

Modification of ISG20 with QQ-Technology

To increase the cellular uptake of rISG20, rISG20 was used with a "QQ" reagent, providing QQ-modified rISG20 (QQ-ISG20).

QQ-modification: Modification of expressed ISG20 protein with protein transduction reagent QQ to produce QQ-modified ISG20 protein The protein transduction reagent (QQ reagent) can be adjusted by altering the composition to include reagents as shown in Table 1 to obtain the best protein transduction efficiency for the particular cell type.

For in vivo applications, to make total volume 1 milliliter (ml):

TABLE 1

| Protein transduction reagent (QQ reagent) | PEI 1.2K | PEI 2K | PEI 4K | PEI 8K | DOTAP or DOTMA | DOPE or DOGS | POPC | DMPE |
|---|---|---|---|---|---|---|---|---|
| QQ1a | 10-200 μl | — | — | — | 25-100 μl | 25-100 μl | — | — |
| QQ2a | 10-200 μl | — | 10-100 μl | — | 25-100 μl | 25-100 μl | — | — |
| QQ3a | 10-200 μl | — | 10-100 μl | 10-100 μl | 25-100 μl | 25-100 μl | — | — |
| QQ4a | 10-200 μl | 10-100 μl | — | 10-100 μl | 25-100 μl | 25-100 μl | — | — |
| QQ5a | 10-200 μl | 10-100 μl | 10-100 μl | 10-100 μl | 25-100 μl | 25-100 μl | — | — |
| QQ6a | 10-200 μl | 10-100 μl | 10-100 μl | 10-100 μl | — | — | 25-100 μl | 25-100 μl |
| QQ7a | 10-200 μl | 10-100 μl | 10-100 μl | 10-100 μl | 25-100 μl | 25-100 μl | 25-100 μl | 25-100 μl |
| QQ8a | 10-200 μl | — | — | 10-100 μl | 25-100 μl | 25-100 μl | 25-100 μl | 25-100 μl |
| QQ9a | 10-200 μl | — | 10-100 μl | 10-100 μl | — | — | 25-100 μl | 25-100 μl |

The polyethylenimine (PEI) concentration for the stock solution:

| 1.2K | 2K | 4K | 8K |
|---|---|---|---|
| 5 mg/ml | 2 mg/ml | 2 mg/ml | 2 mg/ml |

Lipid concentration for the stock solution:

| DOTAP | DOTMA | DOPE | DOGS | POPC | DMPE |
|---|---|---|---|---|---|
| 1 mg/ml | 1 mg/ml | 1 mg/ml | 1 mg/ml | 1 mg/ml | 1 mg/ml |

PBS buffer containing ISG20 protein in 1-6 M urea and specified PEI, lipids is used to make 1 ml total volume.

The ISG20 protein is first dissolved in sodium phosphate buffer (pH7.0, NaCl 50 mM) at concentrations of 0.5-10 mg/ml, depending on protein solubility. Protein solubility was found to influence cationization efficiency. To completely dissolve ISG20 protein, an overnight stir of the protein solution at room temperature is performed (with or without DTT at 3 mM for overnight, depending on if the ISG20 protein has cysteine residues). The ISG20 protein can also be dissolved in 1-6 M urea if needed to improve protein solubility.

A lipid DOTAP/DOPE (1:1) emulsion was prepared using a method as the following: 1 mg of DOTAP/DOPE (0.5 mg:0.5 mg=1:1) mixture was dissolved in chloroform and dried under $N_2$ gas. The dried lipid film was then dissolved in PBS buffer, pH7.0 and the lipid solution was sonicated for 3×30 seconds using a power of 7-8 on a sonicator from Fisher Scientific (Sonic Dismembrator, Model 100) with micro probe. The lipid solution was further incubated at 37° C. for 2 hours until the suspension becomes semi-clear. The prepared emulsion was stored at 4° C. and is stable for one month.

The other ingredients of the QQ reagent (not including the lipid emulsion or the optional Ca or DMSO) were mixed in a tube, according to the recipe described above. The QQ reagent is then titrated into the ISG20 protein solution very slowly, drop by drop, while stirring and then add the lipid emulsion. Once this is completed, the resulting ISG20 protein solution is left at room temperature for 4 hours before use. During this period, gentle stirring is necessary to mix the QQ reagent with ISG20 protein solution and also to allow the QQ-modification of the ISG20 protein reaction to complete. If precipitation is observed, the ISG20 protein solution can be centrifuged at 14,000 rpm for 15 minutes to remove the precipitate. If the precipitate occurs, a BCA protein assay will be carried out using the supernatant to check the amount of ISG20 protein remaining in solution. To ensure the efficiency of ISG20 protein transfer into the cells, the concentration of modified ISG20 protein has to be high enough at >0.1 mg/ml.

Typically, QQ-modified ISG20 protein is prepared at 0.5-1.5 mg/ml concentration, depending on protein solubility, for in vivo administration.

If the majority of the ISG20 protein is precipitated, another QQ reagent can be used for ISG20 protein modification. The QQ series reagents cover a wide range of cationization reagents along with different lipids and enhancers, thus any precipitation problem is solved. The above procedure can be repeated to prepare higher concentrations of QQ-modified ISG20 protein.

The QQ-modified ISG20 protein is passed through a desalting column to separate the QQ-modified ISG20 protein from remaining unreacted materials. The purified proteins are passed through a filter (0.22 μm cutoff, for sterilization before in vivo administration. The purified protein fractions can be concentrated before or after sterilization, such as by using a spin column, and are stable and can be stored at −20° C. for between a few weeks to a few months.

Different QQ reagents can also be used for the best efficiency of protein transfer as well as the least cell toxicity. In addition, different proteins are modified with different QQ reagents for best efficiency of protein transfer into cells. In general, for better in vivo delivery efficiency, QQ5a-QQ9a are used. However, this may cause larger in vivo toxicity. When using QQ5a-QQ9a, use of lower concentrations of larger PEI and lipids is emphasized.

For good in vivo delivery efficiency, QQ1a-QQ4a is used with less in vivo toxicity. QQ1-QQ4 can be used with higher lipid concentrations.

The ISG20 protein was dissolved in 50 mM sodium phosphate pH 7.4 with 2 M urea. Protein transduction reagents (QQ-reagents) were freshly prepared based on the recipe. QQ-reagent used in this example is a cocktail of polyethylenimine (PEI) 1,200 (1.2K, 0.05-1.0 mg/ml) and DOTAP/DOPE (25-100 μg/ml). The QQ-modification of ISG20 protein was performed by mixing the QQ-reagent with ISG20 protein: 1 mg/ml, for 4-hours at room temperature or overnight in a cold room.

Intracellular Uptake of ISG20 vs QQ-ISG20 rISG20 and QQ-ISG20 were each incubated separately with human trophoblast cells, and the uptake activity was monitored by fluorescence microscopy. In contrast to the rISG20 alone, which was only detected in approximately 20% of the cells; high concentrations of QQ-ISG20 were internalized within all the cells and it was localized in the cytoplasm, perinuclear, as well as in the nuclei of the cells.

QQ-ISG20 RNase Activity Against ZIKV

Efficacy of QQ-ISG20 to prevent pathogenic viral infection was tested by pre-treating wild-type Swan 71 and $ISG20^{-/-}$ Swan 71 human trophoblast cells with increasing concentrations of QQ-ISG20 for 24 hours followed by exposure to ZIKV for additional 24 hours. ZIKV titers were then determined by qRT-PCR. Results are shown in FIG. 8A, and demonstrate that QQ-ISG20 significantly prevented viral replication in a dose dependent manner.

Efficacy of QQ-ISG20 to have a beneficial therapeutic effect on pathogenic virus-infected cells was tested by treating ZIKV infected wild-type Swan 71 and $ISG20^{-/-}$ Swan 71 human trophoblast cells with increasing concentrations of QQ-ISG20 for 48 h. Administration of QQ-ISG20 to ZIKV infected wild-type Swan 71 and $ISG20^{-/-}$ Swan 71 human trophoblast cells inhibited the ZIKV titers in the infected cells as shown in FIG. 8B. Collectively, these data demonstrate QQ-ISG20 to have a potent and effective antiviral effect, both preventive as well as therapeutic.

In Vivo Antiviral Effect of QQ-ISG20

The in vivo efficacy of QQ-ISG20 to prevent ZIKV infection was tested in pregnant and non-pregnant $IFNAR1^{-/-}$ mice.

In vivo data shows an anti-viral effect of QQ-ISG20 in pregnant ZIKV-infected $IFNAR1^{-/-}$ mice. Treatment of pregnant mice with QQ-ISG20 has a protective effect on the mother as well as in the fetus, as shown by the decreased pregnancy loss, significant reduction of viral titers in maternal serum and fetal brain.

ZIKV infection in non-pregnant $IFNAR1^{-/-}$ mice is lethal due to systemic infection with high titers in multiple organs including brain, spleen, kidney and lungs. Administration of QQ-ISG20 (1 mg/kg) to non-pregnant $IFNAR1^{-/-}$ mice infected with ZIKV decreased viral titers in these organs, see FIG. 10. Notably, administration of QQ-ISG20 inhibits viral titers in the lungs, thereby treating a significant pathological effect of infection by RNA viruses such as ZIKV and SARS-CoV-2.

Effect of ISG20 or QQ-ISG20 on DNA Viruses

ISG20 is shown herein to degrade viral RNA of RNA viruses such as ZIKV and to degrade double-stranded DNA of viruses such as HSV-2.

The effect of concentration of the administered agent was determined using ISG20 or QQ-ISG20. For this example human trophoblast cells were infected with HSV-2 followed by treatment with either high concentration of ISG20 or increasing concentrations of QQ-ISG20. Viral titers and the level of the infection was evaluated by PCR 48 hours post-infection. As shown in FIG. 11, ISG20-FC at a concentration of 100 μg/ml reduced HSV-2 pathogenic viral infection by 80%. Further, the same level of efficacy is obtained with 10 μg/ml of QQ-ISG20, see FIG. 11. Thus, increasing the concentration of ISG20 in the cells using QQ-ISG20, was found to enhance the anti-HSV-2 activity.

QQ-ISG20 RNase Activity Against SARS-CoV-2

Exonuclease activity of QQ-ISG20 on SARS-CoV-2 was assessed using an vitro assay including synthetic SARS-CoV-2 RNA: ORF E, N as the target and quantifying the copy numbers of SARS-CoV-2 RNA by using the FDA approved CDC qPCR probe assays from Integrated DNA Technologies (IDT, Coralville, Iowa, USA) and from American Type Culture Collection (ATCC, Manassas, VA, USA).

Quantification Method for SARS-CoV-2

As assay to quantify the presence of SARS-CoV-2 was developed based on B the instructions of the manufacturer (www.idtdna.com/pages/landing/coronavirus-research-reagents). Two sets of RT-PCR assays were used, which contains different specific sets of primers targeting different regions of SARS-CoV-2 gene: 2019-nCoV_N1 and 2019-nCoV_N3. N1 assay was designed for specific detection of the 2019-nCoV RNA and N3 assay was used for universal detection of SARS-like coronavirus. A standard curve was established as described by the protocol from CDC (www.cdc.gov/coronavirus/2019-ncov/lab/tool-virus-requests.html). The RT-PCR protocol includes 45 PCR replication cycles, and any cq value above 45 cycles is defined as undetectable. FIG. 12, shows the standard curve of both N1 and N3 assay. The sensitivity of performed assay is 1 μg/μl.

In Vitro Characterization of QQ-ISG20 Exonuclease Activity

ISG20 is a 3' to 5' exonuclease that specifically degrades in vitro single-stranded RNA substrates. In this example, 100 ng synthetic SARS-CoV-2 RNA was incubated with QQ-ISG20 (V2) (100 ng) or with a negative control (V1) (100 ng) for 90 minutes at 37° C. to determine whether QQ-ISG20 could induce in vitro degradation of synthetic SARS-CoV-2 RNA (obtained from ATCC: ATCC® VR-3276SD™).

Following this incubation, 5 microliters (μl) was taken from each sample and RT-PCR was performed. Each reaction contained a total volume of 20 μl per manufacturer instructions. Data is presented as SARS-CoV-2 RNA copies/μl. As shown in FIG. 13, the primers are able to amplify different regions of the synthetic SARS-CoV-2 RNA in the PBS and in the V1 negative control groups (inactive protein) (FIG. 10). However, samples incubated with QQ-ISG20 (V2) (100 ng) had no detectable viral RNA copies.

Specificity of Exonuclease Activity

In order to determine the specificity of QQ-ISG20 RNase degradation activity on synthetic SARS-CoV-2 RNA described in FIG. 13, a dose response test was performed using different concentrations of QQ-ISG20 (V2). Thus, 100 ng of synthetic SARS-CoV-2 RNA was incubated with QQ-ISG20 (V2) (1, 10, 50 and 100 ng) and negative control (V1) (100 ng) for 90 minutes at 37° C. Afterwards, 5 μl was taken from each sample and used for the RT-PCR reaction. Each RT-PCR reaction contained a total volume of 20 μl per manufacturer instructions. Data is presented as SARS-CoV-2 RNA copies/μl. As shown in FIG. 14, using both sets of primers we demonstrated a dose response inhibitory effect of QQ-ISG20 (V2) on SARS-CoV-2 RNA copies. No effect was observed with the inactive control V1.

VISGO1 and VISGO2 Constructs

The rISG20 construct described above contains a signal peptide, ENPP7. However, it was found that the signal peptide could be eliminated without deleterious effect on anti-viral activity. Furthermore, a Tev protease cleavage site present between the ENPP7 signal peptide plus His-tag and ISG20-Fc fragment in the ISG20-Fc construct described above was also found to be optional. Data show that inclusion of His-tag at the N-terminal of rISG20 did not interfere the anti-viral activity. Therefore, there is no need to include a protease cleavage site.

Additional DNA constructs for encoding ISG20 and ISG20-Fc are disclosed herein. These additional constructs do not include a signal peptide and or a protease cleavage site and retain the His-tag for protein purification. Thus, these additional constructs of contain a MHHHHHHSSLA (SEQ ID NO:11) His-tag that is directly linked with either ISG20 or ISG20-Fc proteins. Constructs encoding these proteins were cloned into a bacterial expression vector, pET30a-sHT, for high-level protein production using an *E. Coli* strain BL21 (DE3).

These constructs are designated VISGO1 (His-tag-ISG20, without signal peptide and without the Tev protease cleavage site) and VISGO2 (His-tag-ISG20-Fc, without signal peptide and without the Tev protease cleavage site) and QQ-modified VISGOs are designated QQ-VISGO1 and QQ-VISGO2, respectively.

Bacterially produced QQ-VISGO2 was found to have anti-viral activity equivalent to the rISG20 produced in COS cells for both RNA degradation of ZIKA and SARS-CoV-2 RNAs and prevention of trophoblast cells from ZIKA virus infection (See FIGS. 13-15).

QQ-ISG20 has a potent and highly effective RNase activity against SARS-CoV-2. This therapeutic approach has utility, for example, in targeting the earliest stage of pathogenic viral infection providing specificity and decreasing likelihood of side effects.

Large Scale Production in Bacterial Cells

To obtain an efficient large-scale production system for anti-viral proteins of the present disclosure, double colony selection was used to select a bacterial colony that gave the highest protein expression. With the doubly selected bacterial colonies, small-scale bacterial expression of the proteins using regular incubator shakers at different temperatures and IPTG concentrations. FIG. 15A shows an example of such optimization, indicating higher bacterial expressions of both VISGO1 and VISGO2 at 33° C. with 1 mM IPTG. Once these experimental conditions were optimized, 50 L fermentation was performed for large scale protein expression. Fermentation conditions were achieved that enabled production of both VISGO1 and VISGO2 as shown in FIG. 15B for VISGO1 and in FIG. 15C for VISGO2. In both cases, the $OD_{600}$ of VISGO1 and VISGO2 were 24 to 27, producing 1.3-1.5 kg of bacteria from 50 L fermentation.

Items

Item 1. A method of inhibiting a pathogenic virus, comprising:

providing an ISG20 protein to a cell infected by the pathogenic virus or at risk of being infected by the pathogenic virus, thereby inhibiting the pathogenic virus.

Item 2. The method of item 1, wherein providing the ISG20 protein comprises administering a therapeutically effective amount of the ISG20 protein to a subject having, or at risk of having, a viral infection.

Item 3. The method of item 1 or 2 wherein the virus is a pathogenic virus.

Item 4. The method of any of items 1 to 3, wherein the subject has, or is at risk of having, viral infection by a positive-sense single-stranded RNA virus.

Item 5. The method of any of items 1 to 4, wherein the subject has, or is at risk of having, viral infection by a DNA virus.

Item 6. The method of any of items 1 to 5, wherein the subject has, or is at risk of having, viral infection by a virus selected from the group consisting of: Coronavirus, Zika virus, Hepatitis A virus (HAV), Hepatitis virus (HBV), Hepatitis C virus (HCV), Yellow fever virus (YFV), Bovine viral diarrhea virus (BVDV), Vesicular stomatitis virus (VSV), Encephalomyocarditis virus (EMCV), Influenza virus, Human immunodeficiency virus (HIV), Sindbis virus (SB), West Nile virus, Dengue virus, Kaposi's sarcoma-associated herpesvirus (KSHV), Porcine reproductive and respiratory syndrome virus (PRRSV), Rabies virus (RABV), Epstein-Barr virus (EBV), HSV-2, and Cytomegalovirus Item 7. The method of item 6, wherein the subject has, or is at risk of having, a coronavirus infection.

Item 8. The method of item 7, wherein the coronavirus infection comprises infection by severe acute respiratory syndrome coronavirus 2 (SARS-CoV-2).

Item 9. The method of item 6, wherein the subject has, or is at risk of having a Zika virus infection.

Item 10. The method of item 6, wherein the subject has, or is at risk of having an HIV virus infection.

Item 11. The method of item 6, wherein the subject has, or is at risk of having a HSV-2 virus infection.

Item 12. The method of any of items 1 to 12, wherein administering the ISG20 protein to a subject having, or at risk of having, a viral infection comprises administering a nucleic acid molecule encoding the ISG20 protein.

Item 13. The method of any of items 1 to 12, wherein providing the ISG20 protein to the cell infected by the virus results in at least partial degradation of nucleic acid of the virus.

Item 14. The method of any of items 1 to 11, wherein the ISG20 protein is protein transduction reagent-modified ISG20 protein, wherein the protein transduction reagent is non-covalently bound to the ISG20 protein, and wherein the protein transduction reagent comprises a cation reagent and a lipid.

Item 15. The method of item 14, wherein the cation reagent comprises polyethylenimine.

Item 16. The method of item 14 or 15, wherein the lipid is selected from the group consisting of: DOTMA (N-1(-(2,3-dioleyloxy)propyl-N,N,N-trimethyl-ammonium chloride; DOGS (dioctadecylamido-glycylspermine); DOTAP, 1,2-dioleoyl-3-trimethylammonium-propane; DOPE, 1,2-dioleoyl-n-glycero-3-phosphoethanolamine; POPC, 1-palmitoyl-2-oleoyl-sn-glycero-3-phosphocholine; and DMPE 1,2-dimyristoyl-n-glycero-3-phosphocholine.

Item 17. The method of any of items 14 to 16, wherein the protein transduction reagent is selected from the group consisting of: QQ1a, QQ2a, QQ3a, QQ4a, QQ5a, QQ6a, QQ7a, QQ8a and QQ9a.

Item 18. The method of any of items 1 to 17, wherein the ISG20 comprises SEQ ID NO:1, or a variant thereof.

Item 19. The method of any of items 1 to 18, wherein the ISG20 is recombinantly produced.

Item 20. The method of any of items 1 to 19, wherein the ISG20 is isolated.

Item 21. The method of any of items 1 to 20, wherein the ISG20 comprises a cell-targeting component.

Item 22. A method of inhibiting a Zika virus in a pregnant subject, comprising:

providing an ISG20 protein to a cell infected by the Zika virus or at risk of being infected by the Zika virus, thereby inhibiting the Zika virus.

Item 23. The method of item 22, wherein the cell is a placental cell.

Item 24. The method of item 22 or 23, wherein the isolated ISG20 protein is recombinantly produced.

Item 25. The method of any of items 22 to 24, wherein the ISG20 protein comprises a cell-targeting component.

Item 26. The method of any of items 22 to 25, wherein the ISG20 protein comprises a placental cell-targeting component.

Item 27. The method of any of items 22 to 26, wherein the ISG20 protein comprises an Fc domain of human $IgG_1$.

Item 28. The method of any of items 22 to 27, wherein the ISG20 a protein transduction reagent-modified ISG20 protein, wherein the protein transduction reagent comprises a cation reagent and a lipid.

Item 29. A composition, comprising a protein transduction reagent-modified ISG20 protein and a cell targeting component.

Item 30. The composition of item 29, wherein the cell targeting component comprises a protein transduction reagent comprising a cation reagent and a lipid.

Item 31. The composition of item 30, wherein the cation reagent comprises polyethylenimine.

Item 32. The composition of item 30 or 31, wherein the lipid is selected from the group consisting of: DOTMA (N-1(-(2,3-dioleyloxy)propyl-N,N,N-trimethyl-ammonium chloride; DOGS (dioctadecylamido-glycylspermine); DOTAP, 1,2-dioleoyl-3-trimethylammonium-propane; DOPE, 1,2-dioleoyl-s-glycero-3-phosphoethanolamine; POPC, 1-palmitoyl-2-oleoyl-sn-glycero-3-phosphocholine; and DMPE 1,2-dimyristoyl-n-glycero-3-phosphocholine.

Item 33. The composition of any of items 30 to 32, wherein the protein transduction reagent is selected from the group consisting of: QQ1a, QQ2a, QQ3a, QQ4a, QQ5a, QQ6a, QQ7a, QQ8a and QQ9a.

Item 34. The composition of any of items 29 to 34, wherein the cell targeting component comprises an Fc domain of human $IgG_1$.

Item 35. The method of any of items 1 to 28 or the composition of any of items 29 to 34, wherein the ISG20 comprises SEQ ID NO:1, or a variant thereof.

Item 36. A method of inhibiting a pathogenic virus substantially as shown and/or described herein.

Item 37. A composition comprising a protein transduction reagent-modified ISG20 protein and a cell targeting component substantially as shown and/or described herein.

Item 38. A composition comprising a protein transduction reagent-modified ISG20 protein and a cell targeting component, wherein the cell targeting component is an Fc domain of human $IgG_1$, the composition comprising a fusion protein substantially as shown and/or described herein.

Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method of inhibiting a pathogenic virus in a pregnant subject, comprising: providing a composition comprising an interferon-stimulated gene 20-kDa (ISG20) protein, wherein said ISG20 protein has an exonuclease activity and comprises an amino acid sequence having at least 90% sequence identity to SEQ ID NO: 1, and wherein said ISG20 protein is directly or indirectly covalently bonded to a placental cell-targeting component to a placental cell of the pregnant subject infected by the pathogenic virus or at risk of being infected by the pathogenic virus, thereby inhibiting the pathogenic virus.

2. The method of claim 1, wherein the subject has, or is at risk of having, viral infection by a positive-sense single-stranded RNA virus.

3. The method of claim 1, wherein the subject has, or is at risk of having, viral infection by a DNA virus.

4. The method of claim 1, wherein the subject has, or is at risk of having, viral infection by a virus selected from the group consisting of: Coronavirus, Zika virus, Hepatitis A virus (HAV), Hepatitis virus (HBV), Hepatitis C virus (HCV), Yellow fever virus (YFV), Bovine viral diarrhea virus (BVDV), Vesicular stomatitis virus (VSV), Encephalomyocarditis virus (EMCV), Influenza virus, Human immunodeficiency virus (HIV), Sindbis virus (SB), West Nile virus, Dengue virus, Kaposi's sarcoma-associated herpesvirus (KSHV), Porcine reproductive and respiratory syndrome virus (PRRSV), Rabies virus (RABV), Epstein-Barr virus (EBV), HSV-2, and Cytomegalovirus.

5. The method of claim 1, wherein providing the composition to the placental cell infected by the virus results in at least partial degradation of nucleic acid of the virus.

6. The method of claim 1, wherein the ISG20 protein comprises the amino acid sequence as set forth in SEQ ID NO: 1.

7. The method of claim 1, wherein the ISG20 is recombinantly produced.

8. The method of claim 1, wherein the ISG20 is isolated.

9. The method of claim 1, wherein the placental cell-targeting component comprises an Fc domain of human $IgG_1$.

* * * * *

SEQUENCE LISTING

```
<160> NUMBER OF SEQ ID NOS: 17

<210> SEQ ID NO 1
<211> LENGTH: 181
<212> TYPE: PRT
<213> ORGANISM: Homo sapiens

<400> SEQUENCE: 1

Met Ala Gly Ser Arg Glu Val Val Ala Met Asp Cys Glu Met Val Gly
1               5                   10                  15

Leu Gly Pro His Arg Glu Ser Gly Leu Ala Arg Cys Ser Leu Val Asn
            20                  25                  30

Val His Gly Ala Val Leu Tyr Asp Lys Phe Ile Arg Pro Glu Gly Glu
        35                  40                  45

Ile Thr Asp Tyr Arg Thr Arg Val Ser Gly Val Thr Pro Gln His Met
    50                  55                  60

Val Gly Ala Thr Pro Phe Ala Val Ala Arg Leu Glu Ile Leu Gln Leu
65                  70                  75                  80

Leu Lys Gly Lys Leu Val Val Gly His Asp Leu Lys His Asp Phe Gln
                85                  90                  95

Ala Leu Lys Glu Asp Met Ser Gly Tyr Thr Ile Tyr Asp Thr Ser Thr
            100                 105                 110

Asp Arg Leu Leu Trp Arg Glu Ala Lys Leu Asp His Cys Arg Arg Val
```

-continued

```
        115                 120                 125

Ser Leu Arg Val Leu Ser Glu Arg Leu Leu His Lys Ser Ile Gln Asn
    130                 135                 140

Ser Leu Leu Gly His Ser Ser Val Glu Asp Ala Arg Ala Thr Met Glu
145                 150                 155                 160

Leu Tyr Gln Ile Ser Gln Arg Ile Arg Ala Arg Arg Gly Leu Pro Arg
                165                 170                 175

Leu Ala Val Ser Asp
            180


<210> SEQ ID NO 2
<211> LENGTH: 546
<212> TYPE: DNA
<213> ORGANISM: Homo sapiens

<400> SEQUENCE: 2

atggctggga gccgtgaggt ggtggccatg gactgcgaga tggtggggct ggggccccac      60

cgggagagtg gcctggctcg ttgcagcctc gtgaacgtcc acggtgctgt gctgtacgac     120

aagttcatcc ggcctgaggg agagatcacc gattacagaa cccgggtcag cggggtcacc     180

cctcagcaca tggtgggggc cacaccattt gccgtggcca ggctagagat cctgcagctc     240

ctgaaaggca agctggtggt gggtcatgac ctgaagcacg acttccaggc actgaaagag     300

gacatgagcg gctacacaat ctacgacacg tccactgaca ggctgttgtg gcgtgaggcc     360

aagctggacc actgcaggcg tgtctccctg cgggtgctga gtgagcgcct cctgcacaag     420

agcatccaga acagcctgct tggacacagc tcggtggaag atgcgagggc aacgatggag     480

ctctatcaaa tctcccagag aatccgagcc cgccgagggc tgccccgcct ggctgtgtca     540

gattaa                                                                546


<210> SEQ ID NO 3
<211> LENGTH: 25
<212> TYPE: DNA
<213> ORGANISM: Artificial Sequence
<220> FEATURE:
<223> OTHER INFORMATION: oligonucleotide for use in CRISPR-mediated
      knockout

<400> SEQUENCE: 3

caccgcagca ccgtggacgt tcacg                                            25


<210> SEQ ID NO 4
<211> LENGTH: 25
<212> TYPE: DNA
<213> ORGANISM: Artificial Sequence
<220> FEATURE:
<223> OTHER INFORMATION: oligonucleotide for use in CRISPR-mediated
      knockout

<400> SEQUENCE: 4

aaaccgtgaa cgtccacggt gctgc                                            25


<210> SEQ ID NO 5
<211> LENGTH: 5
<212> TYPE: PRT
<213> ORGANISM: Artificial Sequence
<220> FEATURE:
<223> OTHER INFORMATION: linker

<400> SEQUENCE: 5

Gly Ser Gly Ser Gly
```

-continued 1 5

<210> SEQ ID NO 6
<211> LENGTH: 61
<212> TYPE: DNA
<213> ORGANISM: Artificial Sequence
<220> FEATURE:
<223> OTHER INFORMATION: mutagenesis primer for human interferon-stimulated gene 20-kDa protein (human ISG20)

<400> SEQUENCE: 6
ccccaaagcc caaagacact ctgtatatca ccagggagcc tgaagttaca tgcgtcgttg 60
t 61

<210> SEQ ID NO 7
<211> LENGTH: 61
<212> TYPE: DNA
<213> ORGANISM: Artificial Sequence
<220> FEATURE:
<223> OTHER INFORMATION: mutagenesis primer for human interferon-stimulated gene 20-kDa protein (human ISG20)

<400> SEQUENCE: 7
acaacgacgc atgtaacttc aggctccctg gtgatataca gagtgtcttt gggctttggg 60
g 61

<210> SEQ ID NO 8
<211> LENGTH: 17
<212> TYPE: DNA
<213> ORGANISM: Artificial Sequence
<220> FEATURE:
<223> OTHER INFORMATION: PCR primer for Zika virus

<400> SEQUENCE: 8
ccgctgccca acacaag 17

<210> SEQ ID NO 9
<211> LENGTH: 24
<212> TYPE: DNA
<213> ORGANISM: Artificial Sequence
<220> FEATURE:
<223> OTHER INFORMATION: PCR primer for Zika virus

<400> SEQUENCE: 9
ccactaacgt tcttttgcag acat 24

<210> SEQ ID NO 10
<211> LENGTH: 31
<212> TYPE: DNA
<213> ORGANISM: Artificial Sequence
<220> FEATURE:
<223> OTHER INFORMATION: probe for Zika virus nucleic acid

<400> SEQUENCE: 10
agcctacctt gacaagcagt cagacactca a 31

<210> SEQ ID NO 11
<211> LENGTH: 11
<212> TYPE: PRT
<213> ORGANISM: Artificial Sequence
<220> FEATURE:
<223> OTHER INFORMATION: His-tag

<400> SEQUENCE: 11

Met His His His His His His Ser Ser Leu Ala

-continued

```
1               5                   10


<210> SEQ ID NO 12
<211> LENGTH: 452
<212> TYPE: PRT
<213> ORGANISM: Artificial Sequence
<220> FEATURE:
<223> OTHER INFORMATION: Fusion protein including including ISG20 and Fc
      portion of human IgG

<400> SEQUENCE: 12

Met Arg Gly Pro Ala Val Leu Leu Thr Val Ala Leu Ala Thr Leu Leu
1               5                   10                  15

Ala Pro Gly Ala Gly Ala His His His His His His His His His His
            20                  25                  30

Glu Asn Leu Tyr Phe Gln Gly Met Ala Gly Ser Arg Glu Val Val Ala
        35                  40                  45

Met Asp Cys Glu Met Val Gly Leu Gly Pro His Arg Glu Ser Gly Leu
    50                  55                  60

Ala Arg Cys Ser Leu Val Asn Val His Gly Ala Val Leu Tyr Asp Lys
65                  70                  75                  80

Phe Ile Arg Pro Glu Gly Glu Ile Thr Asp Tyr Arg Thr Arg Val Ser
                85                  90                  95

Gly Val Thr Pro Gln His Met Val Gly Ala Thr Pro Phe Ala Val Ala
            100                 105                 110

Arg Leu Glu Ile Leu Gln Leu Leu Lys Gly Lys Leu Val Val Gly His
        115                 120                 125

Asp Leu Lys His Asp Phe Gln Ala Leu Lys Glu Asp Met Ser Gly Tyr
    130                 135                 140

Thr Ile Tyr Asp Thr Ser Thr Asp Arg Leu Leu Trp Arg Glu Ala Lys
145                 150                 155                 160

Leu Asp His Cys Arg Arg Val Ser Leu Arg Val Leu Ser Glu Arg Leu
                165                 170                 175

Leu His Lys Ser Ile Gln Asn Ser Leu Leu Gly His Ser Ser Val Glu
            180                 185                 190

Asp Ala Arg Ala Thr Met Glu Leu Tyr Gln Ile Ser Gln Arg Ile Arg
        195                 200                 205

Ala Arg Arg Gly Leu Pro Arg Leu Ala Val Ser Asp Gly Ser Gly Ser
    210                 215                 220

Gly Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Tyr Ile Thr Arg Glu Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350
```

-continued

```
Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450


<210> SEQ ID NO 13
<211> LENGTH: 22
<212> TYPE: PRT
<213> ORGANISM: Artificial Sequence
<220> FEATURE:
<223> OTHER INFORMATION: Signal Sequence

<400> SEQUENCE: 13

Met Arg Gly Pro Ala Val Leu Leu Thr Val Ala Leu Ala Thr Leu Leu
1               5                   10                  15

Ala Pro Gly Ala Gly Ala
            20


<210> SEQ ID NO 14
<211> LENGTH: 7
<212> TYPE: PRT
<213> ORGANISM: Tobacco etch virus

<400> SEQUENCE: 14

Glu Asn Leu Tyr Phe Gln Gly
1               5


<210> SEQ ID NO 15
<211> LENGTH: 330
<212> TYPE: PRT
<213> ORGANISM: Homo sapiens

<400> SEQUENCE: 15

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125
```

```
Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 16
<211> LENGTH: 227
<212> TYPE: PRT
<213> ORGANISM: Homo sapiens

<400> SEQUENCE: 16

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
```

-continued

```
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 17
<211> LENGTH: 227
<212> TYPE: PRT
<213> ORGANISM: Homo sapiens

<400> SEQUENCE: 17

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Thr Arg Glu Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225
```